United States Patent
Walker et al.

(10) Patent No.: US 10,876,162 B2
(45) Date of Patent: Dec. 29, 2020

(54) METHODS OF DETECTING MULTI-DRUG RESISTANT ORGANISMS

(71) Applicant: OpGen, Inc., Gaithersburg, MD (US)

(72) Inventors: George Terrance Walker, Chevy Chase, MD (US); Tony Rockweiler, Arlington, VA (US); Alex Saeed, Germantown, MD (US); Vadim Sapiro, North Potomac, MD (US); Rossio Kersey, Germantown, MD (US)

(73) Assignee: OPGEN, INC., Gaithersburg, MD (US)

( * ) Notice: Subject to any disclaimer, the term of this patent is extended or adjusted under 35 U.S.C. 154(b) by 0 days.

(21) Appl. No.: 16/056,037

(22) Filed: Aug. 6, 2018

(65) Prior Publication Data

US 2018/0342310 A1 Nov. 29, 2018

Related U.S. Application Data

(63) Continuation of application No. 14/657,908, filed on Mar. 13, 2015, now abandoned.

(60) Provisional application No. 61/952,795, filed on Mar. 13, 2014, provisional application No. 62/116,860, filed on Feb. 16, 2015.

(51) Int. Cl.
| | |
|---|---|
| *C12Q 1/6883* | (2018.01) |
| *G06F 19/00* | (2018.01) |
| *G16B 25/00* | (2019.01) |
| *C12Q 1/689* | (2018.01) |
| *G16H 10/40* | (2018.01) |
| *G16H 20/10* | (2018.01) |

(52) U.S. Cl.
CPC .......... *C12Q 1/6883* (2013.01); *C12Q 1/689* (2013.01); *G06F 19/00* (2013.01); *G06F 19/3456* (2013.01); *G16B 25/00* (2019.02); *G16H 10/40* (2018.01); *G16H 20/10* (2018.01); *C12Q 2600/106* (2013.01); *C12Q 2600/158* (2013.01); *Y02A 90/26* (2018.01)

(58) Field of Classification Search
None
See application file for complete search history.

(56) References Cited

U.S. PATENT DOCUMENTS

| 2009/0163382 A1 | 6/2009 | Oh et al. |
| 2011/0151458 A1 | 6/2011 | Garaizar Candina et al. |
| 2013/0183679 A1 | 7/2013 | Ploy et al. |
| 2015/0259729 A1 | 9/2015 | Walker et al. |
| 2017/0253917 A1 | 9/2017 | Walker et al. |

FOREIGN PATENT DOCUMENTS

| CN | 102899414 A | 1/2013 |
| WO | WO 2010/039763 A2 | 4/2010 |
| WO | WO 2011/138402 A1 | 11/2011 |
| WO | WO 2012/032158 A1 | 3/2012 |
| WO | WO 2013/117746 A1 | 8/2013 |
| WO | WO 2013/163210 A1 | 10/2013 |
| WO | WO 2015/114094 A1 | 8/2015 |
| WO | WO 2015/138991 A2 | 9/2015 |
| WO | WO 2015/184017 A1 | 12/2015 |

OTHER PUBLICATIONS

Agyekum, A. et al. "Predictability of Phenotype in Relation to Common [beta]-Lactam Resistance Mechanisms in *Escherichia coli* and Klebsiella pneumonia", Journal of Microbiology (2016); 54(5): 1243-1250.
Aitmhand et al., "Plasmid-mediated TEM-3 extended-spectrum ß-lactamase production in *Salmonella typhimurium* in Casablanca." J Antimicrob Chemother (2002), 49: 169-172.
Arnold et al., "Emergence of Klebsiella pneumoniae Carbapenemase (KPC)-Producing Bacteria", South Med J (2011), 104: 40-45.
Bahar et al., "Detection of VIM-5 metallo-ß-lactamase in a Pseudomonas aeruginosa clinical isolate from Turkey", J Antimicrob Chemother (2004), 54: 282-283.
Barnaud et al., "*Salmonella enteritidis*: AmpC Plasmid-Mediated Inducible ß-Lactamase (DHA-1) with an ampR Gene from Morganella morganii", Antimicrob Agents Chemother (1998), 42: 2352-2358.
Bauernfeind et al., "A Novel Type of AmpC ß-Lactamase, ACC-1, Produced by a Klebsiella pneumoniae Strain Causing Nosocomial Pneumonia", Antimicrob Agents Chemother (1999), 43: 1924-1931.
Bauernfeind et al., "Characterization of the Plasmidic ß-Lactamase CMY-2, Which Is Responsible for Cephamycin Resistance", Antimicrob Agents Chemother (1996), 40: 221-224.
Bauernfeind et al., "Comparative Characterization of the Cephamycinase blaCMY-1 Gene and Its Relationship with Other b-Lactamase Genes", Antimicrob Agents Chemother (1996), 40: 1926-1930.
Berrazeg et al., "New Delhi Metallo-Beta-Lactamase Around the World: An eReview Using Google Maps", Eurosurveillance (2014), 19: 1-14.
Bhattacharya, "Early diagnosis of resistant pathogens. How can it improve antimicrobial treatment?" Virulence (2013); 4 (2):172-184.
Bonnet et al., "A Novel Class A Extended-Spectrum b-Lactamase (BES-1) in Serratia marcescens Isolated in Brazil", Antimicrob Agents Chemother (2000), 44: 3061-3068.

(Continued)

*Primary Examiner* — Carla J Myers
(74) *Attorney, Agent, or Firm* — Cooley LLP; Ivor Elrifi; Cynthia Kozakiewicz

(57) ABSTRACT

The present invention provide methods using genes associated with multi-drug resistance for rapidly detecting a patient colonized or infected with an multi-drug resistant organism and administrating the appropriate precautions and/or treatment.

24 Claims, 9 Drawing Sheets

Specification includes a Sequence Listing.

(56) References Cited

OTHER PUBLICATIONS

Bou et al., "OXA-24, a Novel Class D ß-Lactamase with Carbapenemase Activity in an Acinetobacter baumannii Clinical Strain", Antimicrob Agents Chemother (2000), 44: 1556-1561.
Bradford et al., "Imipenem Resistance in Klebsiella pneumoniae is Associated with the Combination of ACT-1, a Plasmid-Mediated AmpC ß-Lactamase, and the Loss of an Outer Membrane Protein", Antimicrob Agents Chemother (1997), 41: 563-569.
Bradley P. et al. "Rapid antibiotic-resistance predictions from genome sequence data for *Staphylococcus aureus* and *Mycobacterium tuberculosis*", Nature Communications (2015); 6: 10063, and Corrigendum, 15 pages.
Castanheira et al., "Molecular characterization of a ß-Lactamase Gene, blaGIM-1, encoding a new subclass of Metallo-b-Lactamase", Antimicrob Agents Chemother (2004), 48: 4654-4661.
Chaves et al., "SHV-1 b-Lactamase is Mainly a Chromosomally Encoded Species-Specific Enzyme in Klebsiella pneumoniae", Antimicrob Agents Chemother (2001), 45: 2856-2861.
Cook, Nancy R. "Use and misuse of the receiver operating characteristic curve in risk prediction." Circulation (2007); 115.7: 928-935.
Corkill et al., "SHV-27, A Novel Cefotaxime-Hydrolysing b-Lactamase, Identified in Klebsiella pneumoniae isolates from a Brazilian hospital", Journal of Antimicrobial Chemotherapy (2001), 47: 463-465.
Crowley et al., "Expression of SHV-2 b-Lactamase and of Reduced Amounts of b OmpK36 Porin in Klebsiella pneumoniae Results in Increased Resistance to Cephalosporins and Carbapenems", Antimicrob Agents Chemother (2002), 46: 3679-3682.
Da Silva et al., "Molecular Characterization of blaIMP-5, a New Integron-Borne Metallo-b-lactamase Gene from an Acinetobacter baumannii Nosocomial Isolate in Portugal", FEMS Microbiology Letters (2002), 215: 33-39.
Dalla-Costa et al., "Outbreak of Carbapenem-Resistant Acinetobacter baumannii Producing the OXA-23 Enzyme in Curitiba, Brazil", J Clin Micro (2003), 41 (7): 3403-3406.
Danel et al., "OXA-15, an Extended-Spectrum Variant of OXA-2 b-Lactamase, Isolated from a Pseudomonas aeruginosa Strain", Antimicrob Agents Chemother (1997), 41: 785-790.
Fonseca et al., "Biochemical Characterization of SFC-1, a Class A Carbapenem-Hydrolyzing b-Lactamase", Antimicrob Agents Chemother (2007), 51: 4512-4514.
Francis, R.O., et al., "Rapid Detection of Klebsiella pneumoniae Carbapenemase Genes in Enterobacteriaceae Directly From Blood Culture Bottles by Real-Time PCR." American Journal of Clinical Pathology (2012); 137(4): 627-632.
Girlich et al., "Biochemical Characterization of the Naturally Occurring Oxacillinase OXA-50 of Pseudomonas aeruginos," Antimicrob Agents Chemother (2004), 48: 2043-2048.
Girlich et al., "OXA-60, a Chromosomal, Inducible, and Imipenem-Hydrolyzing Class D b-Lactamase from Ralstonia pickettii", Antimicrob Agents Chemother (2004), 48: 4217-4225.
Gutmann et al., "Plasmid-Mediated Beta-Lactamase (TEM-7) Involved in Resistance to Ceftazidime and Aztreonam", Rev Infect Dis (1988), 10: 860-866.
Gutmann et al., "SHV-5, a Novel SHV-Type ß-Lactamase that Hydrolyzes Broad-Spectrum Cephalosporins and Monobactams", Antimicrob Agents Chemother (1989), 33 (6): 951-956.
Héritier et al., "Genetic and Biochemical Characterization of a Chromosome-Encoded Carbapenem-Hydrolyzing Ambler Class D b-Lactamase from Shewanella algae", Antimicrob Agents Chemother (2004), 48: 1670-1675.
Horii et al., "Characterization of a Plasmid-Borne and Constitutively Expressed blaMOX-1 Gene Encoding AmpC-Type b-Lactamase", Gene (1994), 139: 93-98.
International Preliminary Report on Patentability, for International Application No. PCT/US2015/020590, dated Sep. 13, 2016, 10 pages.
International Search Report and Written Opinion for International Application No. PCT/US2017/021209, dated May 29, 2017, 15 pages.
International Search Report, for International Application No. PCT/US2015/020590, dated Sep. 18, 2015, 9 pages.
Jeong et al., "Molecular Characterization of Extended-Spectrum Beta-Lactamases Produced by Clinical Isolates of Klebsiella pneumoniae and *Escherichia coli* from a Korean Nationwide Survey", J Clinic Microb (2004), 42: 2902-2906.
Jordana-Lluch et al. "Rapid Diagnosis of Bloodstream Infections with PCR Followed by Mass Spectrometry," PLOS ONE, vol. 8, No. 4, Apr. 23, 2013, p. e62108.
Juan, et al., "Characterization of the New Metallo-ß-Lactamase VIM-13 and Its Integron-Borne Gene from a Pseudomonas aeruginosa Clinical Isolate in Spain", Antimicrob Agents Chemother (2008), 52: 3589-3596.
Koh et al., "Carbapenem-Resistant Klebsiella pneumoniae in Singapore Producing IMP-1 b-Lactamase and Lacking an Outer Membrane Protein", Antimicrob Agents Chemother (2001), 45: 1939-1940.
Kos, V. N. et al. "The Resistome of Pseudomonas aeruginosa in Relationship to Phenotypic Susceptibility", Antimicrobial Agents and Chemotherapy (2015); 59(1): 427-436.
Lakshmi et al., "Role of Beta Lactamases in Antibiotic Resistance: a Review", Int Res J Pharm (2014), 5: 37-40.
Lee et al., "Novel Acquired Metallo-ß-Lactamase Gene, blaSIM-1, in a Class 1 Integron from Acinetobacter baumannii Clinical Isolates from Korea", Antimicrob Agents Chemother (2005), 49: 4485-4491.
Llop, P., et al., "Development of a Highly Sensitive Nested-PCR Procedure Using a Single Closed Tube for Detection of Erwinia amylovora in Asymptomatic Plant Material." Appl Environ Microbiol. (2000); 66(5): 2071-2078.
Lupo et al. "Non-phenotypic tests to detect and characterize antibiotic resistance mechanisms in Enterobacteriaceae," Diagnostic Microbiology and Infectious Diseases (2013); 77(3): 179-194.
Matsumoto et al., "Characterization of SFO-1, A Plasmid-Mediated Inducible Class A ß-Lactamase from Enterobacter cloacae", Antimicrob Agents Chemother (1999), 43: 307-313.
Mazzariol et al., "Detection of a New SHV-Type Extended-Spectrum ß-Lactamase, SHV-31, in a Klebsiella pneumoniae Strain Causing a Large Nosocomial Outbreak in the Netherlands", Antimicrob Agents Chemother (2007), 51: 1082-1084.
Menezes et al. "Diagnosis by real-time polymerase chain reaction of pathogens and antimicrobial resistance genes in bone marrow transplant patients with bloodstream infections." BMC Infectious Diseases (2013); 13 (1): 166.
Miró et al., "*Escherichia coli* Producing an ACC-1 Class C ß-Lactamase Isolated in Barcelona, Spain", Antimicrob Agents Chemother (2005), 49 (2): 866-867.
Monteiro et al. "Rapid detection of carbapenemase genes by multiplex real-time PCR," Journal of Antimicrobial Chemotherapy (2012); 67: 906-909.
Mossakowska et al., "Oxacillin-Hydrolysing ß-Lactamases, A Comparative Analysis at Nucleotide and Amino Acid Sequence Levels", Eur J Biochem (1989), 180: 309-318.
Mugnier et al., "A TEM-Derived Extended-Spectrum ß-Lactamase in Pseudomonas aeruginosa", Antimicrob Agents Chemother (1996), 40 (11): 2488-2493.
Mulvey et al., "Ambler Class A Extended-Spectrum Beta-Lactamase-Producing *Escherichia coli* and *Klebsiella* spp. in Canadian Hospitals", Antimicrob Agents Chemother (2004), 48 (4): 1204-1214.
Naas et al., "Identification of CTX-M-Type Extended-Spectrum-ß-Lactamase Genes Using Real-Time PCR and Pyrosequencing", Antimicrob Agents Chemother (2007), 51 (1): 223-230.
Naas et al., "Minor Extended-Spectrum ß-Lactamases", Clin Microbiol Infect (2008), 14 (1): 42-52.
Naas and Nordmann, "Oxa-Type ß-Lactamases", Current Pharmaceutical Design (1999), 5: 865-879.
Nakano et al., "CFE-1, A Novel Plasmid-Encoded AmpC ß-Lactamase with an ampR Gene Originating from Citrobacter freundii", Antimicrob Agents Chemother (2004), 48 (4): 1151-1158.

(56) References Cited

OTHER PUBLICATIONS

Nordmann and Naas, "Sequence Analysis of PER-1 Extended-Spectrum ß-Lactamase from Pseudomonas aeruginosa and Comparison with Class A ß-Lactamases", Antimicrob Agents Chemother (1994), 38 (1): 104-114.
O'Marcaigh, Aengus S., and Jackson, Robert M. "Estimating the predictive value of a diagnostic test: how to prevent misleading or confusing results." Clinical Pediatrics (1993); 32.8: 485-491.
Opazo et al., "OXA-Type Carbapenemases in Acinetobacter baumannii in South America", J Infect Dev Ctries (2012), 6 (4): 311-316.
Papanicolaou et al., "Novel Plasmid-Mediated ß-Lactamase (MIR-1) Conferring Resistance to Oxyimino- and α-Methoxy ß-Lactams in Clinical Isolates of Klebsiella pneumoniae", Antimicrob Agents Chemother (1990), 34 (11): 2200-2209.
Pepe, Margaret Sullivan, et al. "Limitations of the odds ratio in gauging the performance of a diagnostic, prognostic, or screening marker." American Journal of Epidemiology (2004); 159.9: 882-890.
Perilli et al., "Characterization of a New Extended-Spectrum ß-Lactamase (TEM-87) Isolated in Proteus mirabilis during an Italian Survey", Antimicrob Agents Chemother (2002), 46 (3): 925-928.
Philippon et al., "OXA-18, a Class D Clavulanic Acid-Inhibited Extended-Spectrum ß-Lactamase from Pseudomonas aeruginosa", Antimicrob Agents Chemother (1997), 41 (10): 2188-2195.
Philippon et al., "Plasmid-Determined AmpC-Type ß-Lactamases." Antimicrob Agents Chemother (2002), 46 (1): 1-11.
Poirel et al., "BEL-1 A Novel Clavulanic Acid-Inhibited Extended-Spectrum ß-lactamase, and the Cass 1 Integron In120 in Pseudomonas aeruginosa", Antimicrob Agents Chemother (2005), 49(9): 3743-3748.
Poirel et al., "Biochemical Sequence Analyses of GES-1, A Novel class a Extended Spectrum ß-Lactamase, and the Class 1 Integron In52 from Klebsiella pneumoniae", Antimicrob Agents Chemother (2000), 44 (3): 622-632.
Poirel et al., "Chromosome-Encoded Ambler Class D ß-Lactamase of Shewanella oneidensis as a Progenitor of Carbapenem-Hydrolyzing Oxacillinase", Antimicrob Agents Chemother (2004), 48 (1): 348-351.
Poirel et al., "Emergence of Oxacillinase-Mediated Resistance to Imipenem in Klebsiella pneumoniae", Antimicrob Agents Chemother (2004), 48 (1): 15-22.
Poirel et al., "Integron-Located oxa-32 Gene Cassette Encoding an Extended-Spectrum Variant of OXA-2 ß-Lactamase from Pseudomonas aeruginosa", Antimicrob Agents Chemother (2002), 46 (2): 566-569.
Poirel et al., "Molecular and Biochemical Characterization of VEB-1, A Novel Class A Extended-Spectrum ß-Lactamase Encoded by an *Escherichia coli* Integron Gene", Antimicrob Agents Chemother (1999), 43 (3): 573-581.
Poirel et al., "OXA-58, A Novel Class D ß-Lactamase Involved in Resistance to Carbapenems in Acinetobacter baumannii", Antimicrob Agents Chemother (2005), 49 (1): 202-208.
Pottumarthy et al., "NmcA Carbapenem Hydrolyzing Enzyme in Enterobacter cloacae in North America", Emerging Infectious Diseases (2003), 9: 999-1002.
Queenan et al., "SME-Type Carbapenem-Hydrolyzing Class Diverse Serratia marcescens Strains A ß-Lactamases from Geographically diverse Serratia marcescens strains", Antimicrob Agents Chemother (2000), 44 (11): 3035-3039.
Quinn et al., "Novel Plasmid-Mediated ß-Lactamase (TEM-10) Conferring Selective Resistance to Ceftazidime and Aztreonam in Clinical Isolates of Klebsiella pneumoniae", Antimicrob Agents Chemother (1989), 33 (9): 1451-1456.
Raghunath et al., "New metallo ß-lactamase NDM-1", Indian J Med Res (2010), 132 (5): 478-481.
Rampersad, J.N., et al., "A nested-PCR with an Internal Amplification Control for the detection and differentiation of Bartonella henselae and B. clarridgeiae: an examination of cats in Trinidad." BMC Infect Dis. (2005); 5: 63, 6 pages.
Rasmussen et al., "Characterization of IMI-1 ß-Lactamase, a Class A Carbapenem-Hydrolyzing Enzyme from Enterobacter cloacae", Antimicrob Agents Chemother (1996), 40 (9): 2080-2086.
Sacha et al., "The KPC Type R-Lactamases: New Enzymes that Confer Resistance to Carbapenems in Gram-negative Bacilli", Folia Histochemica Et Cytobiologica (2009), 47 (4): 537-543.
Schneider et al., "Novel Carbapenem-Hydrolyzing Oxacillinase OXA-62 from Pandoraea pnomenusa", Antimicrob Agents Chemother (2006), 50 (4): 1330-1335.
Singapore Application No. 11201607588W, Written Opinion dated Oct. 19, 2017, 3 pages.
Singapore Application No. 11201609867V, Written Opinion dated Oct. 27, 2017, 7 pages.
Shultz, "Clinical Interpretation of Laboratory Procedures," Chapter 14 in Teitz, Fundamentals of Clinical Chemistry, Burtis and Ashwood (eds.), 4th edition 1996, W.B. Saunders Company, pp. 192-199.
Silva et al., "TLA-1: A New Plasmid-Mediated Extended-Spectrum ß-Lactamase from *Escherichia coli*", Antimicrob Agents Chemother (2000), 44 (4): 997-1003.
Stoesser, N., et al. "Predicting antimicrobial susceptibilities for *Escherichia coli* and Klebsiella pneumoniae isolates using whole genomic sequence data", Journal of Antimicrobial Chemotherapy (2013); 68 (10): 2234-2244.
Suzuki et al. "Supplementary information. Supplementary Figures", Nature Methods, 2014, 14 pages. Retrieved from the Internet: URL:https://www.nature.com/article-assets/npg/ncomms/2014.
Suzuki, S. et al. "Prediction of antibiotic resistance by gene expression profiles", Nature Communications (2014); 5: 5792.
Swick, M.C. et al. "Novel Conserved Genotypes Correspond to Antibiotic Resistance Phenotypes of *E. coli* Clinical Isolates", PLOS ONE (2013); 8(6): e65961.
Taneja et al., "High Occurrence of blaCMY-1 AmpC Lactamase Producing *Escherichia coli* in Cases of Complicated Urinary Tract Infection (UTI) from a Tertiary Health Care Centre in North India", Indian J Med Res (2000), 136 (2): 289-291.
Toleman et al., "blaNim7 Evolutionarily Distinct Metallo-β-Lactamase Gene in a Pseudomonas aeruginosa Isolate from the United States", Antimicrob Agents Chemother (2004), 48 (1): 329-332.
Toleman et al., "Molecular and Biochemical Characterization of OXA-45, an Extended-Spectrum Class 2d' β-Lactamase in Pseudomonas aeruginosa", Antimicrob Agents Chemother (2003), 47 (9): 2859-2863.
Toleman et al., "Molecular characterization of SPM-1, A Novel Metallo-β-Lactamasel solated in Latin America: Report from the SENTRY Antimicrobial Surveillance Programme", Journal of Antimicrobial Chemotherapy (2002), 50 (5): 673-679.
Vahaboglu et al., "High Prevalence of OXA-51-Yype class D β-Lactamases Among Ceftazidime-Resistant Clinical lisolates of *Acinetobacter* spp.: Co-Existence with OXA-58 in Multiple Centres", J Antimicrob Chemother (2006), 58 (3): 537-542.
Walsh et al., "Metallo-β-Lactamases: the Quiet before the Storm?", Clin Microbiol Rev (2005), 18 (2): 306-325.
Written Opinion, for International Application No. PCT/US2015/020590, dated Sep. 18, 2015, 9 pages.
Yigit et al., "Novel Carbapenem-Hydrolyzing β-Lactamase, KPC-1, from a Carbapenem-Resistant Strain of Klebsiella pneumoniae", Antimicrob Agents Chemother (2001), 45 (4): 1151-1161.
Yong et al., "Characterization of a New Metallo-β-Lactamase Gene, blaNDM-1, and a Novel Erythromycin Esterase Gene Carried on a Unique Genetic Structure in Klebsiella pneumoniae Sequence Type 14 from India", Antimicrob Agents Chemother (2009), 53 (12): 5046-5054.
Zweig, Mark H., et al. "ROC curve analysis: an example showing the relationships among serum lipid and apolipoprotein concentrations in identifying patients with coronary artery disease." Clinical Chemistry (1992); 38.8: 1425-1428.
U.S. Appl. No. 14/657,908, Office Action dated Nov. 7, 2016, 23 pages.
U.S. Appl. No. 14/657,908, Office Action dated Jul. 3, 2017, 29 pages.
U.S. Appl. No. 14/657,908, Office Action dated Feb. 5, 2018, 29 pages.

(56) References Cited

OTHER PUBLICATIONS

Bearman et al., "A controlled trial of universal gloving versus contact precautions for preventing the transmission of multidrug-resistant organisms," Am J Infect Control, 2007, vol. 35, pp. 650-655.

Park et al., "Clinical and microbiologic characteristics of cephalosporin-resistant *Escherichia coli* at three centers in the United States," Antimicrobial Agents and Chemotherapy, vol. 56, Apr. 2012, pp. 1870-1876.

| MDRO Assay | Escherichia coli | Klebsiella pneumoniae | Serratia marcescens | Acinetobacter baumannii | Pseudomonas aeruginosa | Enterobacter cloacae | Citrobacter freundii | Enterococcus faecalis | Enterococcus faecium | Staphylococcus aureus |
|---|---|---|---|---|---|---|---|---|---|---|
| KPC | 8 | 71 | | 1 | 8 | 6 | 5 | | | |
| NDM | 36 | >100 | | 21 | 10 | 4 | 4 | | 1 | |
| VIM(A) | 1 | 7 | 4 | 9 | >100 | 5 | 1 | | | |
| VIM(B) | | 7 | 4 | 9 | >100 | 5 | 1 | | | |
| VIM(C) | | 1 | | 1 | 2 | 2 | | | | |
| IMP(A) | 2 | 4 | 10 | 6 | 32 | 1 | 1 | | | |
| IMP(B) | 2 | 4 | 10 | 6 | 32 | 1 | 1 | | | |
| OXA(A) | | | | 20 | | | | | | |
| OXA(B) | | 1 | | >100 | | | | | | |
| OXA(C) | 2 | 15 | 3 | | | 3 | 1 | | | |
| CTX-M(A) | >100 | 94 | | 4 | 1 | 15 | 4 | | | |
| CTX-M(B) | 16 | 56 | | 3 | 13 | 1 | | | | |
| VanA | | | | | | | | 9 | 21 | 2 |

Number of GenBank Hits

FIG. 1

| Organism | Genotype | MDRO Assay | LOD (CFU/swab) | Ct value for LOD |
|---|---|---|---|---|
| E. cloacae | KPC 3 | Kpc | 84 | 15 |
| K. pneumoniae | CTX-M-28 | Ctx-M(A) | 79 | 15 |
| K. pneumoniae | OXA 48 | Oxa(C) | 79 | 14 |
| K. pneumoniae | IMP-1 | Imp(A) | 13 | 19 |
| S. marcescens | VIM-4 | Vim(A) | 154 | 16 |
| K. pneumoniae | NDM-1 | NDM | 93 | 16 |
| A. baumannii | OXA-23 | OXA(B) | 109 | 14 |
| E. faecium | Van A | Van A | 207 | 18 |
| K. pneumoniae | CTX-M-2 | CTX-M(B) | 151 | 15 |
| E. Cloacae | VIM-5 | VIM(C) | 154 | 14 |
| P. aeruginosa | VIM-2 | VIM(B) | 37 | 16 |
| K. Pneumoniae | CTX-M-1 | CTX-M(A) | 38 | 17 |
| K. Pneumoniae | IMP-8 | IMP(B) | 66 | 17 |
| A. baumannii | ?? | OXA(A) | 11 | 18 |

CFU = colony forming units of bacteria

FIG. 2

| Species | Reported Genotype | Assay Result from OpGen's MDRO Test | Species | Reported Genotype | Assay Result from OpGen's MDRO Test |
|---|---|---|---|---|---|
| E. coli | NDM-1 | Ndm | E. cloacae | VIM-2 | Vim(A) and Vim(B) |
| K. pneumoniae | CTX-M-15 | Ctx-M(A) | K. pneumoniae | CTX-M-14 and IMP-1 | Imp(A) |
| P. aeruginosa | VIM-2 | Vim(A) and Vim(B) | K. pneumoniae | IMP-8 | Imp(B) |
| E. cloacae | KPC-3 | Kpc | K. pneumoniae | CTX-M-65 | negative |
| E. cloacae | VIM-5 | Vim-C | K. pneumoniae | CTX-M-38 | negative |
| E. coli | CTX-M-15 and NDM-4 | Ctx-M(A) and Ndm | K. pneumoniae | CTX-M-15, OXA-181 | CTX-M(A), OXA(C) |
| E. coli | CTX-M-15 | Ctx-M(A) | S. marcescens | CTX-M-2, CMY-2 | CTX-M(B) |
| E. coli | TEM-29 | negative | E. coli | CTX-M-8 | negative |
| E. coli | SHV-31 | negative | S. marcescens | OXA-48 | OXA(C) |
| P. aeruginosa | VIM | Vim(A) and Vim(B) | E. cloacae | CTX-M-15, ACT/MIR, NDM-1; OXA-181 | CTX-M(A), Ndm, Oxa(C) |
| E. cloacae | CTX-M-2 | Ctx-M(B) | E. cloacae | CTX-M-9, ACT/MIR | negative |
| E. coli | KPC-2 | Kpc | E. coli | CTX-M-2 | CTX-M(B) |
| E. cloacae | CTX-M-15 and NDM-1 | Ctx-M(A) and Ndm | E. coli | CTX-M-65 | negative |
| K. pneumoniae | CTX-M-15 and IMP-26 | Ctx-M(A) and Imp(A) | E. coli | KPC-2 | Kpc |
| K. pneumoniae | NDM-1 | Ndm | E. cloacae | CTX-M-14 | negative |
| E. cloacae | CTX-M-15 and IMP-4 | Ctx-M(A) and Imp(A) | E. cloacae | KPC-2 | Kpc |
| S. marcescens | VIM-4 | Vim(A) and Vim(B) | E. cloacae | CTX-M-14, NDM | Ndm |
| P. aeruginosa | VIM-4 | Vim(A) and Vim(B) | K. oxytoca | CTX-M-2 | CTX-M(B) |
| K. pneumoniae | CTX-M-15 and VIM-27 | Ctx-M(A), Vim(A) and Vim(B) | K. oxytoca | KPC-2 | Kpc |
| K. pneumoniae | VIM-26 | Vim(A) and Vim(B) | K. pneumoniae | SHV-11(b), CTX-M-9 | negative |
| K. pneumoniae | VIM-1 | Vim(A) and Vim(B) | E. cloacae | SHV-31(e), TEM-1(b), CTX-M-15, NDM-1 | CTX-M(A), Ndm |
| E. coli | CTX-M-15 | Ctx-M(A) | K. oxytoca | SHV-1(b), TEM-1(b), CTX-M-15 | CTX-M(A) |
| P. aeruginosa | IMP-13 | Imp(B) | C. freundii | KPC-2 | Kpc |
| K. pneumoniae | CTX-M-22 and OXA-48 | Ctx-M(A) and Oxa-C | K. pneumoniae | CTX-M-2 | CTX-M(B) |
| E. coli | CTX-M-28 and OXA-48 | Ctx-M(A) and Oxa-C | K. pneumoniae | SHV-11(b), KPC-3 | Kpc |
| E. coli | CTX-M-55 and CTX-M-79 | Ctx-M(A) | C. freundii | CTX-M-15 | CTX-M(A) |
| K. pneumoniae | KPC-2 | Kpc | E. coli | TEM-1(b), CTX-M-14, OXA-48 | OXA(C) |
| E. cloacae | CTX-M-3 and VIM-4 | Ctx-M(A), Vim(A) and Vim(B) | K. pneumoniae | SHV-11(b), TEM-1(b), CTX-M-27 | negative |
| K. pneumoniae | SHV-38 | negative | E. cloacae | SHV-1(b), CTX-M-9 | negative |
| K. oxytoca | TEM-20, CMY-2 | CTX-M(A) | K. oxytoca | SHV-5(e), CTX-M-27 | negative |
| S. marcescens | SHV-12(e), TEM-1(b), CTX-M-22, DHA-1 | negative | E. coli | CTX-M-15 | CTX-M(A) |
| | KPC-2 | Kpc | K. oxytoca | | |

FIG. 3

| Assay | Ci Values | | | Day One | | | Ci Values | | | Day Two | | |
|---|---|---|---|---|---|---|---|---|---|---|---|---|
| | Positive Control | Negative Control | No Template Control | High Target Level | Mid Target Level | Low Target Level | Positive Control | Negative Control | No Template Control | High Target Level | Mid Target Level | Low Target Level |
| KPC | 13 | NEG | NEG | 4<br>4<br>4 | 9<br>8<br>8 | 12<br>13<br>11 | 12 | NEG | NEG | 4<br>4<br>5 | 7<br>7<br>7 | 11<br>11<br>10 |
| NDM | 14 | NEG | NEG | 5<br>5<br>5 | 9<br>9<br>9 | 12<br>14<br>12 | 13 | NEG | NEG | 6<br>5<br>4 | 8<br>8<br>8 | 12<br>12<br>11 |
| VIM(A) | 17 | NEG | NEG | 8<br>8<br>8 | 14<br>12<br>13 | 16<br>18<br>15 | 14 | NEG | NEG | 7<br>8<br>9 | 12<br>11<br>11 | 14<br>14<br>13 |
| VIM(B) | 17 | NEG | NEG | 8<br>9<br>9 | 13<br>13<br>13 | 16<br>18<br>15 | 15 | NEG | NEG | 8<br>10<br>11 | 13<br>12<br>11 | 15<br>15<br>14 |
| VIM© | 10 | NEG | NEG | 3<br>3<br>3 | 5<br>5<br>5 | 8<br>9<br>6 | 8 | NEG | NEG | 3<br>3<br>3 | 4<br>4<br>4 | 7<br>7<br>5 |
| IC | 13 | 11 | 14 | 12<br>11<br>11 | 12<br>13<br>12 | 12<br>14<br>12 | 13 | 12 | 999 | 12<br>12<br>12 | 12<br>12<br>12 | 12<br>12<br>12 |
| OXA(A) | 13 | NEG | NEG | 5<br>5<br>5 | 9<br>9<br>8 | 12<br>14<br>12 | 12 | NEG | NEG | 5<br>5<br>5 | 7<br>7<br>7 | 11<br>11<br>10 |
| OXA(B) | 12 | NEG | NEG | 4<br>4<br>5 | 8<br>7<br>7 | 11<br>13<br>11 | 12 | NEG | NEG | 5<br>5<br>6 | 8<br>7<br>7 | 11<br>10<br>10 |
| OXA© | 15 | NEG | NEG | 6<br>6<br>6 | 10<br>10<br>10 | 14<br>15<br>13 | 13 | NEG | NEG | 5<br>5<br>5 | 8<br>8<br>8 | 12<br>11<br>10 |
| IMP(A) | 18 | NEG | NEG | 8<br>8<br>9 | 13<br>12<br>12 | 16<br>17<br>15 | 14 | NEG | NEG | 6<br>6<br>6 | 9<br>9<br>9 | 13<br>12<br>11 |
| IMP(B) | 18 | NEG | NEG | 9<br>10<br>9 | 14<br>14<br>13 | 17<br>18<br>17 | 15 | NEG | NEG | 8<br>8<br>8 | 10<br>11<br>11 | 15<br>14<br>13 |
| VAN A | 12 | NEG | NEG | 4<br>4<br>4 | 7<br>7<br>7 | 10<br>12<br>10 | 8 | NEG | NEG | 3<br>3<br>3 | 4<br>4<br>4 | 8<br>7<br>6 |
| CTX(A) | 14 | NEG | NEG | 6<br>6<br>6 | 10<br>10<br>10 | 14<br>15<br>13 | 13 | NEG | NEG | 6<br>6<br>6 | 9<br>8<br>9 | 12<br>13<br>12 |
| CTX(B) | 15 | NEG | NEG | 6<br>6<br>6 | 11<br>11<br>10 | 15<br>15<br>14 | 13 | NEG | NEG | 5<br>5<br>5 | 8<br>8<br>8 | 12<br>12<br>10 |

FIG. 4

ResistomeTest:
*for colony isolates*

CRE:
- KPC-2
- NDM-1
- OXA-48
- VIM-1/VIM-13
- IMP-1

ESBL:
- CTX-M-1
- CTX-M-2
- CTX-M-8/25
- CTX-M-9
- SHV-238/240
- SHV-156
- TEM-104
- TEM-164
- TEM-G238/240
- BEL-1
- VEB-1
- GES-1
- PER-1
- SFO-1
- BES-1
- TLA-1

AmpC:
- ACC-1
- ACC-3
- MOX-1/CMY-1
- CMY-2/CFE-1
- CMY-41
- ACT-1/MIR-1
- DHA-1
- FOX-1

Carbapenemase:
- IMP-5
- OXA-2
- OXA-10
- OXA-18
- OXA-23
- OXA-24
- OXA-45
- OXA-50
- OXA-51
- OXA-54
- OXA-55
- OXA-58
- OXA-60
- OXA-62
- IMI-1/NMC-A
- SME-1
- GIM-1
- SPM-1
- SFC-1

FIG. 5

Complete Solution for High-resolution Transmission Event Confirmation

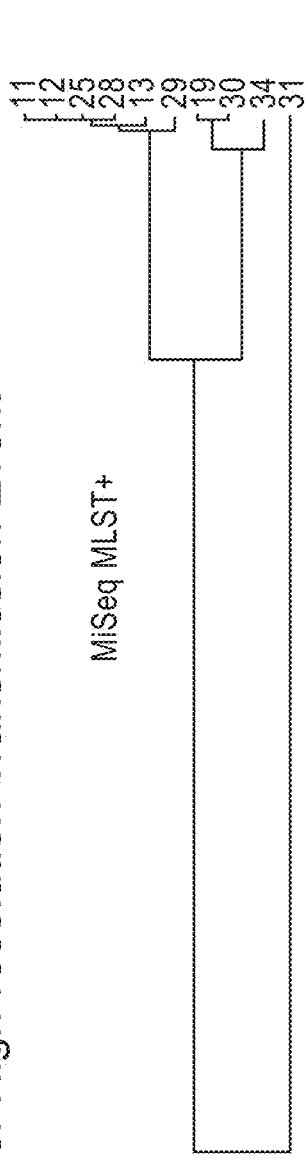

MiSeq MLST+

| | Positive Results from MDRO Gene Test | | | | Positive Results from Resistome Test | | | | | | Positive Results from Whole Genome Sequencing | | | |
|---|---|---|---|---|---|---|---|---|---|---|---|---|---|---|
| Sample | KPC | CTX-M | Lighthouse Profile | KPC | CTX-M | OXA | SHV | TEM | Lighthouse Profile | KPC | CTX-M | OXA | SHV | TEM |
| 11 | KPC | | K1:CRE:KPC | KPC | | OXA-2 | wild type | wild type | K1:CRE:KPC_O2_S4_T4 | KPC-3 | | OXA-2 | SHV-11 | TEM-1 |
| 12 | KPC | | K1:CRE:KPC | KPC | | OXA-2 | wild type | wild type | K1:CRE:KPC_O2_S4_T4 | KPC-3 | | OXA-2 | SHV-11 | TEM-1 |
| 25 | KPC | | K1:CRE:KPC | KPC | | OXA-2 | wild type | wild type | K1:CRE:KPC_O2_S4_T4 | KPC-3 | | OXA-2 | SHV-11 | TEM-1 |
| 28 | KPC | | K1:CRE:KPC | KPC | | OXA-2 | wild type | wild type | K1:CRE:KPC_O2_S4_T4 | KPC-3 | | OXA-2 | SHV-11 | TEM-1 |
| 13 | KPC | | K1:CRE:KPC | KPC | | OXA-2 | wild type | wild type | K1:CRE:KPC_O2_S4_T4 | KPC-3 | | OXA-2 | SHV-11 | TEM-1 |
| 29 | KPC | | K1:CRE:KPC | KPC | | OXA-2 | wild type | wild type | K1:CRE:KPC_O2_S4_T4 | KPC-2 | | OXA-2 | SHV-11 | TEM-1 |
| 19 | KPC | | K1:CRE:KPC | KPC | | | ESBL 238/240 | wild type | K1:CRE:KPC_S1_T4 | KPC-2 | | | SHV-12 | TEM-1 |
| 30 | KPC | | K1:CRE:KPC | KPC | | | ESBL 238/240 | wild type | K1:CRE:KPC_S1_T4 | KPC-2 | | | SHV-12 | TEM-1 |
| 34 | KPC | | K1:CRE:KPC | KPC | | | wild type | wild type | K1:CRE:KPC_S4_T4 | KPC-2 | | | SHV-11 | TEM-1 |
| 31 | KPC | CTX-M-1 | K1:CRE:KPC_C1 | KPC | CTX-M-1 | OXA-50 | wild type | wild type | K1:CRE:KPC_C1 | KPC-2 | CTX-M-15 | OXA-50 | SHV-28 | TEM-1 |

FIG. 7

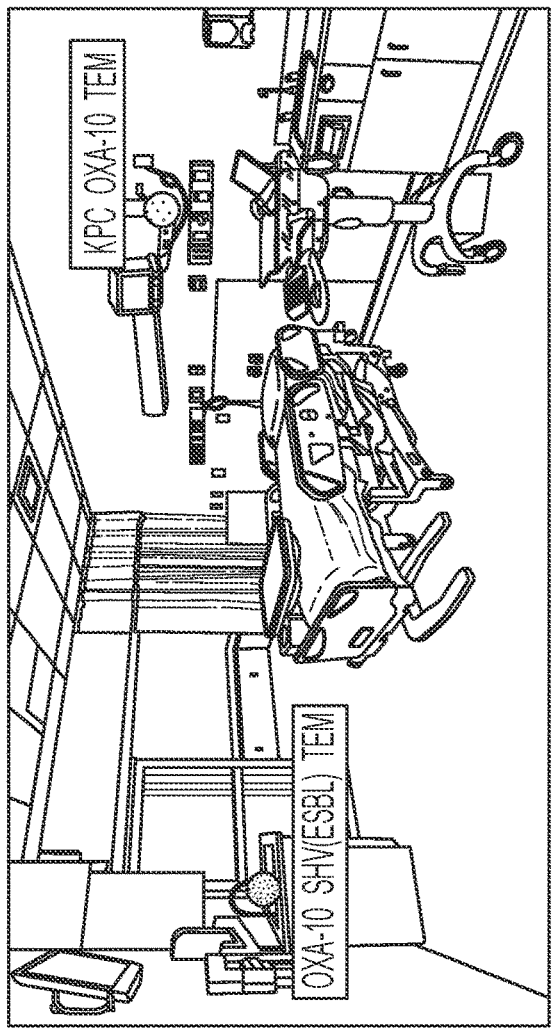
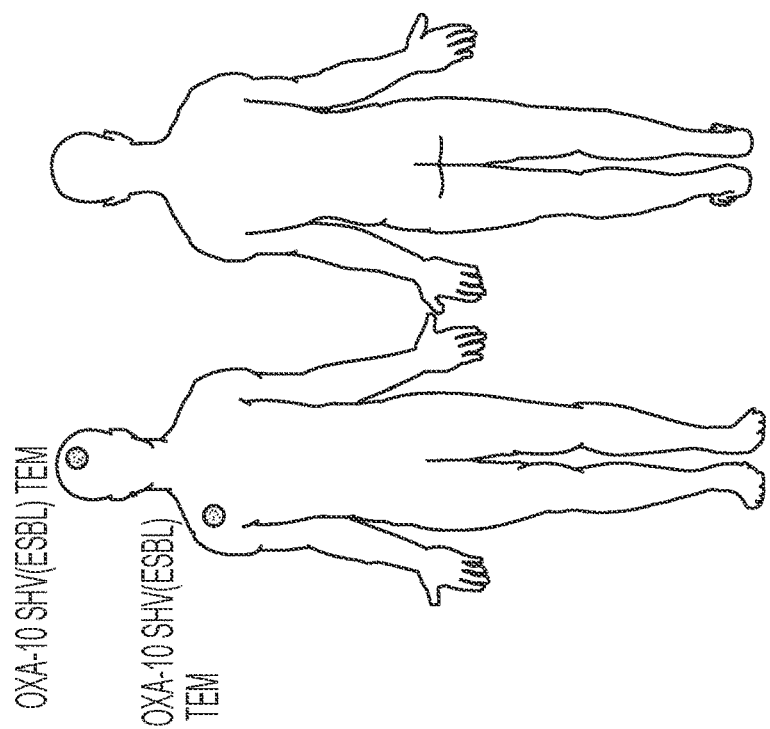
FIG. 8

SEQUENCE LISTING

<160> NUMBER OF SEQ ID NOS: 291

<210> SEQ ID NO 1
<211> LENGTH: 494
<212> TYPE: DNA
<213> ORGANISM: Artificial Sequence
<220> FEATURE:
<223> OTHER INFORMATION: Synthetic Nucleic Acid

<400> SEQUENCE: 1

| | | | | | |
|---|---|---|---|---|---|
| gattgccacg | cattgagcta | gcgagtcagc | gataagcatg | acgcgctttc | aagcgtcgcg | 60 |
| agtatgtgaa | ccaaggctcc | ggacaggact | atatacttgg | gtttgatctc | gccccgacaa | 120 |
| gaacgggatt | gactgtttga | cactagctgg | tgttcggttc | ggtaacggag | aatctgtggg | 180 |
| gctatgtcac | taatactttc | gaaacgcccc | gtaccgatgc | tgaacaagtc | gatgcaggct | 240 |
| ggatgagtgt | gacggagtgt | aactcgatga | gttacccgct | aatcgaactg | ggcgagagat | 300 |
| cccagcgctg | atgcactcga | tcccgaggcc | tgacccgaca | tatcagctca | gactagagcg | 360 |
| ggctgcgcat | aagcaaatga | caattaacca | ctgtgtactc | gttataacat | ctggcagtta | 420 |
| aagtcgggag | aataggagcc | gcaatacaca | gtttaccgca | tctagaccta | actgagatac | 480 |
| tgccatagac | gact | | | | | 494 |

<210> SEQ ID NO 2
<211> LENGTH: 23
<212> TYPE: DNA
<213> ORGANISM: Artificial Sequence
<220> FEATURE:
<223> OTHER INFORMATION: Synthetic Nucleic Acid

<400> SEQUENCE: 2
ggaaccattc gctaaactcg aac          23

<210> SEQ ID NO 3
<211> LENGTH: 20
<212> TYPE: DNA
<213> ORGANISM: Artificial Sequence
<220> FEATURE:
<223> OTHER INFORMATION: Synthetic Nucleic Acid

<400> SEQUENCE: 3
aatgagctgc acagtgggaa          20

<210> SEQ ID NO 4
<211> LENGTH: 20
<212> TYPE: DNA
<213> ORGANISM: Artificial Sequence
<220> FEATURE:
<223> OTHER INFORMATION: Synthetic Nucleic Acid

<400> SEQUENCE: 4
cggccacacc agtgacaata          20

<210> SEQ ID NO 5
<211> LENGTH: 19
<212> TYPE: DNA
<213> ORGANISM: Artificial Sequence
<220> FEATURE:
<223> OTHER INFORMATION: Synthetic Nucleic Acid

<400> SEQUENCE: 5
tgctcagtgt cggcatcac          19

```
<210> SEQ ID NO 6
<211> LENGTH: 21
<212> TYPE: DNA
<213> ORGANISM: Artificial Sequence
<220> FEATURE:
<223> OTHER INFORMATION: Synthetic Nucleic Acid

<400> SEQUENCE: 6
ccacgcattc tctagaagga c                                        21

<210> SEQ ID NO 7
<211> LENGTH: 20
<212> TYPE: DNA
<213> ORGANISM: Artificial Sequence
<220> FEATURE:
<223> OTHER INFORMATION: Synthetic Nucleic Acid

<400> SEQUENCE: 7
gctgacggga cgtatacaac                                          20

<210> SEQ ID NO 8
<211> LENGTH: 21
<212> TYPE: DNA
<213> ORGANISM: Artificial Sequence
<220> FEATURE:
<223> OTHER INFORMATION: Synthetic Nucleic Acid

<400> SEQUENCE: 8
ccacgcactc tctagaagga c                                        21

<210> SEQ ID NO 9
<211> LENGTH: 20
<212> TYPE: DNA
<213> ORGANISM: Artificial Sequence
<220> FEATURE:
<223> OTHER INFORMATION: Synthetic Nucleic Acid

<400> SEQUENCE: 9
gcagacggga cgtacacaac                                          20

<210> SEQ ID NO 10
<211> LENGTH: 22
<212> TYPE: DNA
<213> ORGANISM: Artificial Sequence
<220> FEATURE:
<223> OTHER INFORMATION: Synthetic Nucleic Acid

<400> SEQUENCE: 10
gaacgggatt gactgtttga ca                                       22

<210> SEQ ID NO 11
<211> LENGTH: 20
<212> TYPE: DNA
<213> ORGANISM: Artificial Sequence
<220> FEATURE:
<223> OTHER INFORMATION: Synthetic Nucleic Acid

<400> SEQUENCE: 11
agcctgcatc gacttgttca                                          20

<210> SEQ ID NO 12
<211> LENGTH: 19
<212> TYPE: DNA
<213> ORGANISM: Artificial Sequence
<220> FEATURE:
<223> OTHER INFORMATION: Synthetic Nucleic Acid
```

<400> SEQUENCE: 12 tggttggggga tgggatgta                                               19

<210> SEQ ID NO 13
<211> LENGTH: 23
<212> TYPE: DNA
<213> ORGANISM: Artificial Sequence
<220> FEATURE:
<223> OTHER INFORMATION: Synthetic Nucleic Acid

<400> SEQUENCE: 13
tttcgaacag agctaggtat tcc                                           23

<210> SEQ ID NO 14
<211> LENGTH: 20
<212> TYPE: DNA
<213> ORGANISM: Artificial Sequence
<220> FEATURE:
<223> OTHER INFORMATION: Synthetic Nucleic Acid

<400> SEQUENCE: 14
gccgcgcaaa tacagaatat                                               20

<210> SEQ ID NO 15
<211> LENGTH: 20
<212> TYPE: DNA
<213> ORGANISM: Artificial Sequence
<220> FEATURE:
<223> OTHER INFORMATION: Synthetic Nucleic Acid

<400> SEQUENCE: 15
accttttctc gcccttccat                                               20

<210> SEQ ID NO 16
<211> LENGTH: 23
<212> TYPE: DNA
<213> ORGANISM: Artificial Sequence
<220> FEATURE:
<223> OTHER INFORMATION: Synthetic Nucleic Acid

<400> SEQUENCE: 16
agcaaaggaa tggcaagaaa aca                                           23

<210> SEQ ID NO 17
<211> LENGTH: 19
<212> TYPE: DNA
<213> ORGANISM: Artificial Sequence
<220> FEATURE:
<223> OTHER INFORMATION: Synthetic Nucleic Acid

<400> SEQUENCE: 17
gcttggttcg cccgtttaa                                                19

<210> SEQ ID NO 18
<211> LENGTH: 22
<212> TYPE: DNA
<213> ORGANISM: Artificial Sequence
<220> FEATURE:
<223> OTHER INFORMATION: Synthetic Nucleic Acid
<220> FEATURE:
<221> NAME/KEY: misc_feature
<222> LOCATION: (3)..(3)
<223> OTHER INFORMATION: "R" is G or A
<220> FEATURE:
<221> NAME/KEY: misc_feature
<222> LOCATION: (6)..(6)
<223> OTHER INFORMATION: "R" is G or A

```
<220> FEATURE:
<221> NAME/KEY: misc_feature
<222> LOCATION: (14)..(14)
<223> OTHER INFORMATION: "M" is A or C

<400> SEQUENCE: 18
ccrggrcaca ctcmagataa cy                                                  22

<210> SEQ ID NO 19
<211> LENGTH: 24
<212> TYPE: DNA
<213> ORGANISM: Artificial Sequence
<220> FEATURE:
<223> OTHER INFORMATION: Synthetic Nucleic Acid
<220> FEATURE:
<221> NAME/KEY: misc_feature
<222> LOCATION: (4)..(4)
<223> OTHER INFORMATION: "W" is A or T
<220> FEATURE:
<221> NAME/KEY: misc_feature
<222> LOCATION: (13)..(13)
<223> OTHER INFORMATION: "W" is A or T
<220> FEATURE:
<221> NAME/KEY: misc_feature
<222> LOCATION: (24)..(24)
<223> OTHER INFORMATION: "Y" is C or T

<400> SEQUENCE: 19
gccawgcttc tawatttgcg tcay                                                24

<210> SEQ ID NO 20
<211> LENGTH: 23
<212> TYPE: DNA
<213> ORGANISM: Artificial Sequence
<220> FEATURE:
<223> OTHER INFORMATION: Synthetic Nucleic Acid

<400> SEQUENCE: 20
aaatacgagc cgttatacat tgg                                                 23

<210> SEQ ID NO 21
<211> LENGTH: 20
<212> TYPE: DNA
<213> ORGANISM: Artificial Sequence
<220> FEATURE:
<223> OTHER INFORMATION: Synthetic Nucleic Acid

<400> SEQUENCE: 21
tttatccggc gagagtacag                                                     20

<210> SEQ ID NO 22
<211> LENGTH: 22
<212> TYPE: DNA
<213> ORGANISM: Artificial Sequence
<220> FEATURE:
<223> OTHER INFORMATION: Synthetic Nucleic Acid

<400> SEQUENCE: 22
gctgtgttaa tcaatgccac ac                                                  22

<210> SEQ ID NO 23
<211> LENGTH: 20
<212> TYPE: DNA
<213> ORGANISM: Artificial Sequence
<220> FEATURE:
<223> OTHER INFORMATION: Synthetic Nucleic Acid

<400> SEQUENCE: 23
```
cgtcacgctg ttgttaggaa                                              20

<210> SEQ ID NO 24
<211> LENGTH: 22
<212> TYPE: DNA
<213> ORGANISM: Artificial Sequence
<220> FEATURE:
<223> OTHER INFORMATION: Synthetic Nucleic Acid

<400> SEQUENCE: 24
gcgacctggt taactacaat cc                                            22

<210> SEQ ID NO 25
<211> LENGTH: 24
<212> TYPE: DNA
<213> ORGANISM: Artificial Sequence
<220> FEATURE:
<223> OTHER INFORMATION: Synthetic Nucleic Acid

<400> SEQUENCE: 25
gcaatcagct tattcatggc agta                                          24

<210> SEQ ID NO 26
<211> LENGTH: 19
<212> TYPE: DNA
<213> ORGANISM: Artificial Sequence
<220> FEATURE:
<223> OTHER INFORMATION: Synthetic Nucleic Acid

<400> SEQUENCE: 26
aggactttgg cggctccat                                                19

<210> SEQ ID NO 27
<211> LENGTH: 23
<212> TYPE: DNA
<213> ORGANISM: Artificial Sequence
<220> FEATURE:
<223> OTHER INFORMATION: Synthetic Nucleic Acid

<400> SEQUENCE: 27
ctcagcgcgg taacttacag ttg                                           23

<210> SEQ ID NO 28
<211> LENGTH: 18
<212> TYPE: DNA
<213> ORGANISM: Artificial Sequence
<220> FEATURE:
<223> OTHER INFORMATION: Synthetic Nucleic Acid

<400> SEQUENCE: 28
gatcgacggc accgacat                                                 18

<210> SEQ ID NO 29
<211> LENGTH: 19
<212> TYPE: DNA
<213> ORGANISM: Artificial Sequence
<220> FEATURE:
<223> OTHER INFORMATION: Synthetic Nucleic Acid

<400> SEQUENCE: 29
cgagattgcc gagcgactt                                                19

<210> SEQ ID NO 30
<211> LENGTH: 16
<212> TYPE: DNA
<213> ORGANISM: Artificial Sequence

```
<220> FEATURE:
<223> OTHER INFORMATION: Synthetic Nucleic Acid

<400> SEQUENCE: 30
gtgcgcttcg gtccag                                                  16

<210> SEQ ID NO 31
<211> LENGTH: 19
<212> TYPE: DNA
<213> ORGANISM: Artificial Sequence
<220> FEATURE:
<223> OTHER INFORMATION: Synthetic Nucleic Acid

<400> SEQUENCE: 31
cagattgtcg gtcgaatgc                                               19

<210> SEQ ID NO 32
<211> LENGTH: 19
<212> TYPE: DNA
<213> ORGANISM: Artificial Sequence
<220> FEATURE:
<223> OTHER INFORMATION: Synthetic Nucleic Acid

<400> SEQUENCE: 32
taagttgtcg gtcgaatgc                                               19

<210> SEQ ID NO 33
<211> LENGTH: 20
<212> TYPE: DNA
<213> ORGANISM: Artificial Sequence
<220> FEATURE:
<223> OTHER INFORMATION: Synthetic Nucleic Acid

<400> SEQUENCE: 33
acccacaagt aggctggtta                                              20

<210> SEQ ID NO 34
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 34
tttctaagtt aagggagaac gctac                                        25

<210> SEQ ID NO 35
<211> LENGTH: 18
<212> TYPE: DNA
<213> ORGANISM: Artificial Sequence
<220> FEATURE:
<223> OTHER INFORMATION: Synthetic Nucleic Acid

<400> SEQUENCE: 35
gtgccagcct ctacattt                                                18

<210> SEQ ID NO 36
<211> LENGTH: 24
<212> TYPE: DNA
<213> ORGANISM: Artificial Sequence
<220> FEATURE:
<223> OTHER INFORMATION: Synthetic Nucleic Acid

<400> SEQUENCE: 36
tcattaatat ccgtttctg gttc                                          24
```

```
<210> SEQ ID NO 37
<211> LENGTH: 23
<212> TYPE: DNA
<213> ORGANISM: Artificial Sequence
<220> FEATURE:
<223> OTHER INFORMATION: Synthetic Nucleic Acid

<400> SEQUENCE: 37
agttggaatg ctcactttac tga                                      23

<210> SEQ ID NO 38
<211> LENGTH: 24
<212> TYPE: DNA
<213> ORGANISM: Artificial Sequence
<220> FEATURE:
<223> OTHER INFORMATION: Synthetic Nucleic Acid

<400> SEQUENCE: 38
ggtaaatcct tgctgcttat tctc                                     24

<210> SEQ ID NO 39
<211> LENGTH: 21
<212> TYPE: DNA
<213> ORGANISM: Artificial Sequence
<220> FEATURE:
<223> OTHER INFORMATION: Synthetic Nucleic Acid
<220> FEATURE:
<221> NAME/KEY: misc_feature
<222> LOCATION: (13)..(13)
<223> OTHER INFORMATION: "Y" is C or T
<220> FEATURE:
<221> NAME/KEY: misc_feature
<222> LOCATION: (15)..(15)
<223> OTHER INFORMATION: "R" is G or A

<400> SEQUENCE: 39
gtagtggttt ggytrcctga a                                        21

<210> SEQ ID NO 40
<211> LENGTH: 24
<212> TYPE: DNA
<213> ORGANISM: Artificial Sequence
<220> FEATURE:
<223> OTHER INFORMATION: Synthetic Nucleic Acid
<220> FEATURE:
<221> NAME/KEY: misc_feature
<222> LOCATION: (14)..(14)
<223> OTHER INFORMATION: "Y" is C or T
<220> FEATURE:
<221> NAME/KEY: misc_feature
<222> LOCATION: (18)..(18)
<223> OTHER INFORMATION: "R" is G or A

<400> SEQUENCE: 40
ccgtacggtt taayaaarca acca                                     24

<210> SEQ ID NO 41
<211> LENGTH: 30
<212> TYPE: DNA
<213> ORGANISM: Artificial Sequence
<220> FEATURE:
<223> OTHER INFORMATION: Synthetic Nucleic Acid

<400> SEQUENCE: 41
aattacgaaa tctggtgtat ggaaaatgtg                               30

<210> SEQ ID NO 42
<211> LENGTH: 27
```

```
<212> TYPE: DNA
<213> ORGANISM: Artificial Sequence
<220> FEATURE:
<223> OTHER INFORMATION: Synthetic Nucleic Acid

<400> SEQUENCE: 42
ctgaatagca attgtcgttt tcccatt                                            27

<210> SEQ ID NO 43
<211> LENGTH: 17
<212> TYPE: DNA
<213> ORGANISM: Artificial Sequence
<220> FEATURE:
<223> OTHER INFORMATION: Synthetic Nucleic Acid
<220> FEATURE:
<221> NAME/KEY: misc_feature
<222> LOCATION: (6)..(6)
<223> OTHER INFORMATION: "K" is G or T

<400> SEQUENCE: 43
agtctkcctc ccgactg                                                       17

<210> SEQ ID NO 44
<211> LENGTH: 16
<212> TYPE: DNA
<213> ORGANISM: Artificial Sequence
<220> FEATURE:
<223> OTHER INFORMATION: Synthetic Nucleic Acid

<400> SEQUENCE: 44
gcaaacggcg gacgta                                                        16

<210> SEQ ID NO 45
<211> LENGTH: 18
<212> TYPE: DNA
<213> ORGANISM: Artificial Sequence
<220> FEATURE:
<223> OTHER INFORMATION: Synthetic Nucleic Acid

<400> SEQUENCE: 45
ttgcggagaa acacgtta                                                      18

<210> SEQ ID NO 46
<211> LENGTH: 16
<212> TYPE: DNA
<213> ORGANISM: Artificial Sequence
<220> FEATURE:
<223> OTHER INFORMATION: Synthetic Nucleic Acid

<400> SEQUENCE: 46
gctatactgc agcgcc                                                        16

<210> SEQ ID NO 47
<211> LENGTH: 20
<212> TYPE: DNA
<213> ORGANISM: Artificial Sequence
<220> FEATURE:
<223> OTHER INFORMATION: Synthetic Nucleic Acid

<400> SEQUENCE: 47
gctggtgttc ggttcggtaa                                                    20

<210> SEQ ID NO 48
<211> LENGTH: 18
<212> TYPE: DNA
<213> ORGANISM: Artificial Sequence
<220> FEATURE:
```

<223> OTHER INFORMATION: Synthetic Nucleic Acid

<400> SEQUENCE: 48
catcggtacg gggcgttt                                                  18

<210> SEQ ID NO 49
<211> LENGTH: 16
<212> TYPE: DNA
<213> ORGANISM: Artificial Sequence
<220> FEATURE:
<223> OTHER INFORMATION: Synthetic Nucleic Acid

<400> SEQUENCE: 49
tatccatcgc gtacac                                                    16

<210> SEQ ID NO 50
<211> LENGTH: 14
<212> TYPE: DNA
<213> ORGANISM: Artificial Sequence
<220> FEATURE:
<223> OTHER INFORMATION: Synthetic Nucleic Acid

<400> SEQUENCE: 50
tcaaggacag caag                                                      14

<210> SEQ ID NO 51
<211> LENGTH: 14
<212> TYPE: DNA
<213> ORGANISM: Artificial Sequence
<220> FEATURE:
<223> OTHER INFORMATION: Synthetic Nucleic Acid

<400> SEQUENCE: 51
cagcaccagg atag                                                      14

<210> SEQ ID NO 52
<211> LENGTH: 14
<212> TYPE: DNA
<213> ORGANISM: Artificial Sequence
<220> FEATURE:
<223> OTHER INFORMATION: Synthetic Nucleic Acid

<400> SEQUENCE: 52
cagcaccggg atag                                                      14

<210> SEQ ID NO 53
<211> LENGTH: 14
<212> TYPE: DNA
<213> ORGANISM: Artificial Sequence
<220> FEATURE:
<223> OTHER INFORMATION: Synthetic Nucleic Acid

<400> SEQUENCE: 53
ccacagattc tccg                                                      14

<210> SEQ ID NO 54
<211> LENGTH: 14
<212> TYPE: DNA
<213> ORGANISM: Artificial Sequence
<220> FEATURE:
<223> OTHER INFORMATION: Synthetic Nucleic Acid

<400> SEQUENCE: 54
ttgaggctga acaa                                                      14

<210> SEQ ID NO 55
<211> LENGTH: 14
<212> TYPE: DNA
<213> ORGANISM: Artificial Sequence
<220> FEATURE:
<223> OTHER INFORMATION: Synthetic Nucleic Acid

<400> SEQUENCE: 55
ccctgatcgg attg                                                         14

<210> SEQ ID NO 56
<211> LENGTH: 15
<212> TYPE: DNA
<213> ORGANISM: Artificial Sequence
<220> FEATURE:
<223> OTHER INFORMATION: Synthetic Nucleic Acid

<400> SEQUENCE: 56
ctacgccctg tgatt                                                        15

<210> SEQ ID NO 57
<211> LENGTH: 18
<212> TYPE: DNA
<213> ORGANISM: Artificial Sequence
<220> FEATURE:
<223> OTHER INFORMATION: Synthetic Nucleic Acid

<400> SEQUENCE: 57
ccgaataata ttttcctt                                                     18

<210> SEQ ID NO 58
<211> LENGTH: 17
<212> TYPE: DNA
<213> ORGANISM: Artificial Sequence
<220> FEATURE:
<223> OTHER INFORMATION: Synthetic Nucleic Acid

<400> SEQUENCE: 58
ccgaataaaa ttttctt                                                      17

<210> SEQ ID NO 59
<211> LENGTH: 16
<212> TYPE: DNA
<213> ORGANISM: Artificial Sequence
<220> FEATURE:
<223> OTHER INFORMATION: Synthetic Nucleic Acid

<400> SEQUENCE: 59
ccgcgcaagg tttttc                                                       16

<210> SEQ ID NO 60
<211> LENGTH: 14
<212> TYPE: DNA
<213> ORGANISM: Artificial Sequence
<220> FEATURE:
<223> OTHER INFORMATION: Synthetic Nucleic Acid

<400> SEQUENCE: 60
cggcaagttt ttgc                                                         14

<210> SEQ ID NO 61
<211> LENGTH: 13
<212> TYPE: DNA
<213> ORGANISM: Artificial Sequence
<220> FEATURE:
<223> OTHER INFORMATION: Synthetic Nucleic Acid

```
<400> SEQUENCE: 61
ccaagctcag cca                                                          13

<210> SEQ ID NO 62
<211> LENGTH: 18
<212> TYPE: DNA
<213> ORGANISM: Artificial Sequence
<220> FEATURE:
<223> OTHER INFORMATION: Synthetic Nucleic Acid
<220> FEATURE:
<221> NAME/KEY: misc_feature
<222> LOCATION: (1)..(1)
<223> OTHER INFORMATION: "K" is G or T
<220> FEATURE:
<221> NAME/KEY: misc_feature
<222> LOCATION: (7)..(7)
<223> OTHER INFORMATION: "K" is G or T

<400> SEQUENCE: 62
kagtctkcct cccgactg                                                     18

<210> SEQ ID NO 63
<211> LENGTH: 121
<212> TYPE: DNA
<213> ORGANISM: Artificial Sequence
<220> FEATURE:
<223> OTHER INFORMATION: Synthetic Nucleic Acid
<220> FEATURE:
<221> NAME/KEY: misc_feature
<222> LOCATION: (30)..(30)
<223> OTHER INFORMATION: "K" is G or T

<400> SEQUENCE: 63
gctgtgttaa tcaatgccac acccagtctk cctcccgact gccgctctaa ttcggcaagt       60
ttttgctgta cgtccgccgt tttgcgcata cagcggcaca cttcctaaca acagcgtgac      120
g                                                                      121

<210> SEQ ID NO 64
<211> LENGTH: 119
<212> TYPE: DNA
<213> ORGANISM: Artificial Sequence
<220> FEATURE:
<223> OTHER INFORMATION: Synthetic Nucleic Acid

<400> SEQUENCE: 64
gcgacctggt taactacaat cccattgcgg agaaacacgt taacggcacg atgacgctgg       60
ctgagcttgg cgcagcggct gcagtatagc gacaatactg ccatgaataa gctgattgc      119

<210> SEQ ID NO 65
<211> LENGTH: 120
<212> TYPE: DNA
<213> ORGANISM: Artificial Sequence
<220> FEATURE:
<223> OTHER INFORMATION: Synthetic Nucleic Acid

<400> SEQUENCE: 65
gaacgggatt gactgtttga cactagctgg tgttcggttc ggtaacggag aatctgtggg       60
gctatgtcac taatactttc gaaacgcccc gtaccgatgc tgaacaagtc gatgcaggct     120

<210> SEQ ID NO 66
<211> LENGTH: 122
<212> TYPE: DNA
<213> ORGANISM: Artificial Sequence
<220> FEATURE:
<223> OTHER INFORMATION: Synthetic Nucleic Acid
```

<400> SEQUENCE: 66
ccgggacaca ctccagataa cgtagtggtt tggttgcctg aaaggaaaat attattcggt    60
ggttgttttt attaaaccgt acggtttagg caatttgggt gacgcaaata tagaagcttg   120
gc                                                                 122

<210> SEQ ID NO 67
<211> LENGTH: 122
<212> TYPE: DNA
<213> ORGANISM: Artificial Sequence
<220> FEATURE:
<223> OTHER INFORMATION: Synthetic Nucleic Acid

<400> SEQUENCE: 67
ccggggcaca ctcaagataa cgtagtggtt tggttacctg aaaagaaaat tttattcggt    60
ggttgttttt gttaaaccgg acggtcttgg taatttgggt gacgcaaatt tagaagcttg   120
gc                                                                 122

<210> SEQ ID NO 68
<211> LENGTH: 124
<212> TYPE: DNA
<213> ORGANISM: Artificial Sequence
<220> FEATURE:
<223> OTHER INFORMATION: Synthetic Nucleic Acid

<400> SEQUENCE: 68
ggaaccattc gctaaactcg aacaggactt tggcggctcc atcggtgtgt acgcgatgga    60
taccggctca ggcgcaactg ttaagttacc gcgctgagga gcgcttccca ctgtgcagct   120
catt                                                               124

<210> SEQ ID NO 69
<211> LENGTH: 124
<212> TYPE: DNA
<213> ORGANISM: Artificial Sequence
<220> FEATURE:
<223> OTHER INFORMATION: Synthetic Nucleic Acid

<400> SEQUENCE: 69
cggccacacc agtgacaata tcaccgttgg gatcgacggc accgacatcg cttttggtgg    60
ctgcctgatc aaggacagca agggccaagt cgctcggcaa tctcggtgat gccgacactg   120
agca                                                               124

<210> SEQ ID NO 70
<211> LENGTH: 120
<212> TYPE: DNA
<213> ORGANISM: Artificial Sequence
<220> FEATURE:
<223> OTHER INFORMATION: Synthetic Nucleic Acid

<400> SEQUENCE: 70
gccgcgcaaa tacagaatat gtgccagcct ctacatttaa aatgttgaat gccctgatcg    60
gattggagaa ccagaaaacg gatattaatg aaatatttaa atggaagggc gagaaaaggt   120

<210> SEQ ID NO 71
<211> LENGTH: 133
<212> TYPE: DNA
<213> ORGANISM: Artificial Sequence
<220> FEATURE:
<223> OTHER INFORMATION: Synthetic Nucleic Acid -continued

<400> SEQUENCE: 71
agcaaaggaa tggcaagaaa acaaaagttg gaatgctcac tttactgaac ataaatcaca    60
gggcgtagtt gtgctctgga aatgagaata agcagcaagg atttaccaat aatcttaaac   120
gggcgaacca agc                                                     133

<210> SEQ ID NO 72
<211> LENGTH: 129
<212> TYPE: DNA
<213> ORGANISM: Artificial Sequence
<220> FEATURE:
<223> OTHER INFORMATION: Synthetic Nucleic Acid

<400> SEQUENCE: 72
tggttgggga tgggatgtag acccacaagt aggctggtta actggatggg ttgttcagcc    60
tcaaggaaat attgtagcgt tctcccttaa cttagaaatg aaaaaggaa tacctagctc    120 tgttcgaaa                                                          129

<210> SEQ ID NO 73
<211> LENGTH: 118
<212> TYPE: DNA
<213> ORGANISM: Artificial Sequence
<220> FEATURE:
<223> OTHER INFORMATION: Synthetic Nucleic Acid

<400> SEQUENCE: 73
aaatacgagc cgttatacat tggaattacg aaatctggtg tatggaaaat gtgcgaaaaa    60
ccttgcgcgg aatgggaaaa acgacaattg ctattcagct gtactctcgc cggataaa    118

<210> SEQ ID NO 74
<211> LENGTH: 122
<212> TYPE: DNA
<213> ORGANISM: Artificial Sequence
<220> FEATURE:
<223> OTHER INFORMATION: Synthetic Nucleic Acid

<400> SEQUENCE: 74
ccacgcattc tctagaagga ctctcatcga gcggggacgc agtgcgcttc ggtccagtag    60
agctcttcta tcctggtgct gcggcattcg accgacaatc tggttgtata cgtcccgtca   120
gc                                                                 122

<210> SEQ ID NO 75
<211> LENGTH: 122
<212> TYPE: DNA
<213> ORGANISM: Artificial Sequence
<220> FEATURE:
<223> OTHER INFORMATION: Synthetic Nucleic Acid

<400> SEQUENCE: 75
ccacgcactc tctagaagga ctctcatcga gcggggacgc agtgcgcttc ggtccagtag    60
agctcttcta tcctggtgct gcggcattcg accgacaact tagttgtgta cgtcccgtct   120
gc                                                                 122

<210> SEQ ID NO 76
<211> LENGTH: 122
<212> TYPE: DNA
<213> ORGANISM: Artificial Sequence
<220> FEATURE:
<223> OTHER INFORMATION: Synthetic Nucleic Acid

<400> SEQUENCE: 76

```
ccacgcactc tctagaagga ctctcatcga gcggggacgc agtgcgcttc ggtccagtag      60
agctcttcta tcccggtgct gcggcattcg accgacaatc tggttgtata cgtcccgtca     120
gc                                                                    122
```

<210> SEQ ID NO 77
<211> LENGTH: 372
<212> TYPE: DNA
<213> ORGANISM: Artificial Sequence
<220> FEATURE:
<223> OTHER INFORMATION: Synthetic Nucleic Acid

<400> SEQUENCE: 77

```
ggaaccattc gctaaactcg aacaggactt tggcggctcc atcggtgtgt acgcgatgga      60
taccggctca ggcgcaactg taagttaccg cgctgaggag cgcttcccac tgtgcagctc     120
atttggttgg ggatgggatg tagacccaca gtaggctgg ttaactggat gggttgttca     180
gcctcaagga atattgtag cgttctccct taacttagaa atgaaaaaag gaatacctag     240
ctctgttcga aagctgtgtt aatcaatgcc acacccagtc tgcctcccga ctgccgctct     300
aattcggcaa gttttttgctg tacgtccgcc gtttgcgcat acagcggcac acttcctaac    360
aacagcgtga cg                                                         372
```

<210> SEQ ID NO 78
<211> LENGTH: 367
<212> TYPE: DNA
<213> ORGANISM: Artificial Sequence
<220> FEATURE:
<223> OTHER INFORMATION: Synthetic Nucleic Acid

<400> SEQUENCE: 78

```
ggatcaagca ggagatcaac ctgccggtcg cgctggcggt ggtgactcac gcgcatcagg      60
acaagatggg cggtatggac gcgctgcatg cggcggggat tgcgacttat gccaatgcgt     120
tgtcgagccg cgcaaataca gaatatgtgc cagcctctac atttaaaatg ttgaatgccc     180
tgatcggatt ggagaaccag aaaacgata ttaatgaaat attaaatgg aagggcgaga     240 aaaggtgcga cctggttaac tacaatccca ttgcggagaa acacgttaac ggcacgatga     300
cgctggctga gcttggcgca gcggcgctgc agtatagcga caatactgcc atgaataagc     360
tgattgc                                                               367
```

<210> SEQ ID NO 79
<211> LENGTH: 364
<212> TYPE: DNA
<213> ORGANISM: Artificial Sequence
<220> FEATURE:
<223> OTHER INFORMATION: Synthetic Nucleic Acid

<400> SEQUENCE: 79

```
cggccacacc agtgacaata tcaccgttgg gatcgacggc accgacatcg cttttggtgg      60
ctgcctgatc aaggacagca aggccaagtc gctcggcaat ctcggtgatg ccgacactga     120
gcagccgcgc aaatacagaa tatgtgccag cctctacatt taaaatgttg aatgccctga     180
tcggattgga gaaccagaaa acggatatta atgaaatatt taaatggaag ggcgagaaaa     240
ggtgcgacct ggttaactac aatcccattg cggagaaaca cgttaacggc acgatgacgc     300
tggctgagct tggcgcagcg gcgctgcagt atagcgacaa tactgccatg aataagctga     360
ttgc                                                                  364
```

<210> SEQ ID NO 80
<211> LENGTH: 373
<212> TYPE: DNA
<213> ORGANISM: Artificial Sequence
<220> FEATURE:
<223> OTHER INFORMATION: Synthetic Nucleic Acid

<400> SEQUENCE: 80

```
ccacgcattc tctagaagga ctctcatcga gcggggacgc agtgcgcttc ggtccagtag      60
agctcttcta tcctggtgct gcgcattcga ccgacaatct ggttgtatac gtcccgtcag     120
cagcaaagga atggcaagaa aacaaaagtt ggaatgctca ctttactgaa cataaatcac     180
agggcgtagt tgtgctctgg aatgagaata agcagcaagg atttaccaat aatcttaaac     240
gggcgaacca agccactggg gccagatggt aagccctccc gtatcgtagt tatctacacg     300
acggggagtc aggcaactat ggatgaacga aatagacaga tcgctgagat aggtgcctca     360
ctgattaagc att                                                        373
```

<210> SEQ ID NO 81
<211> LENGTH: 241
<212> TYPE: DNA
<213> ORGANISM: Artificial Sequence
<220> FEATURE:
<223> OTHER INFORMATION: Synthetic Nucleic Acid

<400> SEQUENCE: 81

```
aaatacgagc cgttatacat tggaattacg aaatctggtg tatggaaaat gtgcgaaaaa      60
ccttgcgcgg aatgggaaaa cgacaattgc tattcagctg tactctcgcc ggataaagcc     120
gatgaacgct ttcccatgat gagcaccttt aaagtagtgc tctgcggcgc agtgctggcg     180
cgggtggatg ccggtgacga acagctggag cgaaagatcc actatcgcca gcaggatctg     240
g                                                                     241
```

<210> SEQ ID NO 82
<211> LENGTH: 266
<212> TYPE: DNA
<213> ORGANISM: Artificial Sequence
<220> FEATURE:
<223> OTHER INFORMATION: Synthetic Nucleic Acid

<400> SEQUENCE: 82

```
ccgggacaca ctccagataa cgtagtggtt tggttgcctg aaaggaaaat attattcggt      60
ggttgtttta ttaaaccgta cggtttaggc aatttgggtg acgcaaatat agaagcttgg     120
ccttacctac cctgtctttg tgaagccggc acggtcaggt tcgtcctttg gcttaaccaa     180
agtaaacggt acggaagaac ttaacgctgc gatagaagcg gcaggacaat atgatggaaa     240
aatcttaatt gagcaagcga tttcgg                                          266
```

<210> SEQ ID NO 83
<211> LENGTH: 392
<212> TYPE: DNA
<213> ORGANISM: Artificial Sequence
<220> FEATURE:
<223> OTHER INFORMATION: Synthetic Nucleic Acid

<400> SEQUENCE: 83

```
ggatcaagca ggagatcaac ctgccggtcg cgctggcggt ggtgactcac gcgcatcagg      60
acaagatggg cggtatgaac gcgctgcatg cggcggggat tgcgacttat gccaatgcgt     120
tgtcgaccgg ggcacactca agataacgta gtggtttggt tacctgaaaa gaaaatttta     180
```

```
ttcggtggtt gttttgttaa accggacggt cttggtaatt tgggtgacgc aaatttagaa      240
gcttggcctt acctaccctg tctttgtgaa gccggcacgg tcaggttcgt cctttggcgt      300
aaccaaagta aacagtacgg aagaactaaa cgctgcgata gaagcagcag gacaatatga      360
tggaaaaatc ttaattgagc aagcgatttc gg                                    392

<210> SEQ ID NO 84
<211> LENGTH: 247
<212> TYPE: DNA
<213> ORGANISM: Artificial Sequence
<220> FEATURE:
<223> OTHER INFORMATION: Synthetic Nucleic Acid

<400> SEQUENCE: 84
ggatcaagca ggagatcaac ctgccggtcg cgctggcggt ggtgactcac gcgcatcagg       60
acaagatggg cggtatgggc gcgctgcatg cggcgggat tgcgacttat gccaatgcgt      120
tgtcgaccag gtcacactca agataaccta gtggtttggt tgcctgaaag taaaatttta     180
ttcggtggtt gctttattaa acctcacggt cttggcaatt taggtgacgc aaatttagaa     240
gcttggc                                                               247

<210> SEQ ID NO 85
<211> LENGTH: 266
<212> TYPE: DNA
<213> ORGANISM: Artificial Sequence
<220> FEATURE:
<223> OTHER INFORMATION: Synthetic Nucleic Acid

<400> SEQUENCE: 85
ccacgcactc tctagaagga ctctcatcga gcggggacgc agtgcgcttc ggtccagtag       60
agctcttcta tcctggtgct gcgcattcga ccgacaactt agttgtgtac gtcccgtctg     120
ccttacctac cctgtctttg tgaagccggc acggtcaggt tcgtcctttg gcgtaaccaa     180
agtaaacagt acggaagaac taaacgctgc gatagaagca gcaggacaat atgatggaaa     240
aatcttaatt gagcaagcga tttcgg                                          266

<210> SEQ ID NO 86
<211> LENGTH: 247
<212> TYPE: DNA
<213> ORGANISM: Artificial Sequence
<220> FEATURE:
<223> OTHER INFORMATION: Synthetic Nucleic Acid

<400> SEQUENCE: 86
ggatcaagca ggagatcaac ctgccggtcg cgctggcggt ggtgactcac gcgcatcagg       60
acaagatggg cggtatgaac gcgctgcatg cggcgggat tgcgacttat gccaatgcgt      120
tgtcgaccgg ggcacactca agataacgta gtggtttggt tacctgaaaa gaaaatttta     180
ttcggtggtt gttttgttaa accggacggt cttggtaatt tgggtgacgc aaatttagaa     240
gcttggc                                                               247

<210> SEQ ID NO 87
<211> LENGTH: 242
<212> TYPE: DNA
<213> ORGANISM: Artificial Sequence
<220> FEATURE:
<223> OTHER INFORMATION: Synthetic Nucleic Acid

<400> SEQUENCE: 87
```

```
ccacgcactc tctagaagga ctctcatcga gcggggacgc agtgcgcttc ggtccagtag      60
agctcttcta tcccggtgct gcgcattcga ccgacaatct ggttgtatac gtcccgtcag     120
cggatgagtg tgacggagtg taactcgatg agttacccgc taatcgaact gggcgagaga     180
tcccagcgct gatgcactcg atcccgaggc ctgacccgac atatcagctc agactagagc     240
gg                                                                    242
```

<210> SEQ ID NO 88
<211> LENGTH: 140
<212> TYPE: DNA
<213> ORGANISM: Artificial Sequence
<220> FEATURE:
<223> OTHER INFORMATION: Synthetic Nucleic Acid

<400> SEQUENCE: 88

```
atgcagcaaa ggaatggcaa gaaaacaaaa gttggaatgc tcactttact gaacataaat      60
cacagggcgt agttgtgctc tggaatgaga ataagcagca aggatttacc aataatctta     120
aacgggcgaa ccaagcatgc                                                 140
```

<210> SEQ ID NO 89
<211> LENGTH: 663
<212> TYPE: DNA
<213> ORGANISM: Artificial Sequence
<220> FEATURE:
<223> OTHER INFORMATION: Synthetic Nucleic Acid

<400> SEQUENCE: 89

```
caacctcgtc gcggaaccat tcgctaaact cgaacaggac tttggcggct ccatcggtgt      60
gtacgcgatg gataccggct caggcgcaac tgtaagttac cgcgctgagg agcgcttccc     120
actgtgcagc tcattcaagg gctttcttgc tgccgctgtg ctggctcgca gccagcagca     180
gcaggccggc ttgctggaca cacccatccg ttacggcaaa aatgcgctgg ttccgtggtc     240
acccatctcg gaaaaatatc tgacaacagg catgacggtg gcggagctgt ccgcggccgc     300
cgtgcaatac agtgataacg ccgccgccaa tttgttgctg aaggagttgg gcggcccggc     360
cgggctgacg gccttcatgc gctctatcgg cgataccacg ttccgtctgg accgctggga     420
gctggagctg aactccgcca tcccaggcga tgcgcgcgat acctcatcgc gcgcgccgt     480 gacggaaagc ttacaaaaac tgacactggg ctctgcactg gctgcgccgc agcggcagca     540
gtttgttgat tggctaaagg gaaacacgac cggcaaccac cgcatccgcg cggcggtgcc     600
ggcagactgg gcagtcggag acaaaaccgg aacctgcgga gtgtatggca cggcaaatga     660
cta                                                                   663
```

<210> SEQ ID NO 90
<211> LENGTH: 194
<212> TYPE: DNA
<213> ORGANISM: Artificial Sequence
<220> FEATURE:
<223> OTHER INFORMATION: Synthetic Nucleic Acid

<400> SEQUENCE: 90

```
ataaaaaaat taatttgtat ggtaatgctc taagccgcgc aaatacagaa tatgtgccag      60
cctctacatt taaaatgttg aatgccctga tcggattgga gaaccagaaa acggatatta     120
atgaaatatt taaatggaag ggcgagaaaa ggtcatttac cacttgggaa aaagacatga     180
cactaggaga agcc                                                       194
```

```
<210> SEQ ID NO 91
<211> LENGTH: 225
<212> TYPE: DNA
<213> ORGANISM: Artificial Sequence
<220> FEATURE:
<223> OTHER INFORMATION: Synthetic Nucleic Acid

<400> SEQUENCE: 91
caatccatgc tattcataga agaaaagaat ggaaacaaaa tatacgcaaa aagtggttgg      60
ggatgggatg taaacccaca agtaggctgg ttaactggat gggttgttca gcctcaaggg     120
aatattgtag cgttctccct taacttagaa atgaaaaag gaatacctag ctctgttcga      180
aaagagatta cttataaaag cttagaacaa ttaggtattt tatag                    225

<210> SEQ ID NO 92
<211> LENGTH: 212
<212> TYPE: DNA
<213> ORGANISM: Artificial Sequence
<220> FEATURE:
<223> OTHER INFORMATION: Synthetic Nucleic Acid

<400> SEQUENCE: 92
taaaatctgc aatagagata gccgctaaca ttaataaaga aaaatacgag ccgttataca      60
ttggaattac gaaatctggt gtatggaaaa tgtgcgaaaa accttgcgcg gaatgggaaa     120
acgacaattg ctattcagct gtactctcgc cggataaaaa aatgcacgga ttacttgtta     180
aaaagaacca tgaatatgaa atcaaccatg tt                                   212

<210> SEQ ID NO 93
<211> LENGTH: 205
<212> TYPE: DNA
<213> ORGANISM: Artificial Sequence
<220> FEATURE:
<223> OTHER INFORMATION: Synthetic Nucleic Acid

<400> SEQUENCE: 93
gataaaggtg acaagccgga gacgggtgcg cttacctacc ctgtctttgt gaagccggca      60
cggtcaggtt cgtcctttgg cttaaccaaa gtaaacggta cggaagaact aacgctgcg     120 atagaagcgg caggacaata tgatggaaaa atcttaattg agcaagcgat ttcgggctgt    180
gaggtcggct gtgcggttat gggga                                          205

<210> SEQ ID NO 94
<211> LENGTH: 204
<212> TYPE: DNA
<213> ORGANISM: Artificial Sequence
<220> FEATURE:
<223> OTHER INFORMATION: Synthetic Nucleic Acid

<400> SEQUENCE: 94
gaaaaaggtg acaaaccgga ggcgaggacg cttacctacc ctgtctttgt gaagccggca      60
cggtcaggtt cgtcctttgg cgtaaccaaa gtaaacagta cggaagaact aaacgctgcg    120
atagaagcag caggacaata tgatggaaaa atcttaattg agcaagcgat ttcgggctgt    180
gaggtcggct gcgcggtcat ggga                                           204

<210> SEQ ID NO 95
<211> LENGTH: 137
<212> TYPE: DNA
<213> ORGANISM: Artificial Sequence
<220> FEATURE:
<223> OTHER INFORMATION: Synthetic Nucleic Acid
<220> FEATURE:
```

```
<221> NAME/KEY: misc_feature
<222> LOCATION: (24)..(24)
<223> OTHER INFORMATION: "R" is G or A

<400> SEQUENCE: 95
atgctggttg gggatgggat gtaracccac aagtaggctg gttaactgga tgggttgttc     60
agcctcaagg aaatattgta gcgttctccc ttaacttaga aatgaaaaaa ggaataccta    120
gctctgttcg aaaatgc                                                   137

<210> SEQ ID NO 96
<211> LENGTH: 128
<212> TYPE: DNA
<213> ORGANISM: Artificial Sequence
<220> FEATURE:
<223> OTHER INFORMATION: Synthetic Nucleic Acid

<400> SEQUENCE: 96
atgcgccgcg caaatacaga atatgtgcca gcctctacat ttaaaatgtt gaatgccctg     60
atcggattgg agaaccagaa aacggatatt aatgaaatat ttaaatggaa gggcgagaaa    120
aggtatgc                                                             128

<210> SEQ ID NO 97
<211> LENGTH: 125
<212> TYPE: DNA
<213> ORGANISM: Artificial Sequence
<220> FEATURE:
<223> OTHER INFORMATION: Synthetic Nucleic Acid

<400> SEQUENCE: 97
atgcaaatac gagccgttat acattggaat tacgaaatct ggtgtatgga aatgtgcga      60 aaaaccttgc gcggaatggg aaaacgacaa ttgctattca gctgtactct cgccggataa    120
aatgc                                                                125

<210> SEQ ID NO 98
<211> LENGTH: 153
<212> TYPE: DNA
<213> ORGANISM: Artificial Sequence
<220> FEATURE:
<223> OTHER INFORMATION: Synthetic Nucleic Acid

<400> SEQUENCE: 98
atgccttacc taccctgtct ttgtgaagcc ggcacggtca ggttcgtcct ttggcgtaac     60
caaagtaaac ggtacggaag aacttaacgc tgcgatagaa gcggcaggac aatatgatgg    120
aaaaatctta attgagcaag cgatttcgga tgc                                 153

<210> SEQ ID NO 99
<211> LENGTH: 129
<212> TYPE: DNA
<213> ORGANISM: Artificial Sequence
<220> FEATURE:
<223> OTHER INFORMATION: Synthetic Nucleic Acid

<400> SEQUENCE: 99
atgcctgcgc actctctaaa agcgctctcc tctagtggag atgtggtgcg cttcggtccc     60
gtagaggttt tctatcctgg tgctgcgcat tcgggcgaca atcttgtggt atacgtgccg    120
gccgtatgc                                                            129

<210> SEQ ID NO 100
<211> LENGTH: 129
```

```
<212> TYPE: DNA
<213> ORGANISM: Artificial Sequence
<220> FEATURE:
<223> OTHER INFORMATION: Synthetic Nucleic Acid

<400> SEQUENCE: 100
atgcccacgc actctctaga aggactctca tcgagcgggg acgcggtgcg cttcggtcca    60
gtagaactct tctatcctgg tgctgcgcat tcgaccgaca acttagttgt gtacgtcccg   120
tctgcatgc                                                          129

<210> SEQ ID NO 101
<211> LENGTH: 134
<212> TYPE: DNA
<213> ORGANISM: Artificial Sequence
<220> FEATURE:
<223> OTHER INFORMATION: Synthetic Nucleic Acid

<400> SEQUENCE: 101
atgcggatca agcaggagat caacctgccg gtcgcgctgg cggtggtgac tcacgcgcat    60
caggacaaga tgggcggtat ggacgcgctg catgcggcgg ggattgcgac ttatgccaat   120
gcgttgtcga atgc                                                    134

<210> SEQ ID NO 102
<211> LENGTH: 22
<212> TYPE: DNA
<213> ORGANISM: Artificial Sequence
<220> FEATURE:
<223> OTHER INFORMATION: Synthetic Nucleic Acid
<220> FEATURE:
<221> NAME/KEY: misc_feature
<222> LOCATION: (17)..(17)
<223> OTHER INFORMATION: "K" is G or T

<400> SEQUENCE: 102
gatgagccag tgcacgksaa ta                                            22

<210> SEQ ID NO 103
<211> LENGTH: 21
<212> TYPE: DNA
<213> ORGANISM: Artificial Sequence
<220> FEATURE:
<223> OTHER INFORMATION: Synthetic Nucleic Acid

<400> SEQUENCE: 103
gtcgctggag gtggttttga t                                             21

<210> SEQ ID NO 104
<211> LENGTH: 16
<212> TYPE: DNA
<213> ORGANISM: Artificial Sequence
<220> FEATURE:
<223> OTHER INFORMATION: Synthetic Nucleic Acid

<400> SEQUENCE: 104
taagcttcgt taccca                                                   16

<210> SEQ ID NO 105
<211> LENGTH: 22
<212> TYPE: DNA
<213> ORGANISM: Artificial Sequence
<220> FEATURE:
<223> OTHER INFORMATION: Synthetic Nucleic Acid

<400> SEQUENCE: 105
```
tcgctggata aaagcattag cc                                              22

<210> SEQ ID NO 106
<211> LENGTH: 17
<212> TYPE: DNA
<213> ORGANISM: Artificial Sequence
<220> FEATURE:
<223> OTHER INFORMATION: Synthetic Nucleic Acid

<400> SEQUENCE: 106
tgcgttcccg cattcag                                                    17

<210> SEQ ID NO 107
<211> LENGTH: 14
<212> TYPE: DNA
<213> ORGANISM: Artificial Sequence
<220> FEATURE:
<223> OTHER INFORMATION: Synthetic Nucleic Acid

<400> SEQUENCE: 107
ttccagaact gcgc                                                       14

<210> SEQ ID NO 108
<211> LENGTH: 18
<212> TYPE: DNA
<213> ORGANISM: Artificial Sequence
<220> FEATURE:
<223> OTHER INFORMATION: Synthetic Nucleic Acid

<400> SEQUENCE: 108
ccataacgac gcgggtct                                                   18

<210> SEQ ID NO 109
<211> LENGTH: 17
<212> TYPE: DNA
<213> ORGANISM: Artificial Sequence
<220> FEATURE:
<223> OTHER INFORMATION: Synthetic Nucleic Acid
<220> FEATURE:
<221> NAME/KEY: misc_feature
<222> LOCATION: (14)..(14)
<223> OTHER INFORMATION: "Y" is C or T

<400> SEQUENCE: 109
tgcgcctctt ccgyttt                                                    17

<210> SEQ ID NO 110
<211> LENGTH: 14
<212> TYPE: DNA
<213> ORGANISM: Artificial Sequence
<220> FEATURE:
<223> OTHER INFORMATION: Synthetic Nucleic Acid

<400> SEQUENCE: 110
tccagcttga gcgg                                                       14

<210> SEQ ID NO 111
<211> LENGTH: 19
<212> TYPE: DNA
<213> ORGANISM: Artificial Sequence
<220> FEATURE:
<223> OTHER INFORMATION: Synthetic Nucleic Acid

<400> SEQUENCE: 111
cgctggcggt caaaccttc                                                  19

```
<210> SEQ ID NO 112
<211> LENGTH: 21
<212> TYPE: DNA
<213> ORGANISM: Artificial Sequence
<220> FEATURE:
<223> OTHER INFORMATION: Synthetic Nucleic Acid
<220> FEATURE:
<221> NAME/KEY: misc_feature
<222> LOCATION: (14)..(14)
<223> OTHER INFORMATION: "K" is G or T

<400> SEQUENCE: 112
cttaaggacc cgcktcgtca t                                              21

<210> SEQ ID NO 113
<211> LENGTH: 14
<212> TYPE: DNA
<213> ORGANISM: Artificial Sequence
<220> FEATURE:
<223> OTHER INFORMATION: Synthetic Nucleic Acid

<400> SEQUENCE: 113
ctwtgagcag gcca                                                      14

<210> SEQ ID NO 114
<211> LENGTH: 21
<212> TYPE: DNA
<213> ORGANISM: Artificial Sequence
<220> FEATURE:
<223> OTHER INFORMATION: Synthetic Nucleic Acid

<400> SEQUENCE: 114
cccatgtcca tggcacagac t                                              21

<210> SEQ ID NO 115
<211> LENGTH: 26
<212> TYPE: DNA
<213> ORGANISM: Artificial Sequence
<220> FEATURE:
<223> OTHER INFORMATION: Synthetic Nucleic Acid

<400> SEQUENCE: 115
gctgcccctt ggatttatat gtcaac                                         26

<210> SEQ ID NO 116
<211> LENGTH: 16
<212> TYPE: DNA
<213> ORGANISM: Artificial Sequence
<220> FEATURE:
<223> OTHER INFORMATION: Synthetic Nucleic Acid

<400> SEQUENCE: 116
tctccaaaaa tcagct                                                    16

<210> SEQ ID NO 117
<211> LENGTH: 24
<212> TYPE: DNA
<213> ORGANISM: Artificial Sequence
<220> FEATURE:
<223> OTHER INFORMATION: Synthetic Nucleic Acid

<400> SEQUENCE: 117
ggtgaggctc tatcctatcc agac                                           24

<210> SEQ ID NO 118
<211> LENGTH: 16
<212> TYPE: DNA
```

```
<213> ORGANISM: Artificial Sequence
<220> FEATURE:
<223> OTHER INFORMATION: Synthetic Nucleic Acid

<400> SEQUENCE: 118
gcgtccaggc gctgaa                                              16

<210> SEQ ID NO 119
<211> LENGTH: 14
<212> TYPE: DNA
<213> ORGANISM: Artificial Sequence
<220> FEATURE:
<223> OTHER INFORMATION: Synthetic Nucleic Acid

<400> SEQUENCE: 119
tctcccaacc cctg                                                14

<210> SEQ ID NO 120
<211> LENGTH: 24
<212> TYPE: DNA
<213> ORGANISM: Artificial Sequence
<220> FEATURE:
<223> OTHER INFORMATION: Synthetic Nucleic Acid

<400> SEQUENCE: 120
gttactggcg tattggcgat atgt                                     24

<210> SEQ ID NO 121
<211> LENGTH: 18
<212> TYPE: DNA
<213> ORGANISM: Artificial Sequence
<220> FEATURE:
<223> OTHER INFORMATION: Synthetic Nucleic Acid

<400> SEQUENCE: 121
ggctttcacc ggccagtt                                            18

<210> SEQ ID NO 122
<211> LENGTH: 14
<212> TYPE: DNA
<213> ORGANISM: Artificial Sequence
<220> FEATURE:
<223> OTHER INFORMATION: Synthetic Nucleic Acid

<400> SEQUENCE: 122
cccagcccag accc                                                14

<210> SEQ ID NO 123
<211> LENGTH: 14
<212> TYPE: DNA
<213> ORGANISM: Artificial Sequence
<220> FEATURE:
<223> OTHER INFORMATION: Synthetic Nucleic Acid

<400> SEQUENCE: 123
tcccagccca gacc                                                14

<210> SEQ ID NO 124
<211> LENGTH: 14
<212> TYPE: DNA
<213> ORGANISM: Artificial Sequence
<220> FEATURE:
<223> OTHER INFORMATION: Synthetic Nucleic Acid

<400> SEQUENCE: 124
tctcccagcc caga                                                14
```

<210> SEQ ID NO 125
<211> LENGTH: 15
<212> TYPE: DNA
<213> ORGANISM: Artificial Sequence
<220> FEATURE:
<223> OTHER INFORMATION: Synthetic Nucleic Acid

<400> SEQUENCE: 125
tctcccagcc cagac                                                   15

<210> SEQ ID NO 126
<211> LENGTH: 24
<212> TYPE: DNA
<213> ORGANISM: Artificial Sequence
<220> FEATURE:
<223> OTHER INFORMATION: Synthetic Nucleic Acid

<400> SEQUENCE: 126
gaggaggtgg attcatccga gaag                                         24

<210> SEQ ID NO 127
<211> LENGTH: 19
<212> TYPE: DNA
<213> ORGANISM: Artificial Sequence
<220> FEATURE:
<223> OTHER INFORMATION: Synthetic Nucleic Acid

<400> SEQUENCE: 127
gatgggagcc cggcgaata                                               19

<210> SEQ ID NO 128
<211> LENGTH: 13
<212> TYPE: DNA
<213> ORGANISM: Artificial Sequence
<220> FEATURE:
<223> OTHER INFORMATION: Synthetic Nucleic Acid

<400> SEQUENCE: 128
cctactaccg cca                                                     13

<210> SEQ ID NO 129
<211> LENGTH: 14
<212> TYPE: DNA
<213> ORGANISM: Artificial Sequence
<220> FEATURE:
<223> OTHER INFORMATION: Synthetic Nucleic Acid

<400> SEQUENCE: 129
cctactaccg ccag                                                    14

<210> SEQ ID NO 130
<211> LENGTH: 15
<212> TYPE: DNA
<213> ORGANISM: Artificial Sequence
<220> FEATURE:
<223> OTHER INFORMATION: Synthetic Nucleic Acid

<400> SEQUENCE: 130
cctactaccg ccagt                                                   15

<210> SEQ ID NO 131
<211> LENGTH: 16
<212> TYPE: DNA
<213> ORGANISM: Artificial Sequence
<220> FEATURE:

```
<223> OTHER INFORMATION: Synthetic Nucleic Acid

<400> SEQUENCE: 131
cctactaccg ccagtg                                                    16

<210> SEQ ID NO 132
<211> LENGTH: 15
<212> TYPE: DNA
<213> ORGANISM: Artificial Sequence
<220> FEATURE:
<223> OTHER INFORMATION: Synthetic Nucleic Acid

<400> SEQUENCE: 132
ctactaccgc cagtg                                                     15

<210> SEQ ID NO 133
<211> LENGTH: 14
<212> TYPE: DNA
<213> ORGANISM: Artificial Sequence
<220> FEATURE:
<223> OTHER INFORMATION: Synthetic Nucleic Acid

<400> SEQUENCE: 133
tactaccgcc agtg                                                      14

<210> SEQ ID NO 134
<211> LENGTH: 19
<212> TYPE: DNA
<213> ORGANISM: Artificial Sequence
<220> FEATURE:
<223> OTHER INFORMATION: Synthetic Nucleic Acid
<220> FEATURE:
<221> NAME/KEY: misc_feature
<222> LOCATION: (18)..(18)
<223> OTHER INFORMATION: "W" is A or T

<400> SEQUENCE: 134
gatatggccc gctggrtwc                                                 19

<210> SEQ ID NO 135
<211> LENGTH: 17
<212> TYPE: DNA
<213> ORGANISM: Artificial Sequence
<220> FEATURE:
<223> OTHER INFORMATION: Synthetic Nucleic Acid
<220> FEATURE:
<221> NAME/KEY: misc_feature
<222> LOCATION: (13)..(13)
<223> OTHER INFORMATION: "Y" is C or T

<400> SEQUENCE: 135
cgcaatgccc tgytgga                                                   17

<210> SEQ ID NO 136
<211> LENGTH: 13
<212> TYPE: DNA
<213> ORGANISM: Artificial Sequence
<220> FEATURE:
<223> OTHER INFORMATION: Synthetic Nucleic Acid
<220> FEATURE:
<221> NAME/KEY: misc_feature
<222> LOCATION: (3)..(3)
<223> OTHER INFORMATION: "R" is G or A

<400> SEQUENCE: 136
ccrcgttcag gag                                                       13
```

```
<210> SEQ ID NO 137
<211> LENGTH: 14
<212> TYPE: DNA
<213> ORGANISM: Artificial Sequence
<220> FEATURE:
<223> OTHER INFORMATION: Synthetic Nucleic Acid
<220> FEATURE:
<221> NAME/KEY: misc_feature
<222> LOCATION: (3)..(3)
<223> OTHER INFORMATION: "R" is G or A

<400> SEQUENCE: 137
ccrcgttcag gaga                                                        14

<210> SEQ ID NO 138
<211> LENGTH: 15
<212> TYPE: DNA
<213> ORGANISM: Artificial Sequence
<220> FEATURE:
<223> OTHER INFORMATION: Synthetic Nucleic Acid
<220> FEATURE:
<221> NAME/KEY: misc_feature
<222> LOCATION: (3)..(3)
<223> OTHER INFORMATION: "R" is G or A

<400> SEQUENCE: 138
ccrcgttcag gagaa                                                       15

<210> SEQ ID NO 139
<211> LENGTH: 14
<212> TYPE: DNA
<213> ORGANISM: Artificial Sequence
<220> FEATURE:
<223> OTHER INFORMATION: Synthetic Nucleic Acid
<220> FEATURE:
<221> NAME/KEY: misc_feature
<222> LOCATION: (7)..(7)
<223> OTHER INFORMATION: "R" is G or A

<400> SEQUENCE: 139
ccagccrcgt tcag                                                        14

<210> SEQ ID NO 140
<211> LENGTH: 13
<212> TYPE: DNA
<213> ORGANISM: Artificial Sequence
<220> FEATURE:
<223> OTHER INFORMATION: Synthetic Nucleic Acid

<400> SEQUENCE: 140
tccatgttgg cct                                                         13

<210> SEQ ID NO 141
<211> LENGTH: 15
<212> TYPE: DNA
<213> ORGANISM: Artificial Sequence
<220> FEATURE:
<223> OTHER INFORMATION: Synthetic Nucleic Acid

<400> SEQUENCE: 141
ttcaggagaa aacgc                                                       15

<210> SEQ ID NO 142
<211> LENGTH: 21
<212> TYPE: DNA
<213> ORGANISM: Artificial Sequence
<220> FEATURE:
<223> OTHER INFORMATION: Synthetic Nucleic Acid
```

<400> SEQUENCE: 142
ctgggtctgt ttagtggcaa a                                    21

<210> SEQ ID NO 143
<211> LENGTH: 26
<212> TYPE: DNA
<213> ORGANISM: Artificial Sequence
<220> FEATURE:
<223> OTHER INFORMATION: Synthetic Nucleic Acid

<400> SEQUENCE: 143
gtctgttacc tgtacttaat gactcc                               26

<210> SEQ ID NO 144
<211> LENGTH: 13
<212> TYPE: DNA
<213> ORGANISM: Artificial Sequence
<220> FEATURE:
<223> OTHER INFORMATION: Synthetic Nucleic Acid

<400> SEQUENCE: 144
ccccgccata cga                                             13

<210> SEQ ID NO 145
<211> LENGTH: 18
<212> TYPE: DNA
<213> ORGANISM: Artificial Sequence
<220> FEATURE:
<223> OTHER INFORMATION: Synthetic Nucleic Acid

<400> SEQUENCE: 145
gggctccact ggcggatt                                        18

<210> SEQ ID NO 146
<211> LENGTH: 20
<212> TYPE: DNA
<213> ORGANISM: Artificial Sequence
<220> FEATURE:
<223> OTHER INFORMATION: Synthetic Nucleic Acid

<400> SEQUENCE: 146
gccagcatca cgatgccaag                                      20

<210> SEQ ID NO 147
<211> LENGTH: 15
<212> TYPE: DNA
<213> ORGANISM: Artificial Sequence
<220> FEATURE:
<223> OTHER INFORMATION: Synthetic Nucleic Acid

<400> SEQUENCE: 147
ctacgttgct ttcgt                                           15

<210> SEQ ID NO 148
<211> LENGTH: 17
<212> TYPE: DNA
<213> ORGANISM: Artificial Sequence
<220> FEATURE:
<223> OTHER INFORMATION: Synthetic Nucleic Acid
<220> FEATURE:
<221> NAME/KEY: misc_feature
<222> LOCATION: (6)..(6)
<223> OTHER INFORMATION: "K" is G or T

<400> SEQUENCE: 148
agtctkcctc ccgactg                                         17

<210> SEQ ID NO 149
<211> LENGTH: 16
<212> TYPE: DNA
<213> ORGANISM: Artificial Sequence
<220> FEATURE:
<223> OTHER INFORMATION: Synthetic Nucleic Acid
<220> FEATURE:
<221> NAME/KEY: misc_feature
<222> LOCATION: (4)..(4)
<223> OTHER INFORMATION: "Y" is C or T

<400> SEQUENCE: 149
cggygctgcc agcatt                                                         16

<210> SEQ ID NO 150
<211> LENGTH: 18
<212> TYPE: DNA
<213> ORGANISM: Artificial Sequence
<220> FEATURE:
<223> OTHER INFORMATION: Synthetic Nucleic Acid
<220> FEATURE:
<221> NAME/KEY: misc_feature
<222> LOCATION: (2)..(2)
<223> OTHER INFORMATION: "R" is G or A

<400> SEQUENCE: 150
crccgctgcc ggttttat                                                       18

<210> SEQ ID NO 151
<211> LENGTH: 14
<212> TYPE: DNA
<213> ORGANISM: Artificial Sequence
<220> FEATURE:
<223> OTHER INFORMATION: Synthetic Nucleic Acid

<400> SEQUENCE: 151
ctacccacat cgtg                                                           14

<210> SEQ ID NO 152
<211> LENGTH: 17
<212> TYPE: DNA
<213> ORGANISM: Artificial Sequence
<220> FEATURE:
<223> OTHER INFORMATION: Synthetic Nucleic Acid

<400> SEQUENCE: 152
tcatgcgctg ggcgaaa                                                        17

<210> SEQ ID NO 153
<211> LENGTH: 16
<212> TYPE: DNA
<213> ORGANISM: Artificial Sequence
<220> FEATURE:
<223> OTHER INFORMATION: Synthetic Nucleic Acid

<400> SEQUENCE: 153
gctgcgccgg tcgtat                                                         16

<210> SEQ ID NO 154
<211> LENGTH: 13
<212> TYPE: DNA
<213> ORGANISM: Artificial Sequence
<220> FEATURE:
<223> OTHER INFORMATION: Synthetic Nucleic Acid

<400> SEQUENCE: 154
caccaactgc gcc                                                          13

<210> SEQ ID NO 155
<211> LENGTH: 21
<212> TYPE: DNA
<213> ORGANISM: Artificial Sequence
<220> FEATURE:
<223> OTHER INFORMATION: Synthetic Nucleic Acid

<400> SEQUENCE: 155
tggccgcagc agaaagatat g                                                 21

<210> SEQ ID NO 156
<211> LENGTH: 21
<212> TYPE: DNA
<213> ORGANISM: Artificial Sequence
<220> FEATURE:
<223> OTHER INFORMATION: Synthetic Nucleic Acid
<220> FEATURE:
<221> NAME/KEY: misc_feature
<222> LOCATION: (18)..(18)
<223> OTHER INFORMATION: "R" is G or A

<400> SEQUENCE: 156
tggttgtctg ttaccggrtg c                                                 21

<210> SEQ ID NO 157
<211> LENGTH: 14
<212> TYPE: DNA
<213> ORGANISM: Artificial Sequence
<220> FEATURE:
<223> OTHER INFORMATION: Synthetic Nucleic Acid

<400> SEQUENCE: 157
ccaacgaggt cgca                                                         14

<210> SEQ ID NO 158
<211> LENGTH: 20
<212> TYPE: DNA
<213> ORGANISM: Artificial Sequence
<220> FEATURE:
<223> OTHER INFORMATION: Synthetic Nucleic Acid

<400> SEQUENCE: 158
agagggatcg ccatcgtcat                                                   20

<210> SEQ ID NO 159
<211> LENGTH: 16
<212> TYPE: DNA
<213> ORGANISM: Artificial Sequence
<220> FEATURE:
<223> OTHER INFORMATION: Synthetic Nucleic Acid

<400> SEQUENCE: 159
gcgtgagccg ccttca                                                       16

<210> SEQ ID NO 160
<211> LENGTH: 14
<212> TYPE: DNA
<213> ORGANISM: Artificial Sequence
<220> FEATURE:
<223> OTHER INFORMATION: Synthetic Nucleic Acid

<400> SEQUENCE: 160
tcccatcgag gcca                                                         14

-continued

```
<210> SEQ ID NO 161
<211> LENGTH: 22
<212> TYPE: DNA
<213> ORGANISM: Artificial Sequence
<220> FEATURE:
<223> OTHER INFORMATION: Synthetic Nucleic Acid

<400> SEQUENCE: 161
cctattgcta tggcacgtac tg                                           22

<210> SEQ ID NO 162
<211> LENGTH: 17
<212> TYPE: DNA
<213> ORGANISM: Artificial Sequence
<220> FEATURE:
<223> OTHER INFORMATION: Synthetic Nucleic Acid
<220> FEATURE:
<221> NAME/KEY: misc_feature
<222> LOCATION: (14)..(14)
<223> OTHER INFORMATION: "R" is G or A

<400> SEQUENCE: 162
tggtgtgggt cgargtg                                                 17

<210> SEQ ID NO 163
<211> LENGTH: 13
<212> TYPE: DNA
<213> ORGANISM: Artificial Sequence
<220> FEATURE:
<223> OTHER INFORMATION: Synthetic Nucleic Acid

<400> SEQUENCE: 163
ccgccataga gga                                                     13

<210> SEQ ID NO 164
<211> LENGTH: 14
<212> TYPE: DNA
<213> ORGANISM: Artificial Sequence
<220> FEATURE:
<223> OTHER INFORMATION: Synthetic Nucleic Acid

<400> SEQUENCE: 164
ccgccataga ggac                                                    14

<210> SEQ ID NO 165
<211> LENGTH: 13
<212> TYPE: DNA
<213> ORGANISM: Artificial Sequence
<220> FEATURE:
<223> OTHER INFORMATION: Synthetic Nucleic Acid

<400> SEQUENCE: 165
tcagtgcgcc gcc                                                     13

<210> SEQ ID NO 166
<211> LENGTH: 14
<212> TYPE: DNA
<213> ORGANISM: Artificial Sequence
<220> FEATURE:
<223> OTHER INFORMATION: Synthetic Nucleic Acid

<400> SEQUENCE: 166
tcagtgcgcc gcca                                                    14

<210> SEQ ID NO 167
<211> LENGTH: 13
<212> TYPE: DNA
```

```
<213> ORGANISM: Artificial Sequence
<220> FEATURE:
<223> OTHER INFORMATION: Synthetic Nucleic Acid

<400> SEQUENCE: 167
tcctctatgg cgg                                                          13

<210> SEQ ID NO 168
<211> LENGTH: 14
<212> TYPE: DNA
<213> ORGANISM: Artificial Sequence
<220> FEATURE:
<223> OTHER INFORMATION: Synthetic Nucleic Acid

<400> SEQUENCE: 168
tcctctatgg cggc                                                         14

<210> SEQ ID NO 169
<211> LENGTH: 15
<212> TYPE: DNA
<213> ORGANISM: Artificial Sequence
<220> FEATURE:
<223> OTHER INFORMATION: Synthetic Nucleic Acid

<400> SEQUENCE: 169
tcctctatgg cggcg                                                        15

<210> SEQ ID NO 170
<211> LENGTH: 26
<212> TYPE: DNA
<213> ORGANISM: Artificial Sequence
<220> FEATURE:
<223> OTHER INFORMATION: Synthetic Nucleic Acid

<400> SEQUENCE: 170
gaagacacga agttgttatt atcctg                                            26

<210> SEQ ID NO 171
<211> LENGTH: 22
<212> TYPE: DNA
<213> ORGANISM: Artificial Sequence
<220> FEATURE:
<223> OTHER INFORMATION: Synthetic Nucleic Acid

<400> SEQUENCE: 171
agaatgagtt gagatgctag cc                                                22

<210> SEQ ID NO 172
<211> LENGTH: 14
<212> TYPE: DNA
<213> ORGANISM: Artificial Sequence
<220> FEATURE:
<223> OTHER INFORMATION: Synthetic Nucleic Acid

<400> SEQUENCE: 172
cctggtatcc cctg                                                         14

<210> SEQ ID NO 173
<211> LENGTH: 21
<212> TYPE: DNA
<213> ORGANISM: Artificial Sequence
<220> FEATURE:
<223> OTHER INFORMATION: Synthetic Nucleic Acid

<400> SEQUENCE: 173
ggggactaac ataggcgtaa a                                                 21
```

<210> SEQ ID NO 174
<211> LENGTH: 24
<212> TYPE: DNA
<213> ORGANISM: Artificial Sequence
<220> FEATURE:
<223> OTHER INFORMATION: Synthetic Nucleic Acid

<400> SEQUENCE: 174
gttgagatga gtacgttatt cagg         24

<210> SEQ ID NO 175
<211> LENGTH: 14
<212> TYPE: DNA
<213> ORGANISM: Artificial Sequence
<220> FEATURE:
<223> OTHER INFORMATION: Synthetic Nucleic Acid

<400> SEQUENCE: 175
tcgcagctcg tgcg         14

<210> SEQ ID NO 176
<211> LENGTH: 26
<212> TYPE: DNA
<213> ORGANISM: Artificial Sequence
<220> FEATURE:
<223> OTHER INFORMATION: Synthetic Nucleic Acid
<220> FEATURE:
<221> NAME/KEY: misc_feature
<222> LOCATION: (6)..(6)
<223> OTHER INFORMATION: "M" is A or C

<400> SEQUENCE: 176
caactmaatc ttaatcagat cgtgaa         26

<210> SEQ ID NO 177
<211> LENGTH: 24
<212> TYPE: DNA
<213> ORGANISM: Artificial Sequence
<220> FEATURE:
<223> OTHER INFORMATION: Synthetic Nucleic Acid

<400> SEQUENCE: 177
gccatatcac ctaatgacat tcca         24

<210> SEQ ID NO 178
<211> LENGTH: 15
<212> TYPE: DNA
<213> ORGANISM: Artificial Sequence
<220> FEATURE:
<223> OTHER INFORMATION: Synthetic Nucleic Acid

<400> SEQUENCE: 178
ttcacccatc acaac         15

<210> SEQ ID NO 179
<211> LENGTH: 16
<212> TYPE: DNA
<213> ORGANISM: Artificial Sequence
<220> FEATURE:
<223> OTHER INFORMATION: Synthetic Nucleic Acid

<400> SEQUENCE: 179
ttcacccatc acaact         16

<210> SEQ ID NO 180

```
<211> LENGTH: 15
<212> TYPE: DNA
<213> ORGANISM: Artificial Sequence
<220> FEATURE:
<223> OTHER INFORMATION: Synthetic Nucleic Acid

<400> SEQUENCE: 180
ttccattcac ccatc                                                    15

<210> SEQ ID NO 181
<211> LENGTH: 17
<212> TYPE: DNA
<213> ORGANISM: Artificial Sequence
<220> FEATURE:
<223> OTHER INFORMATION: Synthetic Nucleic Acid

<400> SEQUENCE: 181
tttagttgtg atgggtg                                                  17

<210> SEQ ID NO 182
<211> LENGTH: 21
<212> TYPE: DNA
<213> ORGANISM: Artificial Sequence
<220> FEATURE:
<223> OTHER INFORMATION: Synthetic Nucleic Acid
<220> FEATURE:
<221> NAME/KEY: misc_feature
<222> LOCATION: (13)..(13)
<223> OTHER INFORMATION: "Y" is C or T
<220> FEATURE:
<221> NAME/KEY: misc_feature
<222> LOCATION: (15)..(15)
<223> OTHER INFORMATION: "R" is G or A

<400> SEQUENCE: 182
gtagtggttt ggytrcctga a                                             21

<210> SEQ ID NO 183
<211> LENGTH: 24
<212> TYPE: DNA
<213> ORGANISM: Artificial Sequence
<220> FEATURE:
<223> OTHER INFORMATION: Synthetic Nucleic Acid
<220> FEATURE:
<221> NAME/KEY: misc_feature
<222> LOCATION: (14)..(14)
<223> OTHER INFORMATION: "Y" is C or T
<220> FEATURE:
<221> NAME/KEY: misc_feature
<222> LOCATION: (18)..(18)
<223> OTHER INFORMATION: "R" is G or A

<400> SEQUENCE: 183
ccgtacggtt taayaaarca acca                                          24

<210> SEQ ID NO 184
<211> LENGTH: 19
<212> TYPE: DNA
<213> ORGANISM: Artificial Sequence
<220> FEATURE:
<223> OTHER INFORMATION: Synthetic Nucleic Acid

<400> SEQUENCE: 184
acacggcttg gtggttctt                                                19

<210> SEQ ID NO 185
<211> LENGTH: 26
<212> TYPE: DNA
<213> ORGANISM: Artificial Sequence
```

```
<220> FEATURE:
<223> OTHER INFORMATION: Synthetic Nucleic Acid

<400> SEQUENCE: 185
tcagtatctt tagccgtaaa tggagt                                        26

<210> SEQ ID NO 186
<211> LENGTH: 15
<212> TYPE: DNA
<213> ORGANISM: Artificial Sequence
<220> FEATURE:
<223> OTHER INFORMATION: Synthetic Nucleic Acid

<400> SEQUENCE: 186
ctgaggccta tctga                                                    15

<210> SEQ ID NO 187
<211> LENGTH: 18
<212> TYPE: DNA
<213> ORGANISM: Artificial Sequence
<220> FEATURE:
<223> OTHER INFORMATION: Synthetic Nucleic Acid

<400> SEQUENCE: 187
atgaacgcgc aggccatt                                                 18

<210> SEQ ID NO 188
<211> LENGTH: 24
<212> TYPE: DNA
<213> ORGANISM: Artificial Sequence
<220> FEATURE:
<223> OTHER INFORMATION: Synthetic Nucleic Acid

<400> SEQUENCE: 188
cgaaggtaaa gtagtgtggc tgac                                          24

<210> SEQ ID NO 189
<211> LENGTH: 13
<212> TYPE: DNA
<213> ORGANISM: Artificial Sequence
<220> FEATURE:
<223> OTHER INFORMATION: Synthetic Nucleic Acid

<400> SEQUENCE: 189
ccgccaccgc cat                                                      13

<210> SEQ ID NO 190
<211> LENGTH: 18
<212> TYPE: DNA
<213> ORGANISM: Artificial Sequence
<220> FEATURE:
<223> OTHER INFORMATION: Synthetic Nucleic Acid
<220> FEATURE:
<221> NAME/KEY: misc_feature
<222> LOCATION: (15)..(15)
<223> OTHER INFORMATION: "R" is G or A
<220> FEATURE:
<221> NAME/KEY: misc_feature
<222> LOCATION: (16)..(16)
<223> OTHER INFORMATION: "R" is G or A
<220> FEATURE:
<221> NAME/KEY: misc_feature
<222> LOCATION: (18)..(18)
<223> OTHER INFORMATION: "R" is G or A

<400> SEQUENCE: 190
ctgaccgcga ccctrggr                                                 18
```

```
<210> SEQ ID NO 191
<211> LENGTH: 20
<212> TYPE: DNA
<213> ORGANISM: Artificial Sequence
<220> FEATURE:
<223> OTHER INFORMATION: Synthetic Nucleic Acid
<220> FEATURE:
<221> NAME/KEY: misc_feature
<222> LOCATION: (19)..(19)
<223> OTHER INFORMATION: "Y" is C or T
<220> FEATURE:
<221> NAME/KEY: misc_feature
<222> LOCATION: (20)..(20)
<223> OTHER INFORMATION: "Y" is C or T

<400> SEQUENCE: 191
gctcgccttg tcatccagyt                                            20

<210> SEQ ID NO 192
<211> LENGTH: 14
<212> TYPE: DNA
<213> ORGANISM: Artificial Sequence
<220> FEATURE:
<223> OTHER INFORMATION: Synthetic Nucleic Acid

<400> SEQUENCE: 192
ctcccttgac cacc                                                  14

<210> SEQ ID NO 193
<211> LENGTH: 17
<212> TYPE: DNA
<213> ORGANISM: Artificial Sequence
<220> FEATURE:
<223> OTHER INFORMATION: Synthetic Nucleic Acid
<220> FEATURE:
<221> NAME/KEY: misc_feature
<222> LOCATION: (11)..(11)
<223> OTHER INFORMATION: "S" is C or G
<220> FEATURE:
<221> NAME/KEY: misc_feature
<222> LOCATION: (12)..(12)
<223> OTHER INFORMATION: "S" is C or G

<400> SEQUENCE: 193
gtcactcccg scatgct                                               17

<210> SEQ ID NO 194
<211> LENGTH: 18
<212> TYPE: DNA
<213> ORGANISM: Artificial Sequence
<220> FEATURE:
<223> OTHER INFORMATION: Synthetic Nucleic Acid
<220> FEATURE:
<221> NAME/KEY: misc_feature
<222> LOCATION: (13)..(13)
<223> OTHER INFORMATION: "R" is G or A
<220> FEATURE:
<221> NAME/KEY: misc_feature
<222> LOCATION: (14)..(14)
<223> OTHER INFORMATION: "R" is G or A

<400> SEQUENCE: 194
cagatccgcc garctggt                                              18

<210> SEQ ID NO 195
<211> LENGTH: 15
<212> TYPE: DNA
<213> ORGANISM: Artificial Sequence
<220> FEATURE:
<223> OTHER INFORMATION: Synthetic Nucleic Acid
```

```
<220> FEATURE:
<221> NAME/KEY: misc_feature
<222> LOCATION: (2)..(2)
<223> OTHER INFORMATION: "Y" is C or T

<400> SEQUENCE: 195
cytacggcat caaga                                                      15

<210> SEQ ID NO 196
<211> LENGTH: 24
<212> TYPE: DNA
<213> ORGANISM: Artificial Sequence
<220> FEATURE:
<223> OTHER INFORMATION: Synthetic Nucleic Acid

<400> SEQUENCE: 196
attttagact cgatcgttgg gagt                                            24

<210> SEQ ID NO 197
<211> LENGTH: 20
<212> TYPE: DNA
<213> ORGANISM: Artificial Sequence
<220> FEATURE:
<223> OTHER INFORMATION: Synthetic Nucleic Acid

<400> SEQUENCE: 197
tgctgcaggt gtagatgtgt                                                 20

<210> SEQ ID NO 198
<211> LENGTH: 15
<212> TYPE: DNA
<213> ORGANISM: Artificial Sequence
<220> FEATURE:
<223> OTHER INFORMATION: Synthetic Nucleic Acid

<400> SEQUENCE: 198
ttccaggcga tgagc                                                      15

<210> SEQ ID NO 199
<211> LENGTH: 17
<212> TYPE: DNA
<213> ORGANISM: Artificial Sequence
<220> FEATURE:
<223> OTHER INFORMATION: Synthetic Nucleic Acid

<400> SEQUENCE: 199
atcctggtgt cgcatgg                                                    17

<210> SEQ ID NO 200
<211> LENGTH: 26
<212> TYPE: DNA
<213> ORGANISM: Artificial Sequence
<220> FEATURE:
<223> OTHER INFORMATION: Synthetic Nucleic Acid

<400> SEQUENCE: 200
ttcgttgtct atatccatgt taaagg                                          26

<210> SEQ ID NO 201
<211> LENGTH: 15
<212> TYPE: DNA
<213> ORGANISM: Artificial Sequence
<220> FEATURE:
<223> OTHER INFORMATION: Synthetic Nucleic Acid

<400> SEQUENCE: 201
```
cctctgtctc cttct                                                        15

<210> SEQ ID NO 202
<211> LENGTH: 14
<212> TYPE: DNA
<213> ORGANISM: Artificial Sequence
<220> FEATURE:
<223> OTHER INFORMATION: Synthetic Nucleic Acid

<400> SEQUENCE: 202
ctcaacccac ccaa                                                         14

<210> SEQ ID NO 203
<211> LENGTH: 15
<212> TYPE: DNA
<213> ORGANISM: Artificial Sequence
<220> FEATURE:
<223> OTHER INFORMATION: Synthetic Nucleic Acid

<400> SEQUENCE: 203
ctcaacccac ccaac                                                        15

<210> SEQ ID NO 204
<211> LENGTH: 15
<212> TYPE: DNA
<213> ORGANISM: Artificial Sequence
<220> FEATURE:
<223> OTHER INFORMATION: Synthetic Nucleic Acid

<400> SEQUENCE: 204
tctccttctc aaccc                                                        15

<210> SEQ ID NO 205
<211> LENGTH: 18
<212> TYPE: DNA
<213> ORGANISM: Artificial Sequence
<220> FEATURE:
<223> OTHER INFORMATION: Synthetic Nucleic Acid

<400> SEQUENCE: 205
gccgaccgat ccgaccat                                                     18

<210> SEQ ID NO 206
<211> LENGTH: 20
<212> TYPE: DNA
<213> ORGANISM: Artificial Sequence
<220> FEATURE:
<223> OTHER INFORMATION: Synthetic Nucleic Acid

<400> SEQUENCE: 206
gcgtcagctc ctgcgaatac                                                   20

<210> SEQ ID NO 207
<211> LENGTH: 16
<212> TYPE: DNA
<213> ORGANISM: Artificial Sequence
<220> FEATURE:
<223> OTHER INFORMATION: Synthetic Nucleic Acid

<400> SEQUENCE: 207
ctgaaggatt ccatcg                                                       16

<210> SEQ ID NO 208
<211> LENGTH: 21
<212> TYPE: DNA
<213> ORGANISM: Artificial Sequence

```
<220> FEATURE:
<223> OTHER INFORMATION: Synthetic Nucleic Acid

<400> SEQUENCE: 208
ggcacgatag ttgtggcaga c                                              21

<210> SEQ ID NO 209
<211> LENGTH: 22
<212> TYPE: DNA
<213> ORGANISM: Artificial Sequence
<220> FEATURE:
<223> OTHER INFORMATION: Synthetic Nucleic Acid

<400> SEQUENCE: 209
cgtttcttcg atcgcacagg at                                             22

<210> SEQ ID NO 210
<211> LENGTH: 14
<212> TYPE: DNA
<213> ORGANISM: Artificial Sequence
<220> FEATURE:
<223> OTHER INFORMATION: Synthetic Nucleic Acid

<400> SEQUENCE: 210
tccgcttggc gttc                                                      14

<210> SEQ ID NO 211
<211> LENGTH: 18
<212> TYPE: DNA
<213> ORGANISM: Artificial Sequence
<220> FEATURE:
<223> OTHER INFORMATION: Synthetic Nucleic Acid

<400> SEQUENCE: 211
ttaggtgagg caatggca                                                  18

<210> SEQ ID NO 212
<211> LENGTH: 17
<212> TYPE: DNA
<213> ORGANISM: Artificial Sequence
<220> FEATURE:
<223> OTHER INFORMATION: Synthetic Nucleic Acid

<400> SEQUENCE: 212
tctaggccag tccgtct                                                   17

<210> SEQ ID NO 213
<211> LENGTH: 13
<212> TYPE: DNA
<213> ORGANISM: Artificial Sequence
<220> FEATURE:
<223> OTHER INFORMATION: Synthetic Nucleic Acid

<400> SEQUENCE: 213
tcagcagttc cag                                                       13

<210> SEQ ID NO 214
<211> LENGTH: 19
<212> TYPE: DNA
<213> ORGANISM: Artificial Sequence
<220> FEATURE:
<223> OTHER INFORMATION: Synthetic Nucleic Acid

<400> SEQUENCE: 214
gcaagggtgc ctgtgacaa                                                 19
```

<210> SEQ ID NO 215
<211> LENGTH: 20
<212> TYPE: DNA
<213> ORGANISM: Artificial Sequence
<220> FEATURE:
<223> OTHER INFORMATION: Synthetic Nucleic Acid

<400> SEQUENCE: 215
ccagcatcgt agcccatgac                                          20

<210> SEQ ID NO 216
<211> LENGTH: 14
<212> TYPE: DNA
<213> ORGANISM: Artificial Sequence
<220> FEATURE:
<223> OTHER INFORMATION: Synthetic Nucleic Acid

<400> SEQUENCE: 216
ccttcgcgcc aatg                                                14

<210> SEQ ID NO 217
<211> LENGTH: 18
<212> TYPE: DNA
<213> ORGANISM: Artificial Sequence
<220> FEATURE:
<223> OTHER INFORMATION: Synthetic Nucleic Acid

<400> SEQUENCE: 217
gcggaaaccc gcttcgtt                                            18

<210> SEQ ID NO 218
<211> LENGTH: 21
<212> TYPE: DNA
<213> ORGANISM: Artificial Sequence
<220> FEATURE:
<223> OTHER INFORMATION: Synthetic Nucleic Acid

<400> SEQUENCE: 218
cccctgtgga taagccgatc a                                        21

<210> SEQ ID NO 219
<211> LENGTH: 14
<212> TYPE: DNA
<213> ORGANISM: Artificial Sequence
<220> FEATURE:
<223> OTHER INFORMATION: Synthetic Nucleic Acid

<400> SEQUENCE: 219
cccgcttcca ccta                                                14

<210> SEQ ID NO 220
<211> LENGTH: 23
<212> TYPE: DNA
<213> ORGANISM: Artificial Sequence
<220> FEATURE:
<223> OTHER INFORMATION: Synthetic Nucleic Acid

<400> SEQUENCE: 220
agaattgagc ctcagatcgg ttg                                      23

<210> SEQ ID NO 221
<211> LENGTH: 21
<212> TYPE: DNA
<213> ORGANISM: Artificial Sequence
<220> FEATURE:
<223> OTHER INFORMATION: Synthetic Nucleic Acid -continued

<400> SEQUENCE: 221
tcatcgcgaa gaaccacaca t                                              21

<210> SEQ ID NO 222
<211> LENGTH: 15
<212> TYPE: DNA
<213> ORGANISM: Artificial Sequence
<220> FEATURE:
<223> OTHER INFORMATION: Synthetic Nucleic Acid

<400> SEQUENCE: 222
tcgagttcaa cccaa                                                     15

<210> SEQ ID NO 223
<211> LENGTH: 29
<212> TYPE: DNA
<213> ORGANISM: Artificial Sequence
<220> FEATURE:
<223> OTHER INFORMATION: Synthetic Nucleic Acid

<400> SEQUENCE: 223
cagcatttca acaagtggat tttctaagg                                      29

<210> SEQ ID NO 224
<211> LENGTH: 16
<212> TYPE: DNA
<213> ORGANISM: Artificial Sequence
<220> FEATURE:
<223> OTHER INFORMATION: Synthetic Nucleic Acid

<400> SEQUENCE: 224
gctgcgctcg gacaca                                                    16

<210> SEQ ID NO 225
<211> LENGTH: 16
<212> TYPE: DNA
<213> ORGANISM: Artificial Sequence
<220> FEATURE:
<223> OTHER INFORMATION: Synthetic Nucleic Acid

<400> SEQUENCE: 225
cttgttgtca tgcagt                                                    16

<210> SEQ ID NO 226
<211> LENGTH: 19
<212> TYPE: DNA
<213> ORGANISM: Artificial Sequence
<220> FEATURE:
<223> OTHER INFORMATION: Synthetic Nucleic Acid

<400> SEQUENCE: 226
ggctttgtag agtgcctca                                                 19

<210> SEQ ID NO 227
<211> LENGTH: 21
<212> TYPE: DNA
<213> ORGANISM: Artificial Sequence
<220> FEATURE:
<223> OTHER INFORMATION: Synthetic Nucleic Acid

<400> SEQUENCE: 227
cttggcgtta ttgctaaagc t                                              21

<210> SEQ ID NO 228

-continued

```
<211> LENGTH: 15
<212> TYPE: DNA
<213> ORGANISM: Artificial Sequence
<220> FEATURE:
<223> OTHER INFORMATION: Synthetic Nucleic Acid

<400> SEQUENCE: 228
catgactcaa atcgc                                                        15

<210> SEQ ID NO 229
<211> LENGTH: 20
<212> TYPE: DNA
<213> ORGANISM: Artificial Sequence
<220> FEATURE:
<223> OTHER INFORMATION: Synthetic Nucleic Acid

<400> SEQUENCE: 229
gaacagcctg atcgccttcg                                                   20

<210> SEQ ID NO 230
<211> LENGTH: 19
<212> TYPE: DNA
<213> ORGANISM: Artificial Sequence
<220> FEATURE:
<223> OTHER INFORMATION: Synthetic Nucleic Acid

<400> SEQUENCE: 230
ccgtagggca gcacttcct                                                    19

<210> SEQ ID NO 231
<211> LENGTH: 13
<212> TYPE: DNA
<213> ORGANISM: Artificial Sequence
<220> FEATURE:
<223> OTHER INFORMATION: Synthetic Nucleic Acid

<400> SEQUENCE: 231
tcgcgcacgg ccc                                                          13

<210> SEQ ID NO 232
<211> LENGTH: 21
<212> TYPE: DNA
<213> ORGANISM: Artificial Sequence
<220> FEATURE:
<223> OTHER INFORMATION: Synthetic Nucleic Acid

<400> SEQUENCE: 232
atcgggcgcc ggtacgcgca g                                                 21

<210> SEQ ID NO 233
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 233
cgccgccaat ggtgcggttg ccata                                             25

<210> SEQ ID NO 234
<211> LENGTH: 14
<212> TYPE: DNA
<213> ORGANISM: Artificial Sequence
<220> FEATURE:
<223> OTHER INFORMATION: Synthetic Nucleic Acid

<400> SEQUENCE: 234
```

```
cccgacctcg ttca                                                        14

<210> SEQ ID NO 235
<211> LENGTH: 15
<212> TYPE: DNA
<213> ORGANISM: Artificial Sequence
<220> FEATURE:
<223> OTHER INFORMATION: Synthetic Nucleic Acid

<400> SEQUENCE: 235
cctcgttcag cttcg                                                       15

<210> SEQ ID NO 236
<211> LENGTH: 15
<212> TYPE: DNA
<213> ORGANISM: Artificial Sequence
<220> FEATURE:
<223> OTHER INFORMATION: Synthetic Nucleic Acid

<400> SEQUENCE: 236
ctcgttcagc ttcgc                                                       15

<210> SEQ ID NO 237
<211> LENGTH: 21
<212> TYPE: DNA
<213> ORGANISM: Artificial Sequence
<220> FEATURE:
<223> OTHER INFORMATION: Synthetic Nucleic Acid

<400> SEQUENCE: 237
ggttgatcag ggaaagttgg a                                                21

<210> SEQ ID NO 238
<211> LENGTH: 21
<212> TYPE: DNA
<213> ORGANISM: Artificial Sequence
<220> FEATURE:
<223> OTHER INFORMATION: Synthetic Nucleic Acid

<400> SEQUENCE: 238
ttatcggagc ccaggtattc t                                                21

<210> SEQ ID NO 239
<211> LENGTH: 20
<212> TYPE: DNA
<213> ORGANISM: Artificial Sequence
<220> FEATURE:
<223> OTHER INFORMATION: Synthetic Nucleic Acid

<400> SEQUENCE: 239
ccgttatcgt aaacagggct                                                  20

<210> SEQ ID NO 240
<211> LENGTH: 19
<212> TYPE: DNA
<213> ORGANISM: Artificial Sequence
<220> FEATURE:
<223> OTHER INFORMATION: Synthetic Nucleic Acid

<400> SEQUENCE: 240
tgcaaactgg gtggttgga                                                   19

<210> SEQ ID NO 241
<211> LENGTH: 22
<212> TYPE: DNA
```

```
<213> ORGANISM: Artificial Sequence
<220> FEATURE:
<223> OTHER INFORMATION: Synthetic Nucleic Acid

<400> SEQUENCE: 241
aggccagatc actgcataat cg                                    22

<210> SEQ ID NO 242
<211> LENGTH: 15
<212> TYPE: DNA
<213> ORGANISM: Artificial Sequence
<220> FEATURE:
<223> OTHER INFORMATION: Synthetic Nucleic Acid

<400> SEQUENCE: 242
ccacaagtac ccgtt                                            15

<210> SEQ ID NO 243
<211> LENGTH: 17
<212> TYPE: DNA
<213> ORGANISM: Artificial Sequence
<220> FEATURE:
<223> OTHER INFORMATION: Synthetic Nucleic Acid

<400> SEQUENCE: 243
ccggcgggct ggtttat                                          17

<210> SEQ ID NO 244
<211> LENGTH: 22
<212> TYPE: DNA
<213> ORGANISM: Artificial Sequence
<220> FEATURE:
<223> OTHER INFORMATION: Synthetic Nucleic Acid

<400> SEQUENCE: 244
ctgctttgtt attcgggcca ag                                    22

<210> SEQ ID NO 245
<211> LENGTH: 13
<212> TYPE: DNA
<213> ORGANISM: Artificial Sequence
<220> FEATURE:
<223> OTHER INFORMATION: Synthetic Nucleic Acid

<400> SEQUENCE: 245
tcgctagctc cgg                                              13

<210> SEQ ID NO 246
<211> LENGTH: 16
<212> TYPE: DNA
<213> ORGANISM: Artificial Sequence
<220> FEATURE:
<223> OTHER INFORMATION: Synthetic Nucleic Acid

<400> SEQUENCE: 246
ggccccgcag gattga                                           16

<210> SEQ ID NO 247
<211> LENGTH: 16
<212> TYPE: DNA
<213> ORGANISM: Artificial Sequence
<220> FEATURE:
<223> OTHER INFORMATION: Synthetic Nucleic Acid

<400> SEQUENCE: 247
ggtcaaggcg ggtgac                                           16
```

```
<210> SEQ ID NO 248
<211> LENGTH: 14
<212> TYPE: DNA
<213> ORGANISM: Artificial Sequence
<220> FEATURE:
<223> OTHER INFORMATION: Synthetic Nucleic Acid

<400> SEQUENCE: 248
ccagatcggc gaca                                                        14

<210> SEQ ID NO 249
<211> LENGTH: 14
<212> TYPE: DNA
<213> ORGANISM: Artificial Sequence
<220> FEATURE:
<223> OTHER INFORMATION: Synthetic Nucleic Acid

<400> SEQUENCE: 249
tcgccgatct ggcg                                                        14

<210> SEQ ID NO 250
<211> LENGTH: 15
<212> TYPE: DNA
<213> ORGANISM: Artificial Sequence
<220> FEATURE:
<223> OTHER INFORMATION: Synthetic Nucleic Acid

<400> SEQUENCE: 250
tcgccgatct ggcgc                                                       15

<210> SEQ ID NO 251
<211> LENGTH: 15
<212> TYPE: DNA
<213> ORGANISM: Artificial Sequence
<220> FEATURE:
<223> OTHER INFORMATION: Synthetic Nucleic Acid

<400> SEQUENCE: 251
ttgtcgccga tctgg                                                       15

<210> SEQ ID NO 252
<211> LENGTH: 14
<212> TYPE: DNA
<213> ORGANISM: Artificial Sequence
<220> FEATURE:
<223> OTHER INFORMATION: Synthetic Nucleic Acid

<400> SEQUENCE: 252
ccagatcgac gaca                                                        14

<210> SEQ ID NO 253
<211> LENGTH: 14
<212> TYPE: DNA
<213> ORGANISM: Artificial Sequence
<220> FEATURE:
<223> OTHER INFORMATION: Synthetic Nucleic Acid

<400> SEQUENCE: 253
tcgtcgatct ggcg                                                        14

<210> SEQ ID NO 254
<211> LENGTH: 15
<212> TYPE: DNA
<213> ORGANISM: Artificial Sequence
<220> FEATURE:
```

<223> OTHER INFORMATION: Synthetic Nucleic Acid

<400> SEQUENCE: 254
ttgtcgtcga tctgg                                                        15

<210> SEQ ID NO 255
<211> LENGTH: 13
<212> TYPE: DNA
<213> ORGANISM: Artificial Sequence
<220> FEATURE:
<223> OTHER INFORMATION: Synthetic Nucleic Acid

<400> SEQUENCE: 255
tcgccagctc cgg                                                          13

<210> SEQ ID NO 256
<211> LENGTH: 13
<212> TYPE: DNA
<213> ORGANISM: Artificial Sequence
<220> FEATURE:
<223> OTHER INFORMATION: Synthetic Nucleic Acid

<400> SEQUENCE: 256
ttgccagctc cgg                                                          13

<210> SEQ ID NO 257
<211> LENGTH: 13
<212> TYPE: DNA
<213> ORGANISM: Artificial Sequence
<220> FEATURE:
<223> OTHER INFORMATION: Synthetic Nucleic Acid

<400> SEQUENCE: 257
ttgctagctc cgg                                                          13

<210> SEQ ID NO 258
<211> LENGTH: 20
<212> TYPE: DNA
<213> ORGANISM: Artificial Sequence
<220> FEATURE:
<223> OTHER INFORMATION: Synthetic Nucleic Acid

<400> SEQUENCE: 258
ggccttggca atctaagtga                                                   20

<210> SEQ ID NO 259
<211> LENGTH: 19
<212> TYPE: DNA
<213> ORGANISM: Artificial Sequence
<220> FEATURE:
<223> OTHER INFORMATION: Synthetic Nucleic Acid

<400> SEQUENCE: 259
tgcgtctccg atttcactg                                                    19

<210> SEQ ID NO 260
<211> LENGTH: 14
<212> TYPE: DNA
<213> ORGANISM: Artificial Sequence
<220> FEATURE:
<223> OTHER INFORMATION: Synthetic Nucleic Acid

<400> SEQUENCE: 260
cctggccaag cttc                                                         14

```
<210> SEQ ID NO 261
<211> LENGTH: 18
<212> TYPE: DNA
<213> ORGANISM: Artificial Sequence
<220> FEATURE:
<223> OTHER INFORMATION: Synthetic Nucleic Acid

<400> SEQUENCE: 261
cgatttcttg gcggtcct                                                 18

<210> SEQ ID NO 262
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 262
cctaaactca ttatctccaa tagaacg                                       27

<210> SEQ ID NO 263
<211> LENGTH: 16
<212> TYPE: DNA
<213> ORGANISM: Artificial Sequence
<220> FEATURE:
<223> OTHER INFORMATION: Synthetic Nucleic Acid

<400> SEQUENCE: 263
tttagtcatc ccctca                                                   16

<210> SEQ ID NO 264
<211> LENGTH: 22
<212> TYPE: DNA
<213> ORGANISM: Artificial Sequence
<220> FEATURE:
<223> OTHER INFORMATION: Synthetic Nucleic Acid

<400> SEQUENCE: 264
catcctgttc cagcggataa tg                                            22

<210> SEQ ID NO 265
<211> LENGTH: 24
<212> TYPE: DNA
<213> ORGANISM: Artificial Sequence
<220> FEATURE:
<223> OTHER INFORMATION: Synthetic Nucleic Acid

<400> SEQUENCE: 265
acctcaacca gctcattaga aaac                                          24

<210> SEQ ID NO 266
<211> LENGTH: 15
<212> TYPE: DNA
<213> ORGANISM: Artificial Sequence
<220> FEATURE:
<223> OTHER INFORMATION: Synthetic Nucleic Acid

<400> SEQUENCE: 266
ccttgccttg tttca                                                    15

<210> SEQ ID NO 267
<211> LENGTH: 19
<212> TYPE: DNA
<213> ORGANISM: Artificial Sequence
<220> FEATURE:
<223> OTHER INFORMATION: Synthetic Nucleic Acid
```

<400> SEQUENCE: 267
tgccatccgt aagatgctt                                                19

<210> SEQ ID NO 268
<211> LENGTH: 16
<212> TYPE: DNA
<213> ORGANISM: Artificial Sequence
<220> FEATURE:
<223> OTHER INFORMATION: Synthetic Nucleic Acid

<400> SEQUENCE: 268
ccgggcaaga gcaact                                                   16

<210> SEQ ID NO 269
<211> LENGTH: 17
<212> TYPE: DNA
<213> ORGANISM: Artificial Sequence
<220> FEATURE:
<223> OTHER INFORMATION: Synthetic Nucleic Acid

<400> SEQUENCE: 269
cttggttgag tactcac                                                  17

<210> SEQ ID NO 270
<211> LENGTH: 17
<212> TYPE: DNA
<213> ORGANISM: Artificial Sequence
<220> FEATURE:
<223> OTHER INFORMATION: Synthetic Nucleic Acid

<400> SEQUENCE: 270
cttggttaag tactcac                                                  17

<210> SEQ ID NO 271
<211> LENGTH: 15
<212> TYPE: DNA
<213> ORGANISM: Artificial Sequence
<220> FEATURE:
<223> OTHER INFORMATION: Synthetic Nucleic Acid

<400> SEQUENCE: 271
ccatctggcc ccagt                                                    15

<210> SEQ ID NO 272
<211> LENGTH: 17
<212> TYPE: DNA
<213> ORGANISM: Artificial Sequence
<220> FEATURE:
<223> OTHER INFORMATION: Synthetic Nucleic Acid

<400> SEQUENCE: 272
cggctggctg gtttatt                                                  17

<210> SEQ ID NO 273
<211> LENGTH: 15
<212> TYPE: DNA
<213> ORGANISM: Artificial Sequence
<220> FEATURE:
<223> OTHER INFORMATION: Synthetic Nucleic Acid

<400> SEQUENCE: 273
ctcaccggct ccaga                                                    15

<210> SEQ ID NO 274
<211> LENGTH: 15

```
<212> TYPE: DNA
<213> ORGANISM: Artificial Sequence
<220> FEATURE:
<223> OTHER INFORMATION: Synthetic Nucleic Acid

<400> SEQUENCE: 274
cttaccggct ccaga                                                      15

<210> SEQ ID NO 275
<211> LENGTH: 15
<212> TYPE: DNA
<213> ORGANISM: Artificial Sequence
<220> FEATURE:
<223> OTHER INFORMATION: Synthetic Nucleic Acid

<400> SEQUENCE: 275
ctcactggct ccaga                                                      15

<210> SEQ ID NO 276
<211> LENGTH: 15
<212> TYPE: DNA
<213> ORGANISM: Artificial Sequence
<220> FEATURE:
<223> OTHER INFORMATION: Synthetic Nucleic Acid

<400> SEQUENCE: 276
cttactggct ccaga                                                      15

<210> SEQ ID NO 277
<211> LENGTH: 21
<212> TYPE: DNA
<213> ORGANISM: Artificial Sequence
<220> FEATURE:
<223> OTHER INFORMATION: Synthetic Nucleic Acid

<400> SEQUENCE: 277
ttctgacaac gatcggagga c                                               21

<210> SEQ ID NO 278
<211> LENGTH: 19
<212> TYPE: DNA
<213> ORGANISM: Artificial Sequence
<220> FEATURE:
<223> OTHER INFORMATION: Synthetic Nucleic Acid

<400> SEQUENCE: 278
tcgtggtgtc acgctcgtc                                                  19

<210> SEQ ID NO 279
<211> LENGTH: 16
<212> TYPE: DNA
<213> ORGANISM: Artificial Sequence
<220> FEATURE:
<223> OTHER INFORMATION: Synthetic Nucleic Acid

<400> SEQUENCE: 279
tcccaacgat caaggc                                                     16

<210> SEQ ID NO 280
<211> LENGTH: 16
<212> TYPE: DNA
<213> ORGANISM: Artificial Sequence
<220> FEATURE:
<223> OTHER INFORMATION: Synthetic Nucleic Acid
<220> FEATURE:
<221> NAME/KEY: misc_feature
<222> LOCATION: (11)..(11)
```

```
<223> OTHER INFORMATION: "S" is C or G
<220> FEATURE:
<221> NAME/KEY: misc_feature
<222> LOCATION: (12)..(12)
<223> OTHER INFORMATION: "S" is C or G

<400> SEQUENCE: 280
tcccaacaat saaggc                                                    16

<210> SEQ ID NO 281
<211> LENGTH: 16
<212> TYPE: DNA
<213> ORGANISM: Artificial Sequence
<220> FEATURE:
<223> OTHER INFORMATION: Synthetic Nucleic Acid

<400> SEQUENCE: 281
tcccaatgat caaggc                                                    16

<210> SEQ ID NO 282
<211> LENGTH: 16
<212> TYPE: DNA
<213> ORGANISM: Artificial Sequence
<220> FEATURE:
<223> OTHER INFORMATION: Synthetic Nucleic Acid

<400> SEQUENCE: 282
tcccaactat caaggc                                                    16

<210> SEQ ID NO 283
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 283
ctgttgttgc tcataaaacc ggaag                                          25

<210> SEQ ID NO 284
<211> LENGTH: 24
<212> TYPE: DNA
<213> ORGANISM: Artificial Sequence
<220> FEATURE:
<223> OTHER INFORMATION: Synthetic Nucleic Acid

<400> SEQUENCE: 284
ccgatatcat tgtggcagc agta                                            24

<210> SEQ ID NO 285
<211> LENGTH: 16
<212> TYPE: DNA
<213> ORGANISM: Artificial Sequence
<220> FEATURE:
<223> OTHER INFORMATION: Synthetic Nucleic Acid

<400> SEQUENCE: 285
ctccgatact aacgat                                                    16

<210> SEQ ID NO 286
<211> LENGTH: 27
<212> TYPE: DNA
<213> ORGANISM: Artificial Sequence
<220> FEATURE:
<223> OTHER INFORMATION: Synthetic Nucleic Acid
<220> FEATURE:
<221> NAME/KEY: misc_feature
```

```
<222> LOCATION: (20)..(20)
<223> OTHER INFORMATION: "K" is G or T
<220> FEATURE:
<221> NAME/KEY: misc_feature
<222> LOCATION: (21)..(21)
<223> OTHER INFORMATION: "K" is G or T

<400> SEQUENCE: 286
gcaatgagaa ggatactttk aagatta                                              27

<210> SEQ ID NO 287
<211> LENGTH: 22
<212> TYPE: DNA
<213> ORGANISM: Artificial Sequence
<220> FEATURE:
<223> OTHER INFORMATION: Synthetic Nucleic Acid

<400> SEQUENCE: 287
cggaaatttc ataacgcttt gc                                                   22

<210> SEQ ID NO 288
<211> LENGTH: 15
<212> TYPE: DNA
<213> ORGANISM: Artificial Sequence
<220> FEATURE:
<223> OTHER INFORMATION: Synthetic Nucleic Acid

<400> SEQUENCE: 288
cttccatttc ccgat                                                           15

<210> SEQ ID NO 289
<211> LENGTH: 21
<212> TYPE: DNA
<213> ORGANISM: Artificial Sequence
<220> FEATURE:
<223> OTHER INFORMATION: Synthetic Nucleic Acid

<400> SEQUENCE: 289
tcgcaacgca tacgtttgat g                                                    21

<210> SEQ ID NO 290
<211> LENGTH: 23
<212> TYPE: DNA
<213> ORGANISM: Artificial Sequence
<220> FEATURE:
<223> OTHER INFORMATION: Synthetic Nucleic Acid

<400> SEQUENCE: 290
atcaaaagca actcatcgcc atc                                                  23

<210> SEQ ID NO 291
<211> LENGTH: 14
<212> TYPE: DNA
<213> ORGANISM: Artificial Sequence
<220> FEATURE:
<223> OTHER INFORMATION: Synthetic Nucleic Acid

<400> SEQUENCE: 291
cccgtccaat ggtc                                                            14
```

METHODS OF DETECTING MULTI-DRUG RESISTANT ORGANISMS

RELATED APPLICATIONS

This application is a continuation of U.S. patent application Ser. No. 14/657,908, filed Mar. 13, 2015, which claims priority to and benefit of U.S. Provisional Patent Application No. 61/952,795, filed Mar. 13, 2014 and U.S. Provisional Patent Application No. 62/116,860, filed Feb. 16, 2015, the contents of which are each incorporated herein by reference in their entirety.

SEQUENCE LISTING

The instant application contains a Sequence Listing which has been submitted in ASCII format via EFS-Web and is hereby incorporated by reference in its entirety. Said ASCII copy, created on Aug. 6, 2018, is named OPGN-014_C01US_ST25.txt and is 71,031 bytes in size.

FIELD OF THE INVENTION

The present invention, relates generally to the identification and characterization of genes and gene families associated with multi-gene resistance in biological samples in the screening, diagnosis, therapy, epidemiological surveillance, and monitoring of multi-gene resistant colonization and infection.

BACKGROUND OF THE INVENTION

Antibiotic-resistant bacterial infections are associated with poor clinical outcomes including increased morbidity, mortality, and healthcare costs among infected patients. Colonized patients are an important reservoir of beta-lactamases leading to the transmission and spread of these organisms within hospitals and long term care facilities. The prevalence of these organisms in such facilities in the United States has steadily increased over the last 30 years. Treatment options for patients with multi-drug resistant organisms (MDROs) are extremely limited; therefore prevention of transmission within these facilities is paramount. Classical culture methods for detection of MDROs are time consuming (48-72 hours), leading to delays, inappropriate treatment and patient isolation. Highly sensitive, rapid molecular methods for detection of MDROs provide a tool for surveillance and screening of high risk patients and better patient management. The present invention addresses this market need.

Accordingly, a need exists for a rapid method that accurately differentiates between bacterial, viral, mixed and non-infectious disease patients that addresses these challenges.

SUMMARY OF THE INVENTION

The invention is based upon an ultra-sensitive method for detecting multi-drug resistant bacterial colonization or infection in a subject. In addition, the invention relates to methods for the rapid detection and characterization of MDROs, bacteria, viruses, fungi, yeasts, and molecular, phenotypic, and host biomarkers associated with infectious diseases, through high density matrix gene testing in order to provide the most comprehensive, high resolution profile of colonization, infection, and resistance pattern in a test sample. In various aspects the method includes isolating a nucleic acid sample from a biological sample obtained from the patient by amplifying the antibiotic resistant genes KPC, NDM, OXA, VIM, IMP, CTX-M and VanA by contacting the nucleic acid sample with one or more amplification primers that specifically hybridize with the each of the antibiotic resistant genes to provide an enriched nucleic acid sample; detecting the presence of the antibiotic gene by contacting the nucleic acid sample with one or more detection primers that specifically hybridize with the each of the antibiotic resistant genes to in the enriched nucleic acid sample; classifying the patient as having a multi-drug resistant bacterial colonization or infection when one or more of the antibiotic resistant genes are identified in the enriched nucleic acid sample; and providing a contact precautions recommendation for the patient having a multi-drug resistant bacterial colonization or infection. Optionally, the antibiotic resistant genes further include one or more of IMI, SME, GIM, SPM, NMC, SFC, SHV, TEM, BEL, VEB, GES, PER, SFO, BES, TLA, ACC, CMY, MIR, ACT, DHA, MOX, FOX, or CFE.

Optionally, the method further includes making a treatment recommendation for the patient. Treatment recommendation include recommending that the patient does not receive a carbapenem antibiotic when KPC, NDM, OXA, VIM, IMP, SME, SPC, IMI, NMC, or CcrA is detected; recommending that the patient does not receive a cephalosporin antibiotic when CTM-X, PER, VEB, GES, BES, SFO, TLA, TEM with amino acid substitutions E104K, R164H, R164S, R164C, G238S or E240K, or SHV with amino acid substitutions G156D, G238S or E240K, is detected recommending that the patient does not receive a beta-lactamase inhibitor-beta-lactam combination when ACC, MOX, CMY, CFE, ACT, DHA or FOX is detected; or recommending that the patient does not receive vancomycin when VanA is detected.

In some aspects the method further includes testing the biological sample to identify the phenotype of the multi-drug resistant organism and/or culturing the biological sample and confirming drug resistance.

In other aspects the invention includes methods of making a treatment recommendation for a subject known to or suspected of being colonized with or having a bacterial infection isolating a nucleic acid sample from a biological sample obtained from the patient by amplifying the antibiotic resistant genes KPC, NDM, OXA, VIM, IMP, CTX-M and VanA and optionally one or more of IMI, SME, GIM, SPM, NMC, SFC, SHV, TEM, BEL, VEB, GES, PER, SFO, BES, TLA, ACC, CMY, MIR, ACT, DHA, MOX, FOX, or CFE by contacting the nucleic acid sample with one or more amplification primers that specifically hybridize with the each of the antibiotic resistant genes to provide an enriched nucleic acid sample; detecting the presence of the antibiotic gene by contacting the nucleic acid sample with one or more detection primers that specifically hybridize with the each of the antibiotic resistant genes to in the enriched nucleic acid sample recommending that the patient does not receive a carbapenem antibiotic when KPC, NDM, OXA, VIM, SFC, IMP, SME, IMI, NMC, or CcrA is detected; recommending that the patient does not receive a cephalosporin antibiotic when CTM-X, PER, VEB, GES, BES, SFO, TLA, TEM with amino acid substitutions E104K, R164H, R164S, R164C, G238S or E240K, or SHV with amino acid substitutions G156D, G238S or E240K, is detected recommending that the patient does not receive a beta-lactamase inhibitor-beta-lactam combination when ACC, MOX, CMY, CFE, ACT, DHA or FOX is detected; or recommending that the patient does not receive vancomycin when VanA is detected.

In yet a further aspect the invention includes methods of making a treatment recommendation for a heathy subject by isolating a nucleic acid sample from a biological sample obtained from the patient; amplifying the antibiotic resistant genes KPC, NDM, OXA, VIM, IMP, CTX-M and VanA and optionally one or more of IMI, SME, GIM, SPM, NMC, SFC, SHV, TEM, BEL, VEB, GES, PER, SFO, BES, TLA, ACC, CMY, MIR, ACT, DHA, MOX, FOX, or CFE by contacting the nucleic acid sample with one or more amplification primers that specifically hybridize with the each of the antibiotic resistant genes to provide an enriched nucleic acid sample; detecting the presence of the antibiotic gene by contacting the nucleic acid sample with one or more detection primers that specifically hybridize with the each of the antibiotic resistant genes to in the enriched nucleic acid sample and recommending that the patient does not receive a carbapenem antibiotic when KPC, NDM, OXA, VIM, SFC, IMP, SME, IMI, NMC, or CcrA is detected; recommending that the patient does not receive a cephalosporin antibiotic when CTM-X, PER, VEB, GES, BES, SFO. TLA, TEM with amino acid substitutions E104K, R164H, R164S, R164C, G238S or E240K, or SHV with amino acid substitutions G156D, G238S or E240K, is detected recommending that the patient does not receive a beta-lactamase inhibitor-beta-lactam combination when ACC, MOX, CMY, CFE, ACT, DHA or FOX is detected; or recommending that the patient does not receive vancomycin when VanA is detected.

The invention further includes methods of identifying the emergence of a multi-drug resistant organism in a population of subjects identifying one or more antibiotic resistant genes selected from KPC, NDM, OXA, VIM, IMP, CTX-M and VanA and optionally one or more of IMI, SME, GIM, SPM, NMC, SFC, SHV, TEM, BEL, VEB, GES, PER, SFO, BES, TLA, ACC, CMY, MIR, ACT, DHA, MOX, FOX, or CFE in a plurality of subject samples wherein identification of an antibiotic resistant genes in the plurality of subject samples indicates the emergence of a multi-drug resistant organism in a population.

In another aspect the invention provides methods of screening a patient for multi-drug resistant bacterial colonization or infection by isolating a nucleic acid sample from a biological sample obtained from the patient such that the sample is substantially free of protein, cellular debris and or PCR inhibitors and identifying one or more antibiotic resistant genes selected from KPC, NDM, OXA, VIM, IMP, CTX-M and VanA and optionally one or more of IMI, SME, GIM, SPM, NMC, SFC, SHV, TEM, BEL, VEB, GES, PER, SFO, BES, TLA, ACC, CMY, MIR, ACT, DHA, MOX, FOX, or CFE in the sample wherein identification of an antibiotic resistant genes indicates the subject is colonized or infected with a multi-drug resistant bacterial organism.

In a further aspect the invention provides surveillance methods to establish source of the infection or colonization, comprising by extracting a nucleic acid sample from a sample collected from the environment; amplifying the antibiotic resistant genes KPC, NDM, OXA, VIM, IMP, CTX-M and VanA and optionally one or more of IMI, SME, GIM, SPM, NMC, SFC, SHV, TEM, BEL, VEB, GES, PER, SFO, BES, TLA, ACC, CMY, MIR, ACT, DHA, MOX, FOX, or CFE by contacting the nucleic acid sample with one or more amplification primers that specifically hybridize with the each of the antibiotic resistant genes to provide an enriched nucleic acid sample; detecting the presence of the antibiotic gene by contacting the nucleic acid sample with one or more detection primers that specifically hybridize with the each of the antibiotic resistant genes to in the enriched nucleic acid sample; wherein the presence of the antibiotic gene in the sample indicates the source of the infection or colonization.

The patient is at high risk for having a multi-drug resistant bacteria colonization or infection.

Contact precautions includes for example, isolating the patient to a quarantine area or ward, providing a private room for said patient, donning personal protective apparel upon entering the patient's room, limiting patient mobility, limiting or restricting access of non-colonized or non-infected patients or medical personnel to the patient, or providing dedicated patient care equipment.

Biological samples, include but are not limited to an anal swab, a rectal swab, a skin swab, nasal swab, wound swab, stool, blood, plasma, serum, urine, sputum, respiratory lavage, cerebrospinal fluid, bacteria culture or bacteria isolate, fungal culture or fungal isolate, virus culture or virus isolate.

The invention also provides kits for determining whether a patient is colonized or infected with a multi-drug resistant bacteria including a biological sample collection means; one or more primers that specifically hybridize with one or more antibiotic resistant genes selected from KPC, NDM, OXA, VIM, IMP, CTX-M and VanA and optionally one or more of IMI, SME, GIM, SPM, NMC, SFC, SHV, TEM, BEL, VEB, GES, PER, SFO, BES, TLA, ACC, CMY, MIR, ACT, DHA, MOX, FOX, or CFE; a control sample; and an instruction, wherein the instruction classifies the patient as being colonized or infected with a multi-drug resistant bacteria when one or more of the antibiotic resistant genes are identified in the sample.

In various aspect the invention provides method for implementation by one or more data processors forming part of at least one computing system by receiving, by at least one data processor, data characterizing test results of biological specimens for a patient or group of patients, wherein the test results characterize an outcome of a nucleic acid sample contacted with one or more primers that specifically hybridize with one or more antibiotic resistant genes selected from KPC, NDM, OXA, VIM, IMP, CTX-M and VanA and optionally one or more of IMI, SME, GIM, SPM, NMC, SFC, SHV, TEM, BEL, VEB, GES, PER, SFO, BES, TLA, ACC, CMY, MIR, ACT, DHA, MOX, FOX, or CFE; and generating, using at least one data processor and the received data, a database of test results for the patient or group of patients.

In further aspects the method further includes aggregating the database of test results with additional individual patient health data, patient group demographic data, healthcare institution demographic data, regional, national, or global geographic healthcare data.

The method further includes establishing, using the database of test results, colonization or infection rates and trends.

Optionally, the method further includes monitoring, using the database of test results, Hospital Acquired Infection (HAI) and death rates, CRE infection or death rates, ESBL infection or death rates.

Optionally, the method further includes establishing or augmenting, using the database of test results, treatment guidelines and policies, infection control procedures, or healthcare economic and risk management policies.

In yet a further aspect the method further includes computing, using the database of test results, baseline MDRO infection rates for a hospital and measuring the rate against a regional or national rate.

In other aspect the method further includes comprising augmenting treatment procedures, using the database of test results, to lower patient Length of Stay (LOS) in a healthcare institution, to lower overall costs, to lower patient death rates due to MDRO, to lower CMS penalties for HAIs, and to lower risk of legal settlements due to wrongful death claims.

The database of test results further includes an Electronic Health Record (EHR) or Laboratory Information Management System (LIMS).

Computer program products are also described that comprise non-transitory computer readable media storing instructions, which when executed by at least one data processors of one or more computing systems, causes at least one data processor to perform operations herein. Similarly, computer systems are also described that may include one or more data processors and a memory coupled to the one or more data processors. The memory may temporarily or permanently store instructions that cause at least one processor to perform one or more of the operations described herein. In addition, methods can be implemented by one or more data processors either within a single computing system or distributed among two or more computing system.

Unless otherwise defined, all technical and scientific terms used herein have the same meaning as commonly understood by one of ordinary skill in the art to which this invention pertains. Although methods and materials similar or equivalent to those described herein can be used in the practice of the present invention, suitable methods and materials are described below. All publications, patent applications, patents, and other references mentioned herein are expressly incorporated by reference in their entirety. In cases of conflict, the present specification, including definitions, will control. In addition, the materials, methods, and examples described herein are illustrative only and are not intended to be limiting.

Other features and advantages of the invention will be apparent from and encompassed by the following detailed description and claims.

BRIEF DESCRIPTION OF THE DRAWINGS

FIG. 1 is an illustration showing that the assay of the invention is capable of presumptively stratifying bacterial species based upon test results.

FIG. 2 is an chart showing the limits of detection (CFU/swab) of the methods of the invention FIG. 3 is a chart showing the specificity of the methods of the invention.

FIG. 4 is a chart showing the reproducibility of the methods of the invention.

FIG. 5 is a summary of genes and gene families used in the Resistome Test.

FIG. 7 illustrates the utility of the Resistome Test used in combination with DNA sequencing data to establish gene transmission profiles and events.

FIG. 8 illustrates an example of using the Resistome Test for reporting and mapping individual patient anatomical and point-source environmental data.

DETAILED DESCRIPTION OF THE INVENTION

The present invention relates to methods for the rapid detection of multi-drug resistant organisms (MDROs). The methods are useful in the detection of subjects that are colonized or infected with MDROs. Detection of MDRO colonized or infected subjects aid in infection control and the selection of appropriate antibiotic therapy.

The methods of the invention detects a broad number of genes that make up the "resistome" of organisms or the collection of antibiotic resistance in pathogeneic and non-pathogenic bacteria (FIG. 5). The methods of the invention detect beta-lactamase genes found in beta-lactam antibiotic resistant gram negative bacteria and vanomycin resistant genes found in vancomyocin resistant gram positive bacteria. More specifically the methods detect *Klebsiella pneumoniae* carbapenemase (KPC), New Delhi Metallo-beta-lactamase (NDM) Verona integron-encoded metallo-β-lactamase (VIM), IMP-type carbapenemase (IMP), OXA beta-lactamase (OXA) genes found in carbapenem resistant gram negative bacteria, CTX-M beta-lactamase (CTX-M) gene found in extended spectrum resistant gram-negative bacteria, VanA found in vancomycin resistant *Enterococcus*, IMI-type carbapenemase (IMI), SME-type carbapenemase (SME), GIM-type carbapenemase (GIM), SPM-type carbapenemase (SPM), NMC-type carbapenemase (NMC), SFC-type carbapenemase (SFC) genes found in carbapenem resistant gram negative bacteria, SHV beta-lactamase (SHV), TEM beta-lactamase (TEM), BEL beta-lactamase (BEL), VEB beta-lactamase (VEB), GES beta-lactamase (GES), PER beta-lactamase (PER), SFO beta-lactamase (SFO), BES beta-lactamase (BES), TLA beta-lactamase (TLA) genes found in extended spectrum resistant gram-negative bacteria, ACC beta-lactamase (ACC), CMY beta-lactamase (CMY), MIR beta-lactamase (MIR), ACT beta-lactamase (ACT), DHA beta-lactamase (DHA), MOX beta-lactamase (MOX), FOX beta-lactamase (FOX), or CFE beta-lactamase (CFE) genes found in AmpC-type extended spectrum resistant gram-negative bacteria. The genes detected that confer multi-gene resistance are referred to herein as "MDRO-associated genes" or "resistome genes". In addition the resistome genes can also include genes encoding efflux pumps and porins.

In addition the methods of the invention can further include the detection of numerous infectious disease organisms of biomarkers in combination with the MDRO-associated genes. For example, in some aspects *Clostridium difficile*, norovirus or Methicillin-resistant *Staphylococcus aureus* (MRSA) are detected.

Figure 6:
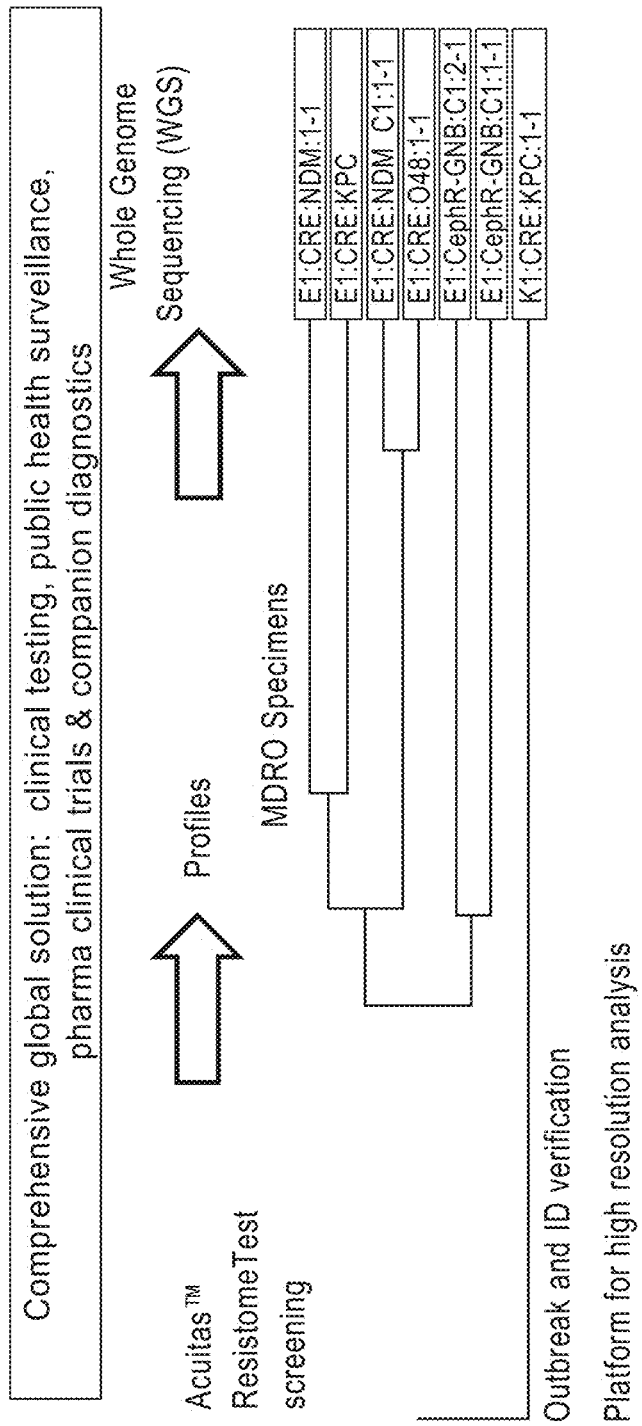
FIG. 6 illustrates the Resistome Test used as a first-line screen for establishing resistance profiles in combination with DNA sequencing for high resolution strain typing.
Figure 9:
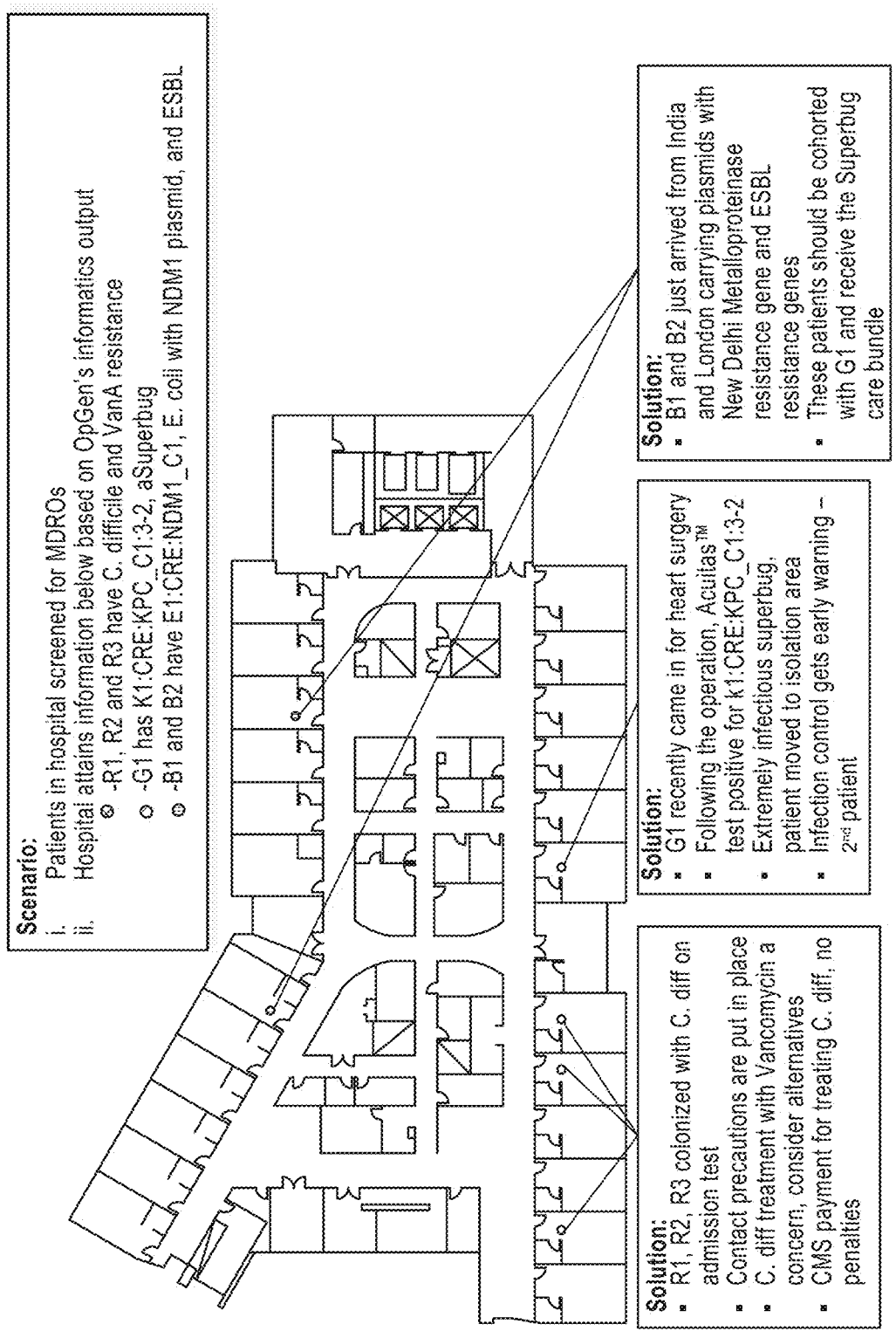
FIG. 9 illustrates an example of using the Resistome Test for reporting and mapping multiple patient data across a hospital setting.

The methods of the invention can include the detection and characterization of resistome genes and resistome gene patterns in biological samples as a first-line typing screen for subsequent higher discrimination molecular typing methods downstream for example DNA whole Genome Sequencing as part of a comprehensive solution for high resolution strain typing and mapping gene transmission events. (FIGS. 6 and 7)

KPC (*K. pneumoniae* Carbapenemase) (Class A)

A few class A enzymes, most noted the plasmid-mediated KPC enzymes, are effective carbapenemases as well. Ten variants, KPC-2 through KPC-11 are known, and they are distinguished by one or two amino acid substitutions (KPC-1 was re-sequenced in 2008 and found to be 100% homologous to published sequences of KPC-2). KPC-1 was found in North Carolina, KPC-2 in Baltimore and KPC-3 in New York. They have only 45% homology with SME and NMC/IMI enzymes and, unlike them, can be encoded by self-transmissible plasmids.

The class A *Klebsiella pneumoniae* carbapenemase (KPC) is currently the most common carbapenemase, which was first detected in North Carolina, US, in 1996 and has since spread worldwide. A later publication indicated that Enterobacteriaceae that produce KPC were becoming common in the United States.

KPC-2

Chromosomal and plasmid-mediated extended-spectrum β-lactamases (carbapanemases), identified in *Klebsiella pneumonia, Escherichia coli* and *Enterobacter* spp, *Serratia marcescens, Pseudomonas putida* and *Citrobacter freundii* worldwide. Divided into 16 subtypes i.e. KPC-1 to KPC-16. Hydrolyzes β-lactams from the penicillin (i.e. ampicillin, piperacillin, benzylpenicillin, and cloxacillin), cephalosporin (i.e. cefotaxime and ceftazidime, cephaloridine), carbapenem (i.e. iminipenen, meropenem, etrapenem, doripenem), and monobactam (i.e. aztreonam) groups at different rates. Hydrolyze oxyminio-cephalosporins more efficiently than other carbapenemases. Weakly Inhibited by clavuanic acid and tazobactam.

NDM (New Delhi Metallo-β-Lactamase) (Class B)

Originally described from New Delhi in 2009, this gene is now widespread in *Escherichia coli* and *Klebsiella pneumoniae* from India and Pakistan. As of mid-2010, NDM carrying bacteria have been introduced to other countries (including the United States and UK), most probably due to the large number of tourists travelling the globe, who may have picked up the strain from the environment, as strains containing the NDM gene have been found in environmental samples in India Ten subtypes have been reported for NDM; NDM-1 to NDM-10.

NDM-1

Highly mobile plasmid-encoded Metallo-β-lactamases (carbapanemases), carried in *Klebsiella pneumonia, Escherichia coli, Enterobacter cloacae, Acitenobacter baumanii, Pseudomonas aeruginosa* among other Enterobacteracea species worldwide. Produces up to 9 different types of β-lactamases. Shares little identity with other MBLs (i.e. VIM1/-2). Difficult to eliminate in clinical situations because hydrolyzes almost all β-lactams except for aztreonam, with no efficient inhibitor.

VIM (Verona Integron-Encoded Metallo-β-Lactamase) (Class B)

A second growing family of carbapenemases, the VIM family, was reported from Italy in 1999 and now includes 40 members, which have a wide geographic distribution in Europe, South America, and the Far East and have been found in the United States. VIM-1 was discovered in *P. aeruginosa* in Italy in 1996; since then, VIM-2—now the predominant variant—was found repeatedly in Europe and the Far East; VIM-3 and -4 are minor variants of VIM-2 and -1, respectively. VIM enzymes occur mostly in *P. aeruginosa*, also *P. putida* and, very rarely, Enterobacteriaceae. Forty gene subtypes have been reported for Amino acid sequence diversity is up to 10% in the VIM family, 15% in the IMP family, and 70% between VIM and IMP. Enzymes of both the families, nevertheless, are similar. Both are integron-associated, sometimes within plasmids. Both hydrolyse all β-lactams except monobactams, and evade all β-lactam inhibitors.

VIM-1

Highly mobile plasmid-borne integron/transposon metallo-β-lactamases, carried in *Pseudomonas aeruginosa. P. putida, Escherichia coli, Klebsiella pneumonia, Acinetobacter baumannii, Enterobacter cloacae, Serratia marcescens, Citrobacter freundii* clinical strains in North and South America, Europe and Asia. Multiple variants are found in the VIM-1, VIM-2 types. VIM-1, VIM-2 and VIM-13 share high homology. VIM-7 is distantly related to the other VIM-like metallo-β-lactamases, except for VIM-1 and VIM-2. Hydrolyzes a series of β-lactams i.e piperacillin, ceftazidime, imipenem, and aztreonam (except for VIM-2 and VIM-7 and VIM-13) at different rates. No efficient inhibitor is available.

VIM-5

Highly mobile plasmid-borne integron metallo-β-lactamases, carried in *Klebsiella pneumonia* and *Pseudomonas aeruginosa* clinical strains in Europe. The highest identity is shared with VIM-1 and VIM-2. Hydrolyzes imipenem, meropenem, aztreonam, ceftazidime, piperacillin, piperacillin-tazobactam, cefepime, ciprofloxacin, tobramycin, amikacin and gentamicin. No efficient inhibitor is available.

Forty gene subtypes have been reported for VIM, these include VIM1-VIM40

IMP-Type Carbapenemases (Metallo-β-Lactamases) (Class B)

Plasmid-mediated IMP-type carbapenemases, 48 varieties (IMP 1-IMP48) of which are currently known, became established in Japan in the 1990s both in enteric Gram-negative organisms and in *Pseudomonas* and *Acinetobacter* species. IMP enzymes spread slowly to other countries in the Far East, were reported from Europe in 1997, and have been found in Canada and Brazil.

IMP-1/IMP-2

Chromosomal and plasmid-borne integron Metallo-β-lactamases (carbapanemase), identified in *Klebsiella pneumoniae, Pseudomonas aeruginosa, P. putida, Serratia marcescens, Acitenobacter baumannii, Citrobacter freundii, Enterobacter cloacae, E. aerogenes, Proteus vulgaris, Providencia rettgeri* and *Shigella flexneri* in Asia, North and South America, and Europe. Multiple variants are found in the IMP-1- and IMP-2-types. Hydrolyzes carbapenems (including imipenen and meropenem), penicillims, monobactams, fluroquinones (i.e. ciprofloxacin), cephalosporins (i.e. cephalorodin, cefoxitin, cefepime) and aminoglycosides (i.e amikacin) at different rates. No efficient inhibitor is available.

IMP-5

Highly mobile plasmid-encoded metallo-β-lactamases carried in *Acinetobacater baumanni* clinical strains in Europe. Shows greater homology with IMP-1, IMP-3 and IMP-4 than with IMP-2. Hydrolyzes penicillins, broad-spectrum cephalosporins, including ceftazidime, ceftriaxone, cefepime, cefpirome, and to aztreonam, but not ampicillin/sulbactam, aminoglycosides and quinolone.

OXA Beta-Lactamases (Class D)

OXA beta-lactamases were long recognized as a less common but also plasmid-mediated beta-lactamase variety that could hydrolyze oxacillin and related anti-staphylococcal penicillins. These beta-lactamases differ from the TEM and SHV enzymes in that they belong to molecular class D and functional group 2d. The OXA-type beta-lactamases confer resistance to ampicillin and cephalothin and are characterized by their high hydrolytic activity against oxacillin and cloxacillin and the fact that they are poorly inhibited by clavulanic acid. Amino acid substitutions in OXA enzymes can also give the ESBL phenotype. While most ESBLs have been found in *E. coli, K pneumoniae*, and other Enterobacteriaceae, the OXA-type ESBLs have been found in *P. aeruginosa* and *Acinetobacter buamannii*. OXA-type ESBLs have been found mainly in *Pseudomonas*

*aeruginosa* isolates from Turkey and France. The OXA beta-lactamase family was originally created as a phenotypic rather than a genotypic group for a few beta-lactamases that had a specific hydrolysis profile. Therefore, there is as little as 20% sequence homology among some of the members of this family. However, recent additions to this family show some degree of homology to one or more of the existing members of the OXA beta-lactamase family. Some confer resistance predominantly to ceftazidime, but OXA-17 confers greater resistance to cefotaxime and cefepime than it does resistance to ceftazidime.

OXA-2

Plasmid encoded oxacillinase family (i.e. OXA-2, OXA-15 and OXA-32), identified in *Salmonella typhimurium* and *Pseudomonas aeruginosa* clinical isolates in Europe. Hydrolyzes benzylpenicillin, penicillim, ampicillim, oxacillim, cephaloridine, cephalothin, and ceftazidime (hydrolysis rates varies within the family members). Well-inhibited by azobactam, but weakly inhibited by clavulanic acid.

OXA-10

Plasmid-encoded oxacillinase family (i.e. OXA-14, OXA-16, and OXA-17), identified in *Pseudomonas aeruginosa* clinical isolates in Europe. Hydrolyzes penicillim, ampicillim, cabenicillim, cloaxicillim, oxacillim, and cephaloridine, cefotaxime, ceftriaxone among others (hydrolysis rates varies within the family members).

OXA-18

Chromosomal-encoded oxacillinase, identified in *Pseudomonas aeruginosa* clinical isolates in Europe. Shares weak identity with all class D β-lactamase except OXA-9 and OXA-12. Hydrolyzes amoxicillin, ticarcillin, cephalothin, ceftazidime, cefotaxime, and aztreonam, but not imipenem or cephamycins.

OXA-23

Chromosomal and Plasmid-encoded oxacillinase, identified in *Acinobacter bumannii, Acinetobacter junii, A. radioresistens, Proteus mirabilis* clinical isolates in Europe, Australia, Asia, North and South America. Closely related to OXA-27. Hydrolyzes ampicillin, cefotaxime, ceftazidime, gentamicin, piperacillin, piperacillin-tazobactam, and to a lesser extend amikacin, ciprofloxacin, imipenem and meropenem.

OXA-24

Chromosomal-encoded oxacillinase, identified in *Acinobacter bumannii* in clinical isolates in Europe. Shows distant homology with OXA-10, OXA-7, and OXA-11. Hydrolyzes benzylpenicillin, ampicillin, cephaloridine, tircarcilin, imipenem and meropenem, but lack activity against oxacillin, cloxacillin and methicillim. Inhibitied by NaCl, tazobactam, sulbactam and clavulanic acid.

OXA-45

Plasmid-encoded oxacillinase, carried in *Pseudomonas aeruginosa* clinical strains in North America. Shares some enzyme homology with OXA-18, OXA-9, OXA-22, OXA-12 and OXA-29. Hydrolyzes ceftazidime, aztreonam (high levels), and cefotaxime (low level). Inhibited by NaCl, imipenem, and clavulanic acid.

OXA-48

Plasmid-encoded oxacillinase, carried in *Klebsiella pneumoniae* clinical strains in Turkey. Remotely related to other oxacillinases. Hydrolyzes carbapenems at a level much higher than other oxacillinases as well as penicillims and imipenes, but not expanded-spectrum cephalosporins. Well-inhibited by NaCL and weakly inhibited by clavulanic acid, tazobactam, and sulbactam.

OXA-50

Chromosomal-encoded oxacillinase, identified in *Pseudomonas aeruginosa* clinical strains in Europe. Hydrolyzes ampicillin, benzylpenicillin, cephaloridine, cephalothin, nitrocefin, piperacillin, and iminipen to low levels, but not oxackillin or cloxacillin. Hydrolyzes ampicillin, benzylpenicillin, cephaloridine, cephalothin, nitrocefin, piperacillin and imipenem (low level).

OXA-51

Chromosomal-encoded oxacillinase, identified in *Klebsiella pneumoniae, Acinobacter bumannii* isolates in North and South America, Europe, and Asia. Hydrolyzes impenem, cefepime, ceftazidime, piperacillin, piperacillin/tazobactam, aztreonam, ciprofloxacin and amikacin.

OXA-54

Chromosomal-encoded oxacillinase, identified in *Pseudomonas aeruginosa Shewanella oneidensis* strains in Europe. Shares high homology with OXA-48. Hydrolyzes imipenen (significantly high), penicillins, cephalothin, cefpirome, and to a lesser extend cefuroxime, cefotaxime, meropenen and cefepime. Do not hydrolyze ceftazidime and aztreonam. Well-inhibited by NaCl, but weakly inhibited by clavulanic acid, tazobactam, and sulbactam.

OXA-55

Chromosome-encoded oxacillinase, identified in *Shewanella algae* clinical isolates in Europe. No significant identity exists between OXA-55 and other oxacillinases. Hydrolyzes benzylpenicillim, amplicillin amoxicillin, ticarcillin, peperacillin, oxacillin, cloxacillin, cephalothin, cephaloridine, cepirone, and iminipen and meropen (low levels). Inhibited by clavulanic acid, tazobactam, and sulbactam.

OXA-58

Plasmid-encoded oxacillinase, carried in *Acinobacter baumannii, Acinobacter junii* and *Acinobacter* spp. clinical isolates in North South America, Europe, Asia, and Oceania. Weakly related to other oxacillinase genes. Hydrolyzes penicillins, oxacillin, and imipenem (low levels), but not ceftazidime, cefotaxime, and cefepime. Weakly inhibited by clavulanic acid, tazobactam, and sulbactam.

OXA-60

Chromosome-encoded oxacillinase, identified in *Ralstonia pickettii* strains in Europe. Shows a greater homology with OXA-50 than other oxacillinases. Hydrolyzes benzylpenicillin, amoxicillin, piperacillin, ticarcillin, nitrocefin, oxacillin, cloxacillin. Well-inhibited by NaCl, but weakly inhibited by clavulanic acid, and tazobactam.

OXA-620

Chromosome-encoded oxacillinase, identified in *Pandoraea pnomenusa* clinical strains. Shows a greater homology with OXA-50 than other oxacillinases. Hydrolyzes penicillins, oxacillin, imipenem, and meropenem, but not expanded-spectrum cephalosporins. Well-inhibited by NaCl, but weakly inhibited by clavulanic acid, and tazobactam.

CTX-M Beta-Lactamases (Class A)

CTX-M

Chromosomal and plasmid-encoded extended-spectrum β-lactamases, identified mostly in *Escherichia coli* clinical strains worldwide. Divided into 5 phylogenetic groups based on aminoacid identity i.e. CTX-M-1 group (including 41 members), the CTX-M-2 group (including 15 members), the CTX-M-8 group (including more than 3 members), the CTX-M-9 group (including 43 members), and the CTX-M-25 group (with more than 4 members). Closer related to the β-lactamases of *Kluyvera* spp. Hydrolyzes cefotaxime and ceftazidime at high rates, but several enzymes, such as CTX-M-15 and CTX-M-19, also hydrolyze ceftazidime efficiently which may complicate the phenotypic identification of CTX-Ms. More than 80 CTX-M enzymes are currently known.

Van-A

Six different types of vancomycin resistance are shown by *enterococcus*: Van-A, Van-B, Van-C, Van-D, Van-E and Van-F. Of these, only Van-A, Van-B and Van-C have been seen in general clinical practice, so far. The significance is that Van-AVRE is resistant to both vancomycin and teicoplanin. The mechanism of resistance to vancomycin found in *enterococcus* involves the alteration to the terminal amino acid residues of the NAM/NAG-peptide subunits, under normal conditions, D-alanyl-D-alanine, to which vancomycin binds. The D-alanyl-D-lactate variation results in the loss of one hydrogen-bonding interaction (four, as opposed to five for D-alanyl-D-alanine) being possible between vancomycin and the peptide. This loss of just one point of interaction results in a 1000-fold decrease in affinity. The D-alanyl-D-serine variation causes a six-fold loss of affinity between vancomycin and the peptide, likely due to steric hindrance.

ACC-1

Plasmid-mediated AmpC type β-lactamase (cephalosporinases), carried in *Klebsiella pneumonia, Escherichia coli, Proteus mirabilis*, and *Salmonella* spp. in Europe and Africa. Shows distant amino acid sequence homology with known AmpC β-lactamases. Closely related to the chromosomally encoded AmpC-type β-lactamase of *Hafnia alvei*. Hydrolyzes ampicillin, cefazolin, cefuroxime, cefotaxime, ceftazidime, amoxicillin-clavulanate, kanamycin, tobramycin, tetracycline, and trimethoprim-sulfamethoxazole. Poorly inhibited by tazobactam.

ACT-1/MIR-1

ACT-1 and MIR-1 are both plasmid-mediated AmpC type β-lactamases (Cephamycinases), carried in *Escherichia coli* and *Klebsiella pneumonia* in the US. ACT-1 is highly homologous with MIR-1 and both ACT-1 and MIR-1 share high homology with the chromosomal ampC genes of *Enterobacter cloacae*. ACT-1 hydrolyzes cefepime and cefoxitin. MIR-1 hydrolyzes cephalothin, ceftazidime, cefoxitin, cefotetan, cefmetazole, moxalactam, aztreonam, ampicillin and carbenicillin.

BEL-1

Rare chromosome-encoded β-lactamase, identified in *Pseudomonas aeruginosa* clinical strains in Belgium. Weakly related to GES-1 and BES-1. Hydrolyzes most expanded-spectrum cephalosporins at high levels (excluding cephamycins and carbapenems) and aztreonam. Well-inhibited by clavunate, cefoxitin, moxalactam and imipenen, but poorly inhibited by tazobactam.

BES-1

Rare plasmid-encoded β-lactamase, carried in a single *Serratia marcescens* clinical strain in Brazil. Shares some identity with the CTX-M group 1 β-lactamase. Hydrolyzes aztreonam, cefotaxime and ceftazidime (high levels). Well-inhibited by clavulanic acid, but poorly inhibited by tazobactam.

CMY-2/CFE-1

CMY-2 and CFE-1 are both plasmid-mediated AmpC type β-lactamases (Cephamycinases), carried in *Escherichia coli* and *Klebsiella pneumonia* in Asia and Europe. CMY-2 is highly homologous with CFE-1 and BIL-1, and both CMY-2 and CFE-1 share high homology with CMY-3/-4, LAT-1/-3 and the chromosomal ampC genes of *Citrobacter freundii*. CMY-2 hydrolyzes cefoxitin, cefotetan, ceftibuten, aztreonam, and flomoxef. CFE-1 hydrolyzes cephalothin and cefpodoxime. Both CMY-2 and CFE-1 hydrolyze ceftazidime, cefotaxime, piperacillin, and cefametazole.

DHA-1

Plasmid-mediated AmpC type β-lactamase (Cephalosporinase), carried in *Salmonella enteritidis* clinical isolates in Saudi Arabia. Highly homologous with the chromosome-mediated cephalosporinase of *M. morganii*. Hydrolyzes amoxicillim, amoxicillin plus clavulanic acid, ticarcillin, cephalothin, cefoxitin, cefoxatime, ceftazidime, and moxalactam, but not iminipen. Inhibited by low concentrations of aztreonam, cefoxitin, or cloxacillin and only by high concentrations of clavulanic acid.

FOX-1

Plasmid-mediated AmpC type β-lactamase (cephalosporinases), carried in *Klebsiella pneumonia* in Argentina. Highly homologous with FOX-2/-3. Hydrolyzes ampicillin, carbenicillin, cephalothin, cephaloridine, ceftazidime, cefotaxime, cefoxitin, cefotetan, and cefmetazole. Well-inhibited by cloxacillin and aztreonam, but poorly inhibited by clavulanic acid, tazobactam, and sulbactam.

GIM-1

Mobile plasmid-borne integron Metallo-β-lactamase, carried in *Pseudomonas aeruginosa* clinical isolates in Germany. Shares distant homology with IMP, VIM and SPM-1 enzymes. Hydrolyzes imipenem, meropenem, ceftazidime, cefepime, and piperacillin-tazobactam. Does not hydrolyze azlocillin, aztreonam, and the serine lactamase inhibitors.

GES-1

Plasmid- and integron-encoded β-lactamase, carried in *Klebsiella pneumoniae* clinical isolates in France. Hydrolyzes penicillins and expanded-spectrum cephalosporins, but not cephamycins, carbapenems, and aztreonam. Inhibited by clavulanate, tazobactam and imipenem.

IMI-1/NMCA-1

IMI-1 and NMCA-1 are both chromosomal-encoded β-lactamases, identified in *Enterobacter cloacae* clinical isolates in North America and Europe. IMI-1 shares high homology with the NMC-A and NMC-R genes, and may be considered NMC-type β-lactamase. IMI-1 hydrolyses cefotaxime and ceftazidime less fast than NMC-A, imipenem (high levels) and benzylpenicillin (modest rates), but more slowly than cephaloridine. NMCA-1 also hydrolyzes ampicillin, amoxicillin-clavulanic acid, cefazolin, and cefoxitin. In contrast to NMCA-1, IMI-1 is inhibited more effectively by tazobactam than by clavulanic acid.

MOX-1/CMY-1

CMY-1 (Cephamycinase), and MOX-1/MOX-5 (moxalactamases) are all plasmid-mediated AmpC type β-lactamases, carried in *Escherichia coli* and *Klebsiella pneumonia* in Asia and Africa. CMY-1 shares high homology with MOX-1/MOX-5, and all of them are highly homologous with both FOX-1 and the chromosomal AmpC β-lactamase of *Pseudomonas aeruginosa*. CMY-1 hydrolyzes cefoxitin, ceftriaxone, cefotaxime, Cefametazole, cefotetan, flomoxef, gentamicin, amikacin, nalidixic acid, ciprofloxacin, norfloxacin, piperacillin, and co-trimoxazole to a lesser extent. MOX-1/MOX-5 hydrolyzes ampicillim, cefoxaine, aztreonam, and cefotetan. CMY-1 and MOX-1/MOX-5 are inhibited by clavulanic acid, sulbactam and tazobactam.

PER-1

Plasmid-encoded β-lactamase, carried in *Pseudomonas aeruginosa, Acinetobacter* spp., *A. baumannii, Salmonella enterica* serovar *Typhimurium* and *Providencia rettgeri, P. stuartii* and *Proteus mirabilis* in Europe and Asia. Shares significant homology with VEB-1 and TLA-1 enzymes, which belong to the 'Per-like family'. Hydrolyzes penicillins, cefotaxime, ceftazidime, and aztreonam, but spares carbapenems and cephamycins. Well-inhibited by clavulanic acid, sulbactam and tazobactam.

SFC-1

Chromosomal-encoded-β-lactamase, identified in *Serratia fonticola* strains from hospitals in Europe. Hydrolyzes penicillins, cephalosporins, aztreonam, and carbapenems and is inhibited by clavulanic acid, sulbactam, and tazobactam. Less inhibited by class A β-lactamase inhibitors than other group of carbapenemases.

SIM-1

Mobile plasmid-encoded Metallo-β-lactamase, carried in *Acinetobacter baumannii* clinical isolates from Korea. More closely related to IMP-type enzymes than to other MBLs. Hydrolyzes a broad array of β-lactams (i.e. penicillims, cephalosporins, and carbapenems). Exhibits relatively low imipenen and meropenem MICs. Not active against taztrenoman and piperacillin.

SME-1

Chromosomal-encoded-β-lactamase, identified in *Serratia marcescens* and *E. coli* clinical strains from England and US. Hydrolyses a variety of lactams from the penicillin, cephalosporin, monobactam, and carbapenem groups.

SHV-G238/E240

Chromosomal and plasmid-encoded, narrow spectrum β-lactamase SHV-1 parental type. Possesses glycine at position 238 and glutamic acid at 240 position. Carried mainly in multiple strains of *Klebsiella pneumoniae* in Europe. Hydrolyzes a narrow-spectrum of cephalosporins, penicillims and aztreonam. Inhibited by clavulanic acid.

SHV-G238S/E240

Plasmid-encoded SHV-type extended spectrum β-lactamase harboring mutation G38S (glycine at position 238 in SHV-1 is replaced by serine in SHV-2, -3, -20, -21, -30, -34, -39, -106, -141, -152, -153, -162, and -163). Carried mainly in *Klebsiella pneumonia, Escherichia coli, Serratia marcescens* and *Salmonella typhimurium* in Europe, Asia and South-Africa. SHV-2 hydrolyzes cefoxitin, cefotaxime, ceftazidime, ceftazidime-clavulanate, piperacillin-tazobactam, meropenem (high levels) and imipenem (intermediate level).

SHV-G238/E240K

Plasmid-encoded SHV-type extended spectrum β-lactamase harboring mutation E240K (glutamic acid at position 240 in SHV-1 replaced by lysine in SHV-31, -91, -97, -115, and -120). Carried mainly in *Klebsiella pneumonia* clinical strains in Europe. SHV-31 hydrolyzes ceftazidime, cefotaxime, and aztreonam, gentamicin, ciprofloxacin, and levofloxacin, but not cefepime and amikacin. Inhibited by clavulanic acid.

SHV-G238S/E240K

Plasmid-encoded SHV-type extended spectrum β-lactamase harboring double mutation G238S and E240K (glycine at position 238 and glutamic acid at position 240 in SHV-1 is replaced by serine and lysine, respectively in SHV-4, -5, -6, -7, -8, -9, -10, -12, -15, -22, -23, -45, -46, -55, -64, -66, -90, -105, -123, -124, -128, -129, 134, -154, -160, -165 and -183). Carried mainly in *Klebsiella pneumonia, Enterobacter* spp. and *Escherichia coli* clinical strains in US, Africa and Europe. SHV-5 hydrolyzes amoxicillin, ticarcillin, piperpacillin, cephalexin, cephalothin, cefamandole, cefatzidime, ceftazidime, aztreonam, tigernoman (high levels) plus caruomonan and cefoxitin (intermediate levels). Inhibited by clavulanic acid, sulbactam and tazobactam.

SHV-G156

Chromosomal and plasmid-encoded, narrow spectrum β-lactamase SHV-1 parental type. Possesses glycine at position 156 position. Identified in multiple clinical strains of *Klebsiella pneumonia* in Europe. Carried mainly in multiple strains of *Klebsiella pneumoniae* in Europe. Hydrolyzes a narrow-spectrum of cephalosporins, penicillims and aztreonam. Inhibited by clavuanic acid.

SHV-G156D

Plasmid-encoded SHV-type extended spectrum beta-lactamase harboring mutation G156D. Glycine at amino acid position 156 in SHV-1 replaced by aspartic acid in SHV-27, -32, -45, -93, -105, -110 and -177. Hydrolyzes amoxicillin, gentamicin, cefotaxime, ceftazidime, aztreonam and trimethoporim. Inhibited by clavuanic acid (Corkill et al, 2001). Carried by *Klebsiella pneumonia* in South America and Europe.

SFO-1

Rare self-transferable plasmid encoded β-lactamase, carried in a single clinical *Enterobacter cloacae* isolate in Japan. Hydrolyzes cefoxatime very efficiently, and spares cephamycins and carbapenems, but not cephamycins. Inhibited by clavulanic acid and imipenen.

SPM-1

Plasmid-encoded metallo-β-lactamases, carried in *Pseudomonas aeruginosa* clinical strains from Brazil. Represents a subfamily of mobile metallo-β-lactamase different from VIM and IMP. Hydrolyzes cloxacillin, oxacillin, penicillin, ampicillin, imipenem, meropenem, cefaloridine, ceftazidime and nitrocefin, and no inhibitor is clinical available.

TEM-E104

Plasmid-encoded transposable element β-lactamase TEM-1 parental type. Possesses glutamic acid at position 104. Commonly found in gram negative bacteria, mainly in *Escherichia coli* and *Klebsiella pneumoniae*. Hydrolyzes 90% of the penicillim-type antibiotics. Inhibited by clavuanic acid.

TEM-E104K

Plasmid-encoded TEM-type extended spectrum β-lactamase harboring mutation E104K (glutamic acid at position 104 in TEM-1 replaced by lysine in TEM-3, -4, -6, -8, -9, -15, -16, -17, -18, -21, -22, -24, -26, among other 39 more TEM-type variants). Carried mainly in *Klebsiella pneumoniae, Escherichia coli, Salmonella typhimurium, Salmonella* spp. in North America, Europe and Africa. TEM-3 hydrolyzes amikacin, netilmicin, tobramycin, tetracycline, sulphonamides ampicillim and gentamycin (high levels) plus trimethoprim-sulfamethoxazole (low level).

TEM-R164

Plasmid-encoded transposable element β-lactamase TEM-1 parental type. Possesses arginine acid at position 164. Commonly found in gram negative bacteria, mainly in *Escherichia coli* and *Klebsiella pneumoniae*. Hydrolyzes 90% of the penicillim-type antibiotics. Inhibited by clavuanic acid. Carried mainly in *Klebsiella pneumoniae* and *Escherichia coli* in North America and Europe.

TEM-R164H

Plasmid-encoded TEM-type extended spectrum β-lactamase harboring mutation R164H (arginine acid at position 104 in TEM-1 replaced by histidine in TEM-6, -11, -16, -27, -28, -29, -43, -61, -75, -107, -109, -115, -118, -132, -134, -147, -151, -152, -161, and -187). Carried mainly in *Klebsiella pneumoniae* and *Klebsiella oxytoca* in North America. TEM-115 hydrolyses ceftazidime, gentamicin and tobramycin (moderate levels). Inhibited by clavuanic acid (low level).

TEM-R164C

Plasmid-encoded TEM-type extended spectrum β-lactamase harboring mutation R164C (arginine acid at position 104 in TEM-1 replaced by asparatic acid in TEM-87, -91, -143, -144, -193, and -195). Carried mainly in *Klebsiella pneumoniae, Escherichia coli*, and *Proteus mirabilis* in Europe. TEM-87 hydrolyzes ampicillin, amoxicillin-clavulanate, piperacillin, cefazolin, ceftazidime, cefepime and aztreonam. Inhibited by clavuanic acid.

TEM-R164S

Plasmid-encoded TEM-type extended spectrum β-lactamase harboring mutation R164S (arginine acid at position 104 in TEM-1 replaced by serine in i.e. TEM-5, -7, -8, -9, -10, -12, -24, -26, -46, -53, -60, -85, -86, -102, -114, -121, -125, -129, -130, -131, -133, -136, -137, -149, -154, - 155, -158, -165, -177, -184, and -205). Carried mainly in *Klebsiella pneumoniae* and *Citrobacter freundii* clinical isolates in Europe. TEM-7 hydrolyzes ampicillin, piperacillin, ceftazidime and aztreonam but not other third-generation cephalosporins. Inhibited by clavuanic acid.

TEM-G238/E240

Plasmid-encoded transposable element β-lactamase TEM-1 parental type. Possesses glycine at position 238 and glutamic acid at 240 position. Commonly found in gram negative bacteria, mainly in *Escherichia coli* and *Klebsiella pneumoniae*. Hydrolyzes 90% of the penicillim-type antibiotics. Inhibited by clavuanic acid.

TEM-G238/E240K

Plasmid-encoded TEM-type extended spectrum β-lactamase harboring mutation E240K (glutamic acid at position 240 in TEM-1 replaced by lysine in TEM-5, -10, -24, -27, -28, -46, -61, -85, -86, -91, -114, -121, -136, -144, -152, -155, -177, and -191). Carried mainly in *Klebsiella pneumoniae* in the US. TEM-10 hydrolyzes cephaloridine, benzylpenicillim, amipicillim, piperacillin, ceftazidime, and aztreonam. Inhibited by p-chloromercuribenzoate.

TEM-G238S/E240

Plasmid-encoded TEM-type extended spectrum β-lactamase harboring mutation G38S □glycine at position 238 in TEM-1 is replaced by serine in TEM-3, -4, -8, -15, -19, -20, -21, -22, -25, -50, -52, -66, -88, -89, -92, -94, -107, -112, -113, -120, -123, -134, -138, -139, -167, -197, -199, and -211). Carried mainly in *Klebsiella pneumoniae* and *Escherichia coli* in Asia. TEM-19-20, and -52 hydrolyzes ampicillin, cephalothin, ceftazidime, and aztreonam, and cefotaxime.

TEM-G238S/E240K

Plasmid-encoded TEM-type extended spectrum β-lactamase harboring double mutation G238S and E240K (glycine at position 238 and glutamic acid at position 240 in TEM-1 is replaced by serine and lysine, respectively in TEM-42, -47, -48, -49, -68, -71, -72, -93, -101, and -188). Carried mainly in *Klebsiella pneumoniae* and *Pseudomonas aeruginosa* in Europe. TEM-42 hydrolyzes penicillim, cephaloridine, and cefotaxime. Inhibited by clavuanic acid.

TLA-1

Rare self-transferable plasmid encoded β-lactamase, carried in *Escherichia coli* and *Klebsiella pneumoniae* clinical isolates in a single Indian tribe in Mexico. Shares significant homology with VEB-1 and PER-1 enzymes. Hydrolyzes expanded-spectrum cephalosporins, including cefotaxime, ceftazidime, aztreonam and cefepime, but not imipenem and cefoxitin. Strongly inhibited by tazobactam, and to a lesser extent, by clavulanic acid and sulbactam.

VEB-1

Plasmid- and integron-encoded β-lactamase, carried in clinical strains in *Pseudomonas aeruginosa, P. stuartii Escherichia coli, Acinetobacter baumannii* isolates, *Providencia stuartii, Enterobacter cloacae* and *A. xylosoxidans* isolates in South America, Africa, Asia, and Europe. Shares some enzyme homology with PER-1 and -2. Hydrolyzes ceftazidime, cefotaxime, aztreonam and quinolones (high levels) plus penicillim (low levels). Inhibited by clavulanate, sulbactam and tazobactam, moxalactam, imipenem and cefoxitin.

MDRO-Associated Genes

The genes detected that confer multi-gene resistance are referred to herein as MDRO-associated genes or resistome genes and encompass one or more genes or gene families of KPC, NDM, VIM, IMP, OXA, CTX-M, Van-A, IMI, SME, GIM, SPM, NMC, SFC, SHV, TEM, BEL, VEB, GES, PER, SFC, BES, TLA, ACC, CMY, MIR, ACT, DHA, MOX, FOX, or CFE. In preferred methods one or more gene or gene families of KPC, NDM, VIM, IMP, OXA, CTX-M, or Van-A are detected. In various aspects, the genes includes all family members. For example, by KPC it is meant to include KPC 2-KPC-16. By OXA it is meant to include OXA-48, 23, 51, 2, 10, 18, 24, 45, 50, 54, 55, 58, 60, and 62. Exemplary MDRO-associated genes useful in the practice of the methods of invention include but are not limited to the genes listed on Table 1.

As exemplified in detail in Table 1, as used herein, when reference is made to a gene abbreviation (e.g. KPC, OXA, VIM, etc) it is meant to include at least one and up to all subtypes. For example when reference is made to KPC it is meant to include at least one and up to all subtypes (e.g. KPC-2 through KPC-16) of KPC. As used herein, when reference is to be made to a subset of subtypes the gene abbreviation is followed by a number (e.g., VIM-1, VIM-5, OXA-2). For example when reference is made to OXA-2 it is meant to include OXA-2, 15, 32.)

TABLE 1

| Gene Family | Gene Subtypes |
| --- | --- |
| KPC | KPC-2 through KPC-16 |
| NDM | NDM-1 through NDM-9 |
| VIM-1 | VIM-1, 2, 3, 4, 6, 8, 9, 10, 11, 12, 13, 14, 15, 16, 17, 18, 19, 23, 24, 26, 27, 28, 29, 31, 32, 33, 34, 35, 36, 37, 39 |
| VIM-5 | VIM-5, 25, 38 |
| OXA-2 | OXA-2, 15, 32 |
| OXA-10 | OXA-10, 14, 16, 17 |
| OXA-18 | OXA-18 |
| OXA-23 | OXA-23, 49, 73, 146, 165, 167, 168, 169, 170, 171, 225, 239 |
| OXA-24 | OXA-24, 25, 26, 40, 72, 139, 160, 207 |
| OXA-45 | OXA-45 |
| OXA-48 | OXA-48, 162, 163, 181, 199, 204, 232, 244, 245, 247 |
| OXA-50 | OXA-50 |
| OXA-51 | OXA-51, 64, 65, 66, 67, 68, 69, 70, 76, 77, 78, 80, 82, 83, 84, 86, 87, 88, 89, 90, 91, 92, 93, 94, 95, 98, 99, 100, 106, 107, 108, 109, 110, 111, 113, 115, 120, 128, 130, 132, 138, 144, 148, 149, 150, 174, 175, 176, 177, 178, 179, 180, 194, 195, 196, 197, 201, 202, 206, 208, 216, 217, 219, 223, 242, 248, 249, 254 |
| OXA-54 | OXA-54 |
| OXA-55 | OXA-55 |
| OXA-58 | OXA-58, 97 |
| OXA-60 | OXA-60 |
| OXA-62 | OXA-62 |
| CTX-M-1 | CTX-M-1, 3, 11, 12, 15, 22, 23, 28, 32, 33, 36, 42, 52, 54, 55, 57, 58, 60, 61, 64, 69, 71, 72, 79, 82, 88, 96, 101, 103, 107, 108, 109, 114, 117, 123, 132, 133, 136 |
| CTX-M-2 | CTX-M-2, 5, 20, 31, 43, 44, 56, 59, 76, 77, 92, 95, 97, 131 |
| CTX-M-8/25 | CTX-8, 25, 26, 39, 40, 41, 63, 78, 89, 91, 94, 100 |
| CTX-M-9 | CTX-9, 13, 14, 16, 17, 18, 19, 21, 24, 27, 38, 46, 47, 48, 49, 50, 51, 65, 67, 81, 82, 83, 84, 85, 86, 90, 93, 98, 99, 104, 106, 110, 111, 112, 113, 121, 122, 123, 125, 126, 129, 130, 134, 147 |

TABLE 1-continued

| Gene Family | Gene Subtypes |
| --- | --- |
| IMP-1 | IMP-1, 3, 4, 6, 10, 25, 26, 30, 34, 38, 40, 42 |
| IMP-2 | IMP-2, 8, 14, 16, 18, 19, 20, 24, 32, 33 |
| IMP-5 | IMP-5 |
| BEL | BEL-1, 2, 3 |
| CMY-2/ CFE-1 | CMY-2, 4, 5, 6, 7, 12-18, 20-40, 42-46, 49, 53-64, 69, 71, 73, 77, 80, 94, 95, 99, 102, 108, 111 and CFE-1 |
| CMY-41 | CMY-41, 47, 48, 50, 51, 65-68, 72, 75, 76, 78, 79, 81, 84, 87, 90, 103, 110 |
| CMY-70 | CMY-70, 74, 83, 93, 100, 101 |
| GES | GES-1 through GES-17 |
| GIM | GIM-1 |
| IMI-1/ NMC-A | IMI-1, 2, 3, 4, 7 and NMC-A |
| PER | PER-1, 3, 4, 5, 7, 8 |
| SME | SME-1 through SME-5 |
| SPM | SPM-1 |
| VEB | VEB-1 through VEB-9 |
| ACC-1 | ACC-1, 2, 4 |
| ACC-3 | ACC-3 |
| ACT-1/ MIR-1 | ACT-1, 2, 3, 4, 5, 6, 7, 10, 13, 14-21, 23, 35 and MIR-1, 2, 3, 4, 5, 6 |
| DHA | DHA-1, 2, 3, 5, 6, 7 |
| FOX | FOX-1 through FOX-10 |
| MOX-1/ CMY-1 | MOX-1, 2, 3, 4, 5, 6, 7, 8 and CMY-1, 8, 9, 10, 11, 19 |
| TLA | TLA-1 |
| BES | BES-1 |
| SFC | SFC-1 |
| SIM | SIM-1 |
| SHV-G156 | SHV-1-26, 28-31, 33-44, 46-92, 94-104, 106, 109, 111-176, 178-190 |
| SHV-G156D | SHV-27, 32, 45, 93, 105, 110, 177 |
| SHV-G238/ E240 | SHV-1, 6, 8, 11, 14, 16, 17, 19, 24-28, 32, 33, 35-39, 40-44, 47-54, 56-63, 65, 67-85, 87-89, 92-96, 98-101, 103-104, 107-114, 116-119, 121, 122, 125, 127, 130-133, 135-140, 142-151, 155-159, 161, 164, 166-182, 184-188, 190 |
| SHV-G238S/ E240 | SHV-2, 2A, 3, 20, 21, 30, 34, 39, 106, 141, 152, 153, 162, 163, |
| SHV-G238/ E240K | SHV-31, 91, 97, 115, 120, 126, |
| SHV-G238S/ E240K | SHV-4, 5, 7, 9, 10, 12, 15, 22, 23, 445, 46, 55, 64, 66, 90, 105, 123, 124, 128, 129, 134, 154, 160, 165, 183 |
| TEM-E104 | TEM-1, 2, 5, 7, 10, 11, 12, 19, 20, 25, 27-42, 44, 45, 47-49, 51, 53-55, 57-59, 61, 62, 65, 67, 68-86, 90, 91, 93, 95-105, 108, 110, 112, 114-120, 122, 125-128, 132, 135-137, 140, 141, 143-148, 150-152, 154-160, 162-166, 168-176, 178-183, 185-195, 198, 200-204, 206-210, 212-222 |
| TEM-E104K | TEM-3, 4, 6, 8, 9, 15-18, 21, 22, 24, 26, 43, 46, 50, 52, 56, 60, 63, 66, 87-89, 92, 94, 106, 107, 109, 111, 113, 121, 123, 124, 129-131, 133, 134, 138, 139, 142, 149, 153, 161, 167, 177, 184, 197, 199, 205, 211, |
| TEM-R164 | TEM-1-4, 13, 15, 18-22, 25, 30-42, 44, 45, 47-52, 54-59, 62, 65-74, 76-84, 88-90, 92-101, 103-106, 108, 110-113, 116, 117, 119, 120, 122-124, 126-128, 135, 138-140, 145, 146, 148, 150, 153, 156, 157, 159, 160, 162-164, 166-176, 178-183, 185, 186, 188-192, 194, 196-204, 206-222 |
| TEM-R164H | TEM-6, 11, 16, 27-29, 43, 61, 75, 107, 109, 115, 118, 132, 134, 147, 151, 152, 161, 187 |
| TEM-R164C | TEM-87, 92, 143, 144, 193, 195 |
| TEM-R164S | TEM-5, 7-10, 12, 24, 26, 46, 53, 60, 63, 85, 86, 102, 114, 121, 125, 129-131, 133, 136, 137, 149, 154, 155, 158, 165, 177, 184, 205 |
| TEM-G238/ E240 | TEM-1, 2, 6, 7, 9, 11-13, 16-18, 26, 29-41, 43-45, 51, 53-60, 62-65, 67, 69, 70, 73-84, 87, 90, 95-100, 102-106, 108-110, 115-119, 122, 124-131, 133, 140, 141, 143, 145-148, 150, 151, 153, 154, 156-166, 168-176, 179-187, 190, 192-196, 198, 200-206, 208-210, 212-222 |
| TEM-G238S/ E240 | TEM-3, 4, 8, 15, 19-22, 25, 50, 52, 66, 88, 89, 92, 94, 107, 112, 113, 120, 123, 134, 138, 139, 167, 197, 199, 211 |
| TEM-G238/ E240K | TEM-5, 10, 24, 27, 28, 46, 61, 85, 86, 91, 114, 121, 132, 136, 144, 152, 155, 177, 189, 191 |
| TEM-G238S/ E240K | TEM-42, 47-49, 68, 71, 72, 93, 101, 188 |

The method involves extraction of bacterial DNA from a biological sample from a patient or directly from a biological sample culture or culture isolate. Extraction can be accomplished by any known method in the art. Preferably, the extraction method both isolates and purifies the DNA. By "purifies" it is meant that DNA sample is substantially free of protein, cellular debris and PCR inhibitors. Methods of extraction suitable for use in the present invention include, for example but not limited to Roche MagNAPure.

Unlike previous methods, the methods of the invention provide ultra-high sensitivity and resolution of MDRO-associated genes, with format flexibility to discriminate individual gene subtypes, or to screen for all MDRO gene families and subtypes in a combined probe "cocktail" assay format. The method provides for an optimal assay system whereby new MDRO genes or subtypes or infectious disease organism molecular biomarkers or identification genes can be incorporated into the assay format, to expand the scope of MDRO screening and identification potential based on the emergence of new MDROs over time. This ultra-high sensitivity and resolution may be accomplished with or without combining a pre-amplification step followed by a detection step utilizing primers and probes based upon sequence homology of the MRDO-associated gene families. These primers and probes include degenerate primers sequence capable of amplifying and detecting MDRO associated gene sub-families and subtypes, and based on the level of detection, can provide a semi-quantitative assessment on the level of MDRO genes in the sample. Thus, the methods of the invention are not only capable of detecting the presence of a MRDO-associated gene in a sample, the method also provides for the identification and semi-quantitative level of the subtype of the MDRO-associated gene. This ability to provide a genotype allows for the presumptive identification of bacterial or other infectious disease species. Thus, an unexpected advantage of the methods of the invention is that it provides the clinician with some guidance as to which bacteria species the subject is infected/or colonized with, and provides guidance on the risk profile of the subject for potential conversion from colonization to infection, or potential risk of transmitting a MDRO to another individual. (See, FIG. 1). It is also possible to include probes in the test format for organism identification (ID) and viruses along with Resistome Test probes to provide additional information about the patient microbiome. It is also possible to perform sequence-based microbiome analysis along with the Resistome Test.

The Resistome Test can be used by a clinician to help determine which antibiotics should be used based on a Resistome test result of the patient sample, either because of an individual resistance gene or combination of genes. Overall, the ability to stratify genotype is also very specific and reproducible (See, FIGS. 3 and 4). Organism Resistome profiles can be matched with actual Antibiotic Susceptibility Test (AST) data. When patients with matching Resistome patterns are found, their antibiotic resistance can potentially be inferred from this information.

Another unexpected advantage of the methods of the invention is the extreme sensitivity that can be ascertained from different sample types, including using a single swab sample, mixed culture sample, or bacterial isolate. Unlike other methods known in the art, the methods of the invention are capable of detecting less than 210 CFU/sample (and in some instance less than 15 CFU/sample) without the need to culture the sample. (See, FIG. 2).

The patient is suspected of or at high risk for having a multi-drug resistant bacteria colonization or infection. High risk patients include but are not limited to, patients residing in or being admitted from a long-term care facility, patients admitted to Intensive Care Units (ICUs), immuno-compromised patients, patients being treated for cancer or undergoing chemotherapy, organ and bone marrow transplant patients, patients with ventilators or catheters, patients in preparation for surgical procedures, postsurgical patients, patients previously diagnosed or treated for a Healthcare-Associated Infection (HAI), and others. For example, a high risk patient is neutropenic, has cancer or has received a transplant. In some aspects the patient is "asymptomatic" means not exhibiting the traditional signs and symptoms.

The sample is any biological sample that contains gram-negative or gram-positive bacteria. For example, the biological sample is an anal swab, a rectal swab, a skin swab, nasal swab, wound swab, stool, blood, plasma, serum, urine, sputum, respiratory lavage, cerebrospinal fluid, or culture isolate.

Once the bacterial DNA is extracted from the biological sample, an enrichment step is performed prior to the detection of the MDRO associated genes. Enrichment is accomplished for example by performing multiplex PCR. After enrichment, detection is performed for example by using real time PCR using primers that are specific to the MDRO associated gene being detected. Optionally, an internal amplification control is included to guard against false negatives associated with PCR inhibition. Additionally, appropriate positive, negative and no-template control (NTC) samples are included during each performance run of the assay.

Definitions

In accordance with long standing patent law convention, the words "a" and "an" when used in this application, including the claims, denotes "one or more."

As used herein, the terms "about" and "approximately" are interchangeable, and should generally be understood to refer to a range of numbers around a given number, as well as to all numbers in a recited range of numbers (e.g., "about 5 to 15" means "about 5 to about 15" unless otherwise stated). Moreover, all numerical ranges herein should be understood to include each whole integer within the range.

The terms "e.g.," and "i.e." as used herein, is used merely by way of example, without limitation intended, and should not be construed as referring only those items explicitly enumerated in the specification.

As used herein, infection is meant to include any infectious agent of bacterial origin. The bacterial infection may be the result of gram-positive, gram-negative bacteria or atypical bacteria.

The term "Gram-positive bacteria" are bacteria that are stained dark blue by Gram staining. Gram-positive organisms are able to retain the crystal violet stain because of the high amount of peptidoglycan in the cell wall.

The term "Gram-negative bacteria" are bacteria that do not retain the crystal violet dye in the Gram staining protocol.

The term "Multi-drug Resistant Organism" is a microrganisms (bacteria, viruses, fungi or parasites) that is resistant to distinct antimicrobial agents, first and foremost antibiotics, but also antifungal drugs, antiviral medications, and antiparasitic drugs.

The term "CRE" refers to carbapenem-resistant enterobacteriaceae.

The term "ESBL" refers to extended spectrum beta lactamase.

The term "AmpC" refers to cephalosporinases encoded on the chromosomes of many of the Enterobacteriaceae and a few other organisms, where they mediate resistance to cephalothin, cefazolin, cefoxitin, most penicillins, and beta-lactamase inhibitor-beta-lactam combinations. A multi-drug resistant organism includes, but are not limited to, organisms belonging to the genus *Acinetobacter, Citrobacter, Enterobacter, Enteroccus, Escherichia, Kiebsiella, Serratia* or *Staphyloccus*. Exemplary multi-drug resistant organisms include *Acinetobacter Baumannii* such as ATCC isolate #2894233-696-101-1, ATCC isolate #2894257-696-101-1 ATCC isolate #2894255-696-101-1, ATCC isolate #2894253-696-101-1, or ATCC #2894254-696-101-1; *Citrobacter freundii* such as ATCC isolate #33128, ATCC isolate #2894218-696-101-1, ATCC isolate #2894219-696-101-1, ATCC isolate #2894224-696-101-1, ATCC isolate #2894218-632-101-1, or ATCC isolate #2894218-659-101-1; *Enterobacter cloacae* such as ATCC isolate #22894251-659-101-1, ATCC isolate #22894264-659-101-1, ATCC isolate #22894246-659-101-1, ATCC isolate #22894243-659-101-1, or ATCC isolate #22894245-659-101-1; *Enteroccus facalis* such as ATCC isolate #22894228-659-101-1 ATCC isolate #22894222-659-101-1, ATCC isolate #22894221-659-101-1, ATCC isolate #22894225-659-101-1, or ATCC isolate #22894245-659-101-1; *Enteroccus faecium* such as ATCC isolate #51858, ATCC isolate #35667, ATCC isolate #2954833_2694008 ATCC isolate #2954833_2692765, or ATCC isolate #2954836_2694361; *Escherichia coli* such as ATCC isolate CGUC 11332, CGUC 11350, CGUC 11371, CGUC 11378, or CGUC 11393; *Kiebsiella pneumonia* such as ATTC isolate #27736, ATTC isolate #29011, ATTC isolate #20013, ATTC isolate #33495, or ATTC isolate #35657; *Serratia marcescens* such as ATCC isolate #43862, ATCC isolate #2338870, ATCC isolate #2426026, ATCC isolate # SIID 2895511, or ATCC isolate # SIID 2895538; or *Staphyloccus aureus* such as ATCC isolate # JHH 02, ATCC isolate # JHH 02, ATCC isolate # JHH 03, ATCC isolate # JHH 04, ATCC isolate # JHH 05, or ATCC isolate # JHH 06.

The term "methods of treating" includes methods of managing, and when used in connection with the biological organism or infection, includes the amelioration, elimination, reduction, prevention, or other relief or management from the detrimental effects of a biological organism. In a preferred embodiment, these detrimental effects include a mycobacterial infection, symptoms characterizing and/or effects associated with tuberculosis in the subject, or a combination thereof.

As used herein, the term "nucleic acid" includes one or more types of: polydeoxyribonucleotides (containing 2-deoxy-D-ribose), polyribonucleotides (containing D-ribose), and any other type of polynucleotide that is an N-glycoside of a purine or pyrimidine base, or modified purine or pyrimidine bases (including abasic sites). The term "nucleic acid," as used herein, also includes polymers of ribonucleosides or deoxyribonucleosides that are covalently bonded, typically by phosphodiester linkages between subunits, but in some cases by phosphorothioates, methylphosphonates, and the like. "Nucleic acids" include single- and double-stranded DNA, as well as single- and double-stranded RNA. Exemplary nucleic acids include, without limitation, gDNA;

hnRNA; mRNA; rRNA, tRNA, micro RNA (miRNA), small interfering RNA (siRNA), small nucleolar RNA (snORNA), small nuclear RNA (snRNA), and small temporal RNA (stRNA), and the like, and any combination thereof.

As used herein, the term "DNA segment" refers to a DNA molecule that has been isolated free of total genomic DNA of a particular species. Therefore, a DNA segment obtained from a biological sample using one of the compositions disclosed herein refers to one or more DNA segments that have been isolated away from, or purified free from, total genomic DNA of the particular species from which they are obtained, and also in the case of pathogens, optionally isolated away from, or purified free from total mammalian (preferably human) genomic DNA of the infected individual. Included within the term "DNA segment," are DNA segments and smaller fragments of such segments, as well as recombinant vectors, including, for example, plasmids, cosmids, phage, viruses, and the like.

Similarly, the term "RNA segment" refers to an RNA molecule that has been isolated free of total cellular RNA of a particular species. Therefore, RNA segments obtained from a biological sample using one of the compositions disclosed herein, refers to one or more RNA segments (either of native or synthetic origin) that have been isolated away from, or purified free from, other RNAs. Included within the term "RNA segment," are RNA segments and smaller fragments of such segments.

The terms "identical" or percent "identity," in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the sequence comparison algorithms described below (or other algorithms available to persons of ordinary skill) or by visual inspection.

The phrase "substantially identical," in the context of two nucleic acids refers to two or more sequences or subsequences that have at least about 90%, preferably 91%, most preferably about 92%, 93%, 94%, 95%, 96%, 97%, 98%, 98.5%, 99%, 99.1%, 99.2%, 99.3%, 99.4%, 99.5%, 99.6%, 99.7%, 99.8%, 99.9% or more nucleotide residue identity, when compared and aligned for maximum correspondence, as measured using a sequence comparison algorithm or by visual inspection. Such "substantially identical" sequences are typically considered "homologous," without reference to actual ancestry.

As used herein, "sample" includes anything containing or presumed to contain a substance of interest. It thus may be a composition of matter containing nucleic acid, protein, or another biomolecule of interest. The term "sample" can thus encompass a solution, cell, tissue, or population of one of more of the same that includes a population of nucleic acids (genomic DNA, cDNA, RNA, protein, other cellular molecules, etc.). The terms "nucleic acid source," "sample," and "specimen" are used interchangeably herein in a broad sense, and are intended to encompass a variety of biological sources that contain nucleic acids, protein, one or more other biomolecules of interest, or any combination thereof. Exemplary biological samples include, but are not limited to, whole blood, plasma, serum, sputum, urine, stool, white blood cells, red blood cells, buffy coat, swabs (including, without limitation, buccal swabs, throat swabs, vaginal swabs, urethral swabs, cervical swabs, rectal swabs, lesion swabs, abscess swabs, nasopharyngeal swabs, and the like), urine, stool, sputum, tears, mucus, saliva, semen, vaginal fluids, lymphatic fluid, amniotic fluid, spinal or cerebrospinal fluid, peritoneal effusions, pleural effusions, exudates, punctates, epithelial smears, biopsies, bone marrow samples, fluids from cysts or abscesses, synovial fluid, vitreous or aqueous humor, eye washes or aspirates, bronchial or pulmonary lavage, lung aspirates, and organs and tissues, including but not limited to, liver, spleen, kidney, lung, intestine, brain, heart, muscle, pancreas, and the like, and any combination thereof. Tissue culture cells, including explanted material, primary cells, secondary cell lines, and the like, as well as lysates, homogenates, extracts, or materials obtained from any cells, are also within the meaning of the term "biological sample," as used herein. The ordinary-skilled artisan will also appreciate that lysates, extracts, or materials obtained from any of the above exemplary biological samples are also within the scope of the invention.

As used herein, the term "buffer" includes one or more compositions, or aqueous solutions thereof, that resist fluctuation in the pH when an acid or an alkali is added to the solution or composition that includes the buffer. This resistance to pH change is due to the buffering properties of such solutions, and may be a function of one or more specific compounds included in the composition. Thus, solutions or other compositions exhibiting buffering activity are referred to as buffers or buffer solutions. Buffers generally do not have an unlimited ability to maintain the pH of a solution or composition; rather, they are typically able to maintain the pH within certain ranges, for example from a pH of about 5 to 7.

As used herein, the term "patient" (also interchangeably referred to as "host" or "subject") refers to any host that can serve as a source of one or more of the biological samples or specimens as discussed herein. In certain aspects, the donor will be a vertebrate animal, which is intended to denote any animal species (and preferably, a mammalian species such as a human being). In certain embodiments, a "patient" refers to any animal host, including but not limited to, human and non-human primates, avians, reptiles, amphibians, bovines, canines, caprines, cavities, corvines, epines, equines, felines, hircines, lapines, leporines, lupines, ovines, porcines, racines, vulpines, and the like, including, without limitation, domesticated livestock, herding or migratory animals or birds, exotics or zoological specimens, as well as companion animals, pets, and any animal under the care of a veterinary practitioner.

The term "substantially free" or "essentially free," as used herein, typically means that a composition contains less than about 10 weight percent, preferably less than about 5 weight percent, and more preferably less than about 1 weight percent of a compound. In a preferred embodiment, these terms refer to less than about 0.5 weight percent, more preferably less than about 0.1 weight percent or even less than about 0.01 weight percent. The terms encompass a composition being entirely free of a compound or other stated property, as well. With respect to degradation or deterioration, the term "substantial" may also refer to the above-noted weight percentages, such that preventing substantial degradation would refer to less than about 15 weight percent, less than about 10 weight percent, preferably less than about 5 weight percent, etc., being lost to degradation. In other embodiments, these terms refer to mere percentages rather than weight percentages, such as with respect to the term "substantially non-pathogenic" where the term "substantially" refers to leaving less than about 10 percent, less than about 5 percent, etc., of the pathogenic activity.

As used herein, the term "heterologous" is defined in relation to a predetermined referenced nucleic acid sequence. For example, with respect to a structural gene sequence, a heterologous promoter is defined as a promoter that does not naturally occur adjacent to the referenced structural gene, but which is positioned by the hand of man in one or more laboratory manipulations that are routinely employed by those of ordinary skill in the molecular biological arts. Likewise, a heterologous gene or nucleic acid segment is defined as a gene or nucleic acid segment that does not naturally occur adjacent to the referenced sequence, promoter and/or enhancer element(s), etc.

As used herein, the term "healthy" refers to an individual whom is not at high risk of being infected with a multi-drug resistant organism.

As used herein, the term "homology" refers to a degree of complementarity between two or more polynucleotide or polypeptide sequences. The word "identity" may substitute for the word "homology" when a first nucleic acid or amino acid sequence has the exact same primary sequence as a second nucleic acid or amino acid sequence. Sequence homology and sequence identity can be determined by analyzing two or more sequences using algorithms and computer programs known in the art. Such methods may be used to assess whether a given sequence is identical or homologous to another selected sequence.

As used herein, "homologous" means, when referring to polynucleotides, sequences that have the same essential nucleotide sequence, despite arising from different origins. Typically, homologous nucleic acid sequences are derived from closely related genes or organisms possessing one or more substantially similar genomic sequences. By contrast, an "analogous" polynucleotide is one that shares the same function with a polynucleotide from a different species or organism, but may have a significantly different primary nucleotide sequence that encodes one or more proteins or polypeptides that accomplish similar functions or possess similar biological activity. Analogous polynucleotides may often be derived from two or more organisms that are not closely related (e.g., either genetically or phylogenetically).

The terms "identical" or percent "identity", in the context of two or more nucleic acid or polynucleotide sequences, refer to two or more sequences or subsequences that are the same or have a specified percentage of nucleotides that are the same, when compared and aligned for maximum correspondence over a comparison window, as measured using a sequence comparison algorithm or by manual alignment and visual inspection.

A "primer" or "primer sequence" may include any nucleic acid sequence or segment that selectively hybridizes to a complementary template nucleic acid strand ("target sequence") and functions as an initiation point for the addition of nucleotides to replicate the template strand. Primer sequences of the present invention may be labeled or contain other modifications which allow the detection and/or analysis of amplification products. In addition to serving as initiators for polymerase-mediated duplication of target DNA sequences, primer sequences may also be used for the reverse transcription of template RNAs into corresponding DNAs.

A "target sequence" or "target nucleotide sequence" as used herein includes any nucleotide sequence to which one of the disclosed primer sequences hybridizes under conditions that allow an enzyme having polymerase activity to elongate the primer sequence, and thereby replicate the complementary strand.

As used herein, the term "polypeptide" is intended to encompass a singular "polypeptide" as well as plural "polypeptides," and includes any chain or chains of two or more amino acids. Thus, as used herein, terms including, but not limited to "peptide," "dipeptide," "tripeptide," "protein," "enzyme," "amino acid chain," and "contiguous amino acid sequence" are all encompassed within the definition of a "polypeptide," and the term "polypeptide" can be used instead of, or interchangeably with, any of these terms. The term further includes polypeptides that have undergone one or more post-translational modification(s), including for example, but not limited to, glycosylation, acetylation, phosphorylation, amidation, derivatization, proteolytic cleavage, post-translation processing, or modification by inclusion of one or more non-naturally occurring amino acids. Conventional nomenclature exists in the art for polynucleotide and polypeptide structures. For example, one-letter and three-letter abbreviations are widely employed to describe amino acids: Alanine (A; Ala), Arginine (R; Arg), Asparagine (N; Asn), Aspartic Acid (D; Asp), Cysteine (C; Cys), Glutamine (Q; Gln), Glutamic Acid (E; Glu), Glycine (G; Gly), Histidine (H; His), Isoleucine (I; Ile), Leucine (L; Leu), Methionine (M; Met), Phenylalanine (F; Phe), Proline (P; Pro), Serine (S; Ser), Threonine (T; Thr), Tryptophan (W; Trp), Tyrosine (Y; Tyr), Valine (V; Val), and Lysine (K; Lys). Amino acid residues described herein are preferred to be in the "L" isomeric form. However, residues in the "D" isomeric form may be substituted for any L-amino acid residue provided the desired properties of the polypeptide are retained.

"Protein" is used herein interchangeably with "peptide" and "polypeptide," and includes both peptides and polypeptides produced synthetically, recombinantly, or in vitro and peptides and polypeptides expressed in vivo after nucleic acid sequences are administered into a host animal or human subject. The term "polypeptide" is preferably intended to refer to all amino acid chain lengths, including those of short peptides of about 2 to about 20 amino acid residues in length, oligopeptides of about 10 to about 100 amino acid residues in length, and polypeptides of about 100 to about 5,000 or more amino acid residues in length. The term "sequence," when referring to amino acids, relates to all or a portion of the linear N-terminal to C-terminal order of amino acids within a given amino acid chain, e.g., polypeptide or protein; "subsequence" means any consecutive stretch of amino acids within a sequence, e.g., at least 3 consecutive amino acids within a given protein or polypeptide sequence. With reference to nucleotide and polynucleotide chains, "sequence" and "subsequence" have similar meanings relating to the 5' to 3' order of nucleotides.

As used herein, the term "substantially homologous" encompasses two or more biomolecular sequences that are significantly similar to each other at the primary nucleotide sequence level. For example, in the context of two or more nucleic acid sequences, "substantially homologous" can refer to at least about 75%, preferably at least about 80%, and more preferably at least about 85%, or at least about 90% identity, and even more preferably at least about 95%, more preferably at least about 97% identical, more preferably at least about 98% identical, more preferably at least about 99% identical, and even more preferably still, entirely identical (i.e., 100% or "invariant").

Likewise, as used herein, the term "substantially identical" encompasses two or more biomolecular sequences (and in particular polynucleotide sequences) that exhibit a high degree of identity to each other at the nucleotide level. For example, in the context of two or more nucleic acid sequences, "substantially identical" can refer to sequences that at least about 80%, and more preferably at least about 85% or at least about 90% identical to each other, and even more preferably at least about 95%, more preferably at least about 97% identical, more preferably at least about 98% identical, more preferably at least about 99% identical, and even more preferably still, entirely identical (i.e., 100% identical or "non-degenerate").

The term "recombinant" indicates that the material (e.g., a polynucleotide or a polypeptide) has been artificially or synthetically (non-naturally) altered by human intervention. The alteration can be performed on the material within or removed from, its natural environment or state. Specifically, e.g., a promoter sequence is "recombinant" when it is produced by the expression of a nucleic acid segment engineered by the hand of man. For example, a "recombinant nucleic acid" is one that is made by recombining nucleic acids, e.g., during cloning, DNA shuffling or other procedures, or by chemical or other mutagenesis; a "recombinant polypeptide" or "recombinant protein" is a polypeptide or protein which is produced by expression of a recombinant nucleic acid; and a "recombinant virus," e.g., a recombinant influenza virus, is produced by the expression of a recombinant nucleic acid.

As used herein, the term "operably linked" refers to a linkage of two or more polynucleotides or two or more nucleic acid sequences in a functional relationship. A nucleic acid is "operably linked" when it is placed into a functional relationship with another nucleic acid sequence. For instance, a promoter or enhancer is operably linked to a coding sequence if it affects the transcription of the coding sequence. "Operably linked" means that the nucleic acid sequences being linked are typically contiguous, or substantially contiguous, and, where necessary to join two protein coding regions, contiguous and in reading frame. Since enhancers generally function when separated from the promoter by several kilobases and intronic sequences may be of variable lengths; however, some polynucleotide elements may be operably linked but not contiguous.

The phrases "isolated" or "biologically pure" refer to material that is substantially, or essentially, free from components that normally accompany the material as it is found in its native state. Thus, isolated polynucleotides in accordance with the invention preferably do not contain materials normally associated with those polynucleotides in their natural, or in situ, environment.

"Link" or "join" refers to any method known in the art for functionally connecting one or more proteins, peptides, nucleic acids, or polynucleotides, including, without limitation, recombinant fusion, covalent bonding, disulfide bonding, ionic bonding, hydrogen bonding, electrostatic bonding, and the like.

As used herein, the term "plasmid" refers to a genetic construct that is composed of genetic material (i.e., nucleic acids). Typically, a plasmid contains an origin of replication that is functional in bacterial host cells, e.g., *Escherichia coli*, and selectable markers for detecting bacterial host cells including the plasmid. Plasmids of the present invention may include one or more genetic elements as described herein arranged such that an inserted coding sequence can be transcribed and translated in a suitable expression cells. In addition, the plasmid may include one or more nucleic acid segments, genes, promoters, enhancers, activators, multiple cloning regions, or any combination thereof, including segments that are obtained from or derived from one or more natural and/or artificial sources.

Suitable standard hybridization conditions for the present invention include, for example, hybridization in 50% formamide, 5.times.Denhardts' solution, 5.times.SSC, 25 mM sodium phosphate, 0.1% SDS and 100.mu.g/mL of denatured salmon sperm DNA at 42 degrees C. for 16 h followed by 1 hr sequential washes with 0.1.times.SSC, 0.1% SDS solution at 60.degree. C. to remove the desired amount of background signal. Lower stringency hybridization conditions for the present invention include, for example, hybridization in 35% formamide, 5.times.Denhardts' solution, 5.times.SSC, 25 mM sodium phosphate, 0.1% SDS and 100.mu.g/mL denatured salmon sperm DNA or *E. coli* DNA at 42 degrees C. for 16 h followed by sequential washes with 0.8.times.SSC, 0.1% SDS at 55.degree. C. Those of skill in the art will recognize that conditions can be readily adjusted to obtain the desired level of stringency.

Naturally, the present invention also encompasses nucleic acid segments that are complementary, essentially complementary, and/or substantially complementary to at least one or more of the specific nucleotide sequences specifically set forth herein. Nucleic acid sequences that are "complementary" are those that are capable of base-pairing according to the standard Watson-Crick complementarity rules. As used herein, the term "complementary sequences" means nucleic acid sequences that are substantially complementary, as may be assessed by the same nucleotide comparison set forth above, or as defined as being capable of hybridizing to one or more of the specific nucleic acid segments disclosed herein under relatively stringent conditions such as those described immediately above.

As described above, the probes and primers of the present invention may be of any length. By assigning numeric values to a sequence, for example, the first residue is 1, the second residue is 2, etc., an algorithm defining all probes or primers contained within a given sequence can be proposed: n to n+y where n is an integer from 1 to the last number of the sequence and y is the length of the probe or primer minus one, where n+y does not exceed the last number of the sequence. Thus, for a 25-basepair probe or primer (i.e., a "25-mer"), the collection of probes or primers correspond to bases 1 to 25, bases 2 to 26, bases 3 to 27, bases 4 to 28, and so on over the entire length of the sequence. Similarly, for a 35-basepair probe or primer (i.e., a "35-mer), exemplary primer or probe sequence include, without limitation, sequences corresponding to bases 1 to 35, bases 2 to 36, bases 3 to 37, bases 4 to 38, and so on over the entire length of the sequence. Likewise, for 40-mers, such probes or primers may correspond to the nucleotides from the first basepair to by 40, from the second by of the sequence to by 41, from the third by to by 42, and so forth, while for 50-mers, such probes or primers may correspond to a nucleotide sequence extending from bp 1 to bp 50, from bp 2 to bp 51, from bp 3 to bp 52, from bp 4 to bp 53, and so forth.

In certain embodiments, it will be advantageous to employ one or more nucleic acid segments of the present invention in combination with an appropriate detectable marker (i.e., a "label,"), such as in the case of employing labeled polynucleotide probes in determining the presence of a given target sequence in a hybridization assay. A wide variety of appropriate indicator compounds and compositions are known in the art for labeling oligonucleotide probes, including, without limitation, fluorescent, radioactive, enzymatic or other ligands, such as avidin/biotin, etc., which are capable of being detected in a suitable assay. In particular embodiments, one may also employ one or more fluorescent labels or an enzyme tag such as urease, alkaline phosphatase or peroxidase, instead of radioactive or other environmentally less-desirable reagents. In the case of enzyme tags, colorimetric, chromogenic, or fluorigenic indicator substrates are known that can be employed to provide a method for detecting the sample that is visible to the human eye, or by analytical methods such as scintigraphy, fluorimetry, spectrophotometry, and the like, to identify specific hybridization with samples containing one or more complementary or substantially complementary nucleic acid sequences. In the case of so-called "multiplexing" assays, where two or more labeled probes are detected either simultaneously or sequentially, it may be desirable to label a first oligonucleotide probe with a first label having a first detection property or parameter (for example, an emission and/or excitation spectral maximum), which also labeled a second oligonucleotide probe with a second label having a second detection property or parameter that is different (i.e., discreet or discernable from the first label. The use of multiplexing assays, particularly in the context of genetic amplification/detection protocols are well-known to those of ordinary skill in the molecular genetic arts.

In general, it is envisioned that one or more of the amplification primers and/or hybridization probes described herein will be useful both as reagents in solution hybridization (e.g., PCR methodologies and the like), and in embodiments employing "solid-phase" analytical protocols and such like.

Methods and Uses of the Invention

The methods disclosed herein are used to identify subjects that are colonized or infected with a multi-drug resistant organism. More specifically, some methods of the invention are used to distinguish patients having a multi-drug resistant organism from patients with a non-infectious disease and/or healthy individuals. For example, the methods of the invention can be used to make a contact precaution recommendation for the patient having a multi-drug resistant bacterial colonization or infection. Contact precaution recommendations includes one or more of the following: isolating the patient to a quarantine area or ward, providing a private room for said patient, donning personal protective apparel upon entering the patient's room, limiting patient mobility, limiting or restricting access of non-colonized or non-infected patients or medical personnel to the patient, or providing dedicated patient care equipment.

Some methods of the present invention can also be used to monitor or select a treatment regimen for a patient who has an MDRO colonization or infection, and to screen subjects who have not been previously diagnosed as having an MDRO colonization or infection, such as subjects who exhibit risk factors for developing an infection. Some methods of the present invention are used to identify and/or diagnose subjects who are asymptomatic for a MDRO infection. "Asymptomatic" means not exhibiting the traditional signs and symptoms.

A reference value can be relative to a number or value derived from population studies, including without limitation, such subjects having the same infection, subject having the same or similar age range, subjects in the same or similar ethnic group, or relative to the starting sample of a subject undergoing treatment for an infection. Such reference values can be derived from statistical analyses and/or risk prediction data of populations obtained from mathematical algorithms and computed indices of infection. Reference indices can also be constructed and used using algorithms and other methods of statistical and structural classification.

The effectiveness of a treatment regimen can be monitored by detecting a one or more MDRO-associated genes in a sample obtained from a subject over time and comparing the amount of MDRO-associated genes detected. For example, a first sample can be obtained prior to the subject receiving treatment and one or more subsequent samples are taken after or during treatment of the subject.

For example, the methods of the invention can be used to discriminate between patients that are colonized or infected with an MDRO and those that are not. This will allow patients to be stratified and treated accordingly.

In a specific embodiment of the invention a treatment recommendation (i.e., selecting a treatment regimen) for a subject is provided by identifying a MDRO colonization or infection in the subject according to the method of any of the disclosed methods and recommending that the subject receive an antibiotic treatment. For example, when KPC, NDM, OXA, VIM, SFC, IMP, SME, IMI, NMC, or CcrA is detected recommending that the patient does not receive a carbapenem antibiotic; when CTM-X, PER, VEB, GES, BES, SFO, TLA, TEM with amino acid substitutions E104K, R164H, R164S, R164C, G238S or E240K, or SHV with amino acid substitutions G156D, G238S or E240K is detected recommending that the patient does not receive a cephalosporin antibiotic, when ACC, MOX, CMY, CFE, ACT, DHA or FOX is detected recommending that the patient does not receive a beta-lactamase inhibitor-beta-lactam combination; or when VanA is detected recommending that the patient does not receive vancomycin.

In other embodiments, the presence or absence of the MDRO-associated genes and are used in conjunction with other clinical factors that to make an antibiotic recommendation for a patient. For example KPC, NDM, OXA, VIM, IMP, SME, SFC, IMI, NMC, or CcrA is detected consider that the patient may be resistant to carbapenem antibiotics; when CTM-X, PER, VEB, GES, BES, SFO, TLA, TEM with amino acid substitutions E104K, R164H, R164S, R164C, G238S or E240K, or SHV with amino acid substitutions G156D, G238S or E240K is detected consider that the patient may be resistant to cephalosporin antibiotics, when ACC, MOX, CMY, CFE, ACT, DHA or FOX is detected consider that the patient may be resistant to a beta-lactamase inhibitor-beta-lactam combination; or when VanA is consider that the patient may be resistant to vancomycin.

In another embodiment, the methods of the invention can be used to prompt additional targeted diagnosis such as pathogen specific PCRs, chest-X-ray, cultures etc. For example, the methods of the invention can be used to recommend a test to determine the genus and or species of the multi-drug resistant organism to determine the source of the bacterial infection. In another embodiment, the methods of the invention can be used as a screening and surveillance method to establish the source and type of infection or colonization in a patient or person athlete (anatomical site) and/or from the environment such as hospital room location or fixture, or sports facility locker room location, in order to characterize infection transmission events and to generate geophysical maps of infection outbreaks in healthcare settings, sports complexes, and other physical settings where MDROs may colonize or spread (see FIGS. 7, 8, 9, and 10).

Some aspects of the present invention can also be used to screen patient or subject populations in any number of settings. For example, a health maintenance organization, public health entity or school health program can screen a group of subjects to identify those requiring interventions, as described above, or for the collection of epidemiological data. Insurance companies (e.g., health, life or disability) may screen applicants in the process of determining coverage or pricing, or existing clients for possible intervention. Data collected in such population screens, particularly when tied to any clinical progression to conditions like infection, will be of value in the operations of, for example, health maintenance organizations, public health programs and insurance companies. Such data arrays or collections can be stored in machine-readable media and used in any number of health-related data management systems to provide improved healthcare services, cost effective healthcare, improved insurance operation, etc. See, for example, U.S. Patent Application No. 2002/0038227; U.S. Patent Application No. US 2004/0122296; U.S. Patent Application No. US 2004/0122297; and U.S. Pat. No. 5,018,067. Such systems can access the data directly from internal data storage or remotely from one or more data storage sites as further detailed herein.

A machine-readable storage medium can comprise a data storage material encoded with machine readable data or data arrays which, when using a machine programmed with instructions for using said data, is capable of use for a variety of purposes. Measurements of effective amounts of the biomarkers of the invention and/or the resulting evaluation of risk from those biomarkers can be implemented in computer programs executing on programmable computers, comprising, inter alia, a processor, a data storage system (including volatile and non-volatile memory and/or storage elements), at least one input device, and at least one output device. Program code can be applied to input data to perform the functions described above and generate output information. The output information can be applied to one or more output devices, according to methods known in the art. The computer may be, for example, a personal computer, microcomputer, or workstation of conventional design.

Each program can be implemented in a high level procedural or object oriented programming language to communicate with a computer system. However, the programs can be implemented in assembly or machine language, if desired. The language can be a compiled or interpreted language. Each such computer program can be stored on a storage media or device (e.g., ROM or magnetic diskette or others as defined elsewhere in this disclosure) readable by a general or special purpose programmable computer, for configuring and operating the computer when the storage media or device is read by the computer to perform the procedures described herein. The health-related data management system used in some aspects of the invention may also be considered to be implemented as a computer-readable storage medium, configured with a computer program, where the storage medium so configured causes a computer to operate in a specific and predefined manner to perform various functions described herein.

Methods of Detecting MDRO-Associated Genes

Following collection of the population of polynucleotides from a biological sample, any method of nucleic acid extraction or separation from the collection solution and microorganism debris, such as proteins, lipids and carbohydrates, may be performed, as would be known to one of ordinary skill in the art, including, but not limited to, the use of the standard phenol/chloroform purification, silica-based methods, and extraction methods based on magnetic glass particle.

Compositions and methods used in the present invention are compatible with most, if not all, commercially available nucleic acid extraction compositions and methods, such as, but not limited to QiaAmp® DNA Mini kit (Qiagen®, Hilden, Germany), MagNA Pure 96 System (Roche Diagnostics, USA), and the NucliSENS® easyMAG® extraction system (bioMerieux, France).

After sample extraction, a sample enrichment step (pre-amplification) is performed. The pre-amplification step can be accomplished by any methods know in the art, for example by PCR. Preferable the sample enrichment step is performed using nested PCR which allows for simultaneous amplification of several target genes using multiplex PCR.

After amplification, MDRO-associated gene are detected by any method known in the art, and preferably by multiplex real time PCR formats such as nanofluidic, microfluidic chip detection real time PCR instrumentation such as Fluidigm Biomark; bead based multiplex detection systems such as Luminex; single target or low multiplex PCR format instrumentation such as Roche Light Cycler; droplet PCR/digital PCR detection system such as Raindances's RainDrop System; or next generation sequencing technology such as Illumina MiSeq, or semiconductor sequencing such as Ion Torrent's, ion PGM™ System.

The present invention also provides for compositions and methods of detecting MDRO associated gene-specific nucleic acid sequences present in a population of polynucleotides that has been isolated or extracted from a biological sample. The polynucleotide compositions of the present invention, and particularly those useful in the detection of MDRO associated gene-specific nucleic acid sequences (including, for example, any one of or a combination of KPC, NDM, VIM, IMP, OXA, CTX-M or Van-A specific nucleic acids), preferably contain at least a single primer, or alternatively, two or more primers (e.g., "forward" and "reverse" primers) that may be used to facilitate amplification of the particular target nucleic acid sequence to be amplified. Exemplary primers useful in the practice of the invention include, but are in no way limited to, those primer sequences that specifically bind to the target nucleic acid sequence itself or to one or more regions immediately upstream (5') and or downstream (3') of the actual target nucleic sequence.

Primers useful in amplification of a particular sequence of interest may be designed using, for example, a computer program such as OLIGO® (Molecular Biology Insights Inc., Cascade, Colo., USA). Typically, oligonucleotide primers are from about 10 to about 60 or so nucleotides in length (including, without limitation, all intermediate integers, e.g., 10, 11, 12, etc., or even 60 or more nucleotides in length), although primers of any practical length may be useful in the practice of certain embodiments of the invention.

In one embodiment, the present invention provides oligonucleotide probes and primer sequences specific MDRO-associated genes. In illustrative embodiments, exemplary oligonucleotide primer sequences are disclosed that are useful in the detection and/or amplification of nucleic acid segments that are universal across to particular types, subtypes of MGRO-associated genes.

For example, in preferred embodiments the amplification and detection primers are chosen such that the primers are capable of specifically binding to most, if not all subtypes of a particular MDRO-associated gene. For example, the primer is chosen by identifying regions of homology across the subtypes and degenerate nucleotides are utilized to accommodate for the lack of 100% homology.

Preferably, the amplification primers and detection primers and probe bind in the same region of homology, i.e. the amplification primers and detection primers and probe are nested. In some aspects the primers used in the amplification step are different than the primers used in the detection step.

The primers and probes are designed such that a single set of forward and reverse amplification primers can be used for sample enrichment and a single set of forward and reverse detection primers and probe are capable of amplifying and detecting all 15 KPC subtypes or all nine NDM subtypes. For VIM, primers and probes are designed such that three sets of forward and reverse amplification primers can be used for sample enrichment and three sets of forward and reverse primers and probes are capable of amplifying and detecting all 40 VIM subtypes. For OXA, primers and probes are designed such that five sets of forward and reverse amplification primers can be used for sample enrichment and five sets of forward and reverse primers and probes are capable of amplifying and detecting all the OXA subtypes in the OXA-51, OXA-23, OXA-48, OXA-24/40 and OXA-58 subfamilies. For CTX-M, primers and probes are designed such that a five sets of forward and reverse amplification primers can be used for sample enrichment and five sets of forward and reverse primers are capable of amplifying and detecting all the CTX-M subtypes in the CTX-M-1, CTX-M-2, CTX-M-8, CTX-M-9 and CTX-25.

Alternatively the primers and probes are designed such that a single set of forward and reverse amplification primers can be used for sample enrichment and a single set of forward and reverse detection primers and probe are capable of amplifying and detecting a specific group of subtypes of an MDRO-associated gene. For example, OXA primers and probes are designed such that sets of forward and reverse amplification primers can be used for sample enrichment and sets of forward and reverse primers are capable of amplifying and detecting only OXA subtypes OXA-23, 49, 73, 146, 165, 167, 168, 169, 170, 171, 225, 239

In additional embodiments, exemplary oligonucleotide detection probe sequences are disclosed that are particularly useful in the detection and quantitation of amplification products arising from such polynucleotides. Detection of these products when indicative of the presence of these MDRO-specific polynucleotides in a clinical sample can provide clinical diagnosticians and other medical professionals with a means for predicting and/or confirming the likelihood of a MDRO infection in patients from whom such samples are collected. Such information may also be useful in the management of care for such individuals, and may also serve as molecular markers for determining the extent, significance, and/or rate of disease progression.

The oligonucleotide primers and probes of the present invention are designed for the selective amplification and detection of MDRO-associated gene encoding nucleic acid segments. disclosed primer sequences are suitable for use in hybridization methods, and in DNA amplification methods such as PCR-based amplification methods (including, for example, real-time PCR analyses). Likewise, the disclosed oligonucleotide detection probes are suitable for labeling with an appropriate label means for detection and quantitation of the products resulting from the amplification of nucleic acids using one or more pairs of the amplification primers disclosed herein.

In general, the oligonucleotide probes and primers finding particular utility in the practice of the disclosed methods should be of sufficient length to selectively hybridize to a complementary nucleic acid sequence, obtained from a clinical isolate of a mammalian patient that is suspected of having, or at risk for developing a MDRO infection.

In particular, oligonucleotide primers and probes are selected such that they selectively hybridize to specific complementary nucleic acid sequences upstream and downstream of a region of DNA that encompasses a nucleic acid sequence from an MDRO-associated gene. The selection of oligonucleotide probe and primer lengths is a process well-known in the molecular biological arts, and depends upon a number of parameters.

For most embodiments, the inventors contemplate that the length of the selected probe and primer compositions of the invention will preferably be less than about 50 to 60 or so nucleotides in length, and more preferably, will be less than about 40 to 45 or so nucleotides in length, while other probes and primers of the invention may be on the order of about 30 to 35 or so nucleotides in length. In some embodiments, the length of the selected oligonucleotide primer sequences (e.g., "forward" and "reverse" primers) and/or the length of the selected detection probe sequences (e.g., "anchor" and "sensor" probes), will likely be on the order of about 20 to 40 or so nucleotides in length, in some cases about 23 to about 40 nucleotides in length, or about 20 to about 30 nucleotides in length, although in some cases, the sizes of particular probes and primer sequences may be larger than that, and on the order of about 60 to 70 nucleotides in length. Alternatively, in some embodiments, it may be desirable to employ shorter probe and/or primer sequences, and as such, the oligonucleotides selected for practice of the invention may be on the order of about 15 to 28 or so nucleotides in length or even slightly shorter, such as about 15 to about 25 nucleotides, in some embodiments.

In the context of the present application, it is understood that all intermediate oligonucleotide lengths within the various ranges stated herein are contemplated to expressly fall within the scope of the present invention. To that end, oligonucleotides that are less than about 60, less than about 59, less than about 58, less than about 57, less than about 56, less than about 55, less than about 54, less than about 53, less than about 52, less than about 51, etc. are expressly within the scope of the present disclosure, as are oligonucleotides that are less than about 50, less than about 49, less than about 48, less than about 47, less than about 46, less than about 45, less than about 44, less than about 43, less than about 42, less than about 41, as well as oligonucleotides that are less than about less than about 40, less than about 39, less than about 38, less than about 37, less than about 36, less than about 35, less than about 34, less than about 33, less than about 32, less than about 31, as well as oligonucleotides that are less than about less than about 30, less than about 29, less than about 28, less than about 27, less than about 26, less than about 25, less than about 24, less than about 23, less than about 22, less than about 21, less than about 20, less than about 19, less than about 18, less than about 17, less than about 16, less than about 15, less than about 14, and so forth.

As used herein, "nucleic acid" or "polynucleotide" compositions include, but are not limited to, those that contain either single-stranded or double-stranded polynucleotides, such as for example, deoxyribonucleic acids (DNA), ribonucleic acids (RNA), peptide nucleic acids (PNA), or any combinations or derivatives thereof (including, e.g., genomic, extragenomic, plasmid, cosmid, recombinant, artificial, and/or synthetic). Such sequences may be coding or non-coding sequences, sense, non-sense, or anti-sense sequences, and may, but need not, be present within one or more populations or pluralities of polynucleotides (either of the present invention, and a polynucleotide may, but need not, be linked to other molecules and/or support materials.

Likewise, polynucleotides of the present invention, and particularly those functioning as probes and/or primers specific for one or more particular types, subtypes, or strains of MDRO-associated genes, need not be identical, or even substantially homologous to the particular sequences employed in the various embodiments of the invention illustrated herein. While the inventors have illustrated the use of particular probe and primer sequences as tools for identifying, amplifying, and quantitating a particular MDRO-associated gene subtype or strain, such primers and/or probe sequences need not contain the particular nucleotide sequences employed in the illustrative examples provided herein.

In fact, in certain circumstances, polynucleotides useful as probe and/or primer sequences may include any suitable sequences that may be obtained, prepared, modified, or synthesized for such purpose. Moreover, in some instances, it is preferable that the probe and primer sequences utilized specifically hybridize to their particular target sequences, and do not share significant homology or substantially bind to other viral, bacterial, or fungal species, or to the genome of the host organism from which the biological sample was originally obtained. Likewise, it is desirable that the various probes and primer compositions used for the detection of particular subtypes and/or strains of a given MDRO-associated gene also not cross-react, or hybridize to other or non-related nucleic acids that may also be present in the sample under assay.

As noted herein, the invention provides detection probes that contain at least a first sequence domain that specifically hybridizes (i.e., binds) to a suitably-detectable probe, including, without limitation, molecularly-labeled probes and derivatives thereof. Exemplary labeled probes are those that include radioactive, luminescent, chemiluminescent, fluorescent, enzymatic, magnetic, or spin-resonance labels known to those of ordinary skill in the molecular arts. In illustrative embodiments, the labeled probe contains at least a first minor groove binder. In certain embodiments, the detection probe may include a fluorescent label such as fluorescein, 6-carboxyfluorescein (6-FAM), or 6-carboxyfluoroscein-N-succinimidyl ester (6-FAMSE), VIC™ dye and the like, or a combination thereof.

In certain embodiments, to facilitate the binding of conventional detectable-label probes, the detection probes of the invention will contain at least a first sequence domain of from about 10 to about 60 nucleotides, in some instances about 10 to about 50 nucleotides, or about 10 to about 40 nucleotides, or about 10 to about 30 nucleotides, or about 10 to about 20 nucleotides in length that specifically binds to at least a first detectable probe. While the first sequence domain may be of any practical length within the entirety of the carrier sequence, preferably, the first sequence domain will be from about 12 to about 50 nucleotides in length; more preferably, from about 14 to about 45 nucleotides in length; still more preferably, from about 16 to about 40 or so nucleotides in length, and more preferably still, from about 18 to about 30 or so nucleotides in length.

As such, all intermediate lengths of probe-hybridizing sequence domains are contemplated to fall within the scope of the present disclosure, including, without limitation, probe-binding domains that are about 13 nucleotides in length, about 14 nucleotides in length, about 15 nucleotides in length, about 16 nucleotides in length, about 17 nucleotides in length, about 18 nucleotides in length, about 19 nucleotides in length, about 20 nucleotides in length, about 21 nucleotides in length, about 22 nucleotides in length, about 23 nucleotides in length, about 24 nucleotides in length, about 25 nucleotides in length, about 26 nucleotides in length, about 27 nucleotides in length, about 28 nucleotides in length, about 29 nucleotides in length, about 30 nucleotides in length, about 31 nucleotides in length, about 32 nucleotides in length, about 33 nucleotides in length, about 34 nucleotides in length, about 35 nucleotides in length, or even about 36, 37, 38, 39 or 40 or so nucleotides in length.

In exemplary embodiments, the amplification primers and detection probes may be prepared by one or more suitable molecular biology techniques, including, e.g., by the in vitro transcription of a polynucleotide that includes the sequence, or alternatively, includes a nucleic acid sequence that is complementary to the sequence.

Preferably, to this formulation a sufficient amount of primers and probe are added so as to amplify and detect the desired target.

In some embodiments, it may be desirable to provide reagent mixtures that include more than a single pair of amplification primers and a detection probe that is specific for a given target nucleic acid sequence. For example, when it is desirable to determine the presence of two or more MDRO-associated gene, the composition of the invention may be formulated to contain a first pair of amplification primers that specifically bind to at least a first target region of an KPC-specific polynucleotide, and a second pair of amplification primers that specifically bind to at least a first target region of an NMM, VIM, IMP, OXA, CTX-M, Van-A, MI, SME, GIM, SPM, NMC, SFC, SHV, TEM, BEL, VEB, GES, PER, SFO, BES, TLA, ACC, CMY, MIR, ACT, DHA, MOX, FOX, or CFE-specific polynucleotide.

In addition, when an internal positive control (IPC) is added to an initial collection solution or the extracted nucleic acid sample, the composition may be further or additionally formulated to include a first pair of amplification primers that specifically bind to at least a first target region of a particular IPC polynucleotide.

For detection of the particular amplification product(s) produced from such compositions, the compositions will also further include a first detection probe that specifically binds to the amplification product produced from the first pair of amplification primers, and a second distinct detection probe that specifically binds to the amplification product produced from the second pair of amplification primers. In such compositions, it is preferable that the two, three or four detection probes present in the formulation be distinct, such that each of the probes (if specifically bound to a target in the resulting amplification mixture) may be individually detectable using conventional methodologies. Such probe distinctiveness is readily achievable in the conventional arts, using, for example, detection probes that include detection moieties that fluoresce at two, three or four distinctly-different wavelengths.

In some aspects of the invention, the amplification and/or detection of target nucleic acids may be done sequentially, while in other aspects, it may be desirable to amplify and/or detection multiple target nucleic acids simultaneously. For example, a given biological sample could first be screened for the presence of KPC, and if none are found, the sample then secondarily screened for the presence of NDM, VIM, IMP, OXA, CTX-M, VAN-A MI, SME, GIM, SPM, NMC, SFC, SHV, TEM, BEL, VEB, GES, PER, SFO, BES, TLA, ACC, CMY, MIR, ACT, DHA, MOX, FOX, or CFE-specific target sequence(s).

The methods for nucleic acid hybridization are considered routine to those of ordinary skill in the molecular biological arts, and as such, a detailed discussion of analytical methods employing them need not be provided herein. However, as a guidance, "moderately stringent" hybridization conditions popularized by Southern et al. are generally considered in the art to include, e.g., pre-washing in a solution containing about 5× standard sodium citrate buffer (SSC), 0.5% sodium dodecyl sulfate (SDS), 1.0 mM ethylenediaminetetraacetic acid (EDTA) (e.g., pH 8.0); hybridizing at a temperature of from about 50° C. to about 60° C. in 5×SSC overnight; followed by washing twice at about 60 to 65° C. for 20 min. with each of 2×0.5× and 0.2×SSC containing 0.1% SDS). Likewise, "stringent" hybridization conditions typically include, e.g., pre-washing in a solution containing about 5×SSC, 0.5% SDS, 1.0 mM EDTA (pH 8.0); hybridizing at a temperature of from about 60° C. to about 70° C. in 5×SSC overnight; followed by washing twice at about 65 to 70° C. for 20 min with each of 2×, 0.5× and 0.2×SSC containing 0.1% SDS). Similarly, representative examples of "highly-stringent" hybridization conditions include, but are not limited to, pre-washing in a solution containing about 5×SSC, 0.5% SDS, 1.0 mM EDTA (pH 8.0); hybridizing at a temperature of from about 70° C. to about 75° C. in 5×SSC overnight; followed by washing twice at about 70° C. to about 75° C. for 20 mM with each of 2×, 0.5× and 0.2×SSC containing 0.1% SDS).

It will also be appreciated by those of ordinary skill in the art that, as a result of the degeneracy of the genetic code, there are many nucleotide sequences that encode a given primary amino acid sequence. Some of these polynucleotides bear minimal homology to the nucleotide sequence of any native gene. Nonetheless, polynucleotides that vary due to differences in codon usage are specifically contemplated by the present invention.

Detection probes and amplification primers may be prepared by conventional molecular biology recombination methodologies, or alternatively synthesized in whole or in part by conventional methods known in the art, including chemical synthesis (e.g., solid phase phosphoramidite chemical synthesis) and the like. Modifications in a polynucleotide sequence may also be introduced using standard mutagenesis techniques, such as oligonucleotide-directed site-specific mutagenesis. RNA molecules for use as detection probes or primers may also be directly synthesized, or alternatively, be prepared by in vitro or in vivo transcription of DNA sequences using suitable systems (such as T3, T7, and SP6 polymerases and the like).

Polynucleotides of the present invention may be modified to increase stability either in vitro and/or in vivo. Such modifications include, without limitation, the addition of flanking sequences at the 5'-end, 3'-end, or both; the use of phosphorothioate or 2'-o-methyl rather than phosphodiesterase linkages in the backbone; and/or the inclusion of nontraditional bases such as inosine, queosine and wybutosine, as well as acetyl-, methyl-, thio-, or otherwise-modified forms of adenine, cytidine, guanine, thymine and uridine, or any combination thereof.

Nucleotide sequences as described herein may be joined or linked to a variety of other nucleotide sequences using established recombinant techniques. For example, a polynucleotide useful as an amplification probe or detection primer may be produced by cloning into any of a variety of cloning vectors, including one or more of plasmids, phagemids, lambda phage derivatives and cosmids. Vectors of particular interest include expression vectors, replication vectors, probe generation vectors, and sequencing vectors. In general, a vector will contain an origin of replication functional in at least one organism, convenient restriction endonuclease sites and one or more selectable markers. Other elements will depend upon the desired use, and will be apparent to those of ordinary skill in the art. Alternatively, probe and primer-specific oligonucleotide sequences may be prepared through one or more template-dependent or amplicon-directed recombinant production methodologies that are known to those of ordinary skill in the arts.

In particular embodiments, the present invention provides polynucleotide compositions that may be added to the disclosed collection/storage/transport media to provide one or more amplification primer(s) and or detection probe(s) to analyze and/or characterize a population of target polynucleotides isolated, for example, from a biological sample or specimen. Such polynucleotide compositions may contain one or more sequence domains to which specific polymerases may bind, and may serve as suitable amplification primers, and/or detection probes.

Performance and Accuracy Measures of the Invention

The performance and thus absolute and relative clinical usefulness of the invention may be assessed in multiple ways as noted above. Amongst the various assessments of performance, some aspects of the invention are intended to provide accuracy in clinical diagnosis and prognosis.

In the categorical diagnosis of a disease state, changing the cut point or threshold value of a test (or assay) usually changes the sensitivity and specificity, but in a qualitatively inverse relationship. Therefore, in assessing the accuracy and usefulness of a proposed medical test, assay, or method for assessing a subject's condition, one should always take both sensitivity and specificity into account and be mindful of what the cut point is at which the sensitivity and specificity are being reported because sensitivity and specificity may vary significantly over the range of cut points. Use of statistics such as AUC, encompassing all potential cut point values, is preferred for most categorical risk measures when using the invention, while for continuous risk measures, statistics of goodness-of-fit and calibration to observed results or other gold standards, are preferred.

The methods of the invention are capable of detecting less than 250, 240, 230, 220, 215, 210, 200, 175, 165, 150, 100, 90, 80, 70, 60, 50, 40, 30, 20, 05 15 colony forming units per sample.

By predetermined level of predictability it is meant that the method provides an acceptable level of clinical or diagnostic accuracy. Using such statistics, an "acceptable degree of diagnostic accuracy", is herein defined as a test or assay (such as the test used in some aspects of the invention for determining the clinically significant presence of DETERMINANTS, which thereby indicates the presence an infection type) in which the AUC (area under the ROC curve for the test or assay) is at least 0.60, desirably at least 0.65, more desirably at least 0.70, preferably at least 0.75, more preferably at least 0.80, and most preferably at least 0.85.

By a "very high degree of diagnostic accuracy", it is meant a test or assay in which the AUC (area under the ROC curve for the test or assay) is at least 0.75, 0.80, desirably at least 0.85, more desirably at least 0.875, preferably at least 0.90, more preferably at least 0.925, and most preferably at least 0.95.

Alternatively, the methods predict the presence or absence of an MDRO with at least 75% total accuracy, more preferably 80%, 85%, 90%, 95%, 97%, 98%, 99% or greater total accuracy.

Alternatively, the methods predict the presence or absence of an MDRO with an MCC larger than 0.2, 0.3, 0.4, 0.5, 0.6, 0.7, 0.8., 0.9 or 1.0.

The predictive value of any test depends on the sensitivity and specificity of the test, and on the prevalence of the condition in the population being tested. This notion, based on Bayes' theorem, provides that the greater the likelihood that the condition being screened for is present in an individual or in the population (pre-test probability), the greater the validity of a positive test and the greater the likelihood that the result is a true positive. Thus, the problem with using a test in any population where there is a low likelihood of the condition being present is that a positive result has limited value (i.e., more likely to be a false positive). Similarly, in populations at very high risk, a negative test result is more likely to be a false negative.

As a result, ROC and AUC can be misleading as to the clinical utility of a test in low disease prevalence tested populations (defined as those with less than 1% rate of occurrences (incidence) per annum, or less than 10% cumulative prevalence over a specified time horizon).

A health economic utility function is an yet another means of measuring the performance and clinical value of a given test, consisting of weighting the potential categorical test outcomes based on actual measures of clinical and economic value for each. Health economic performance is closely related to accuracy, as a health economic utility function specifically assigns an economic value for the benefits of correct classification and the costs of misclassification of tested subjects. As a performance measure, it is not unusual to require a test to achieve a level of performance which results in an increase in health economic value per test (prior to testing costs) in excess of the target price of the test.

In general, alternative methods of determining diagnostic accuracy are commonly used for continuous measures, when a disease category has not yet been clearly defined by the relevant medical societies and practice of medicine, where thresholds for therapeutic use are not yet established, or where there is no existing gold standard for diagnosis of the pre-disease. For continuous measures of risk, measures of diagnostic accuracy for a calculated index are typically based on curve fit and calibration between the predicted continuous value and the actual observed values (or a historical index calculated value) and utilize measures such as R squared, Hosmer-Lemeshow P-value statistics and confidence intervals. It is not unusual for predicted values using such algorithms to be reported including a confidence interval (usually 90% or 95% CI) based on a historical observed cohort's predictions, as in the test for risk of future breast cancer recurrence commercialized by Genomic Health, Inc. (Redwood City, Calif.).

Various implementations of the subject matter described herein may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and may be implemented in a high-level procedural and/or object-oriented programming language, and/or in assembly/machine language. As used herein, the term "machine-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the subject matter described herein may be implemented on a computer having a display device (e.g., a CRT (cathode ray tube) or LCD (liquid crystal display) monitor) for displaying information to the user and a keyboard and a pointing device (e.g., a mouse or a trackball) by which the user may provide input to the computer. Other kinds of devices may be used to provide for interaction with a user as well; for example, feedback provided to the user may be any form of sensory feedback (e.g., visual feedback, auditory feedback, or tactile feedback); and input from the user may be received in any form, including acoustic, speech, or tactile input.

The subject matter described herein may be implemented in a computing system that includes a back-end component (e.g., as a data server), or that includes a middleware component (e.g., an application server), or that includes a front-end component (e.g., a client computer having a graphical user interface or a Web browser through which a user may interact with an implementation of the subject matter described herein), or any combination of such back-end, middleware, or front-end components. The components of the system may be interconnected by any form or medium of digital data communication (e.g., a communication network). Examples of communication networks include a local area network ("LAN"), a wide area network ("WAN"), and the Internet.

The computing system may include clients and servers. A client and server are generally remote from each other and typically interact through a communication network. The relationship of client and server arises by virtue of computer programs running on the respective computers and having a client-server relationship to each other.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

REFERENCES

AitMhand T, Soukri A, Moustaoui N, Amarouch H, ElMdgahri N, Sirot D, Benbachir M (2002) Plasmid-Mediated TEM-3 Extended-Spectrum Beta-Lactamase Production in *Salmonella typhimurium* in Casablanca. *J Antimicrob Chemother* 49: 169-172.

Arnold R, Thom K, Sharma M, Phillips M, Johnson K, Morgan D (2011) Emergence of *Klebsiella pneumoniae* Carbapenemase (KPC)-Producing Bacteria. *South Med J* 104: 40-45.

Bahar G, Mazzario A, Koncan R, Mert A, Fontana R, Rossolini G, Cornaglia G (2004) Detection of VIM-5 metallo-β-lactamase in a *Pseudomonas aeruginosa* clinical isolate from Turkey. *J Antimicrob Chemother* 54: 282-283.

Barnaud G, Arlet G, Verdet C, Gaillot O, Lagrange P, Philippon L (1998) *Salmonella enteritidis*: AmpC Plasmid-Mediated Inducible β-Lactamase (DHA-1) with an ampR Gene from *Morganella morganii*. *Antimicrob Agents Chemother* 42: 2352-2358.

Bauernfeind A, Schneider I, Jungwrith R, H S, Ullmann U (1999) A Novel Type of AmpC β-Lactamase, ACC-1, Produced by a *Klebsiella pneumoniae* Strain Causing Nosocomial Pneumonia. *Antimicrob Agents Chemother* 43: 1924-1931.

Bauernfeind A, Stemplinger I, Jungwrith R, Giamarellou H (1995) Characterization of the Plasmidic β-Lactamase CMY-2, Which Is Responsible for Cephamycin Resistance. *Antimicrob Agents Chemother:* 221-224.

Bauernfeind A, Stemplinger I, Jungwrith R, R W, Chong Y (1996) Comparative Characterization of the Cephamycinase blaCMY-1 Gene and Its Relationship with Other β-Lactamase Genes. *Antimicrob Agents Chemother* 40: 1926-1930.

Berrazeg M, Diene S, Medjahed P, Parola P, Drissi M, Raoult D, Rolain J (2014) New Delhi Metallo-Beta-Lactamase Around the World: An eReview Using Google Maps. *Eurosurveillance* 19: pii=20809.

Bonnet R, J L. S, Chanal Cea (2000) A Novel Class A Extended-Spectrum β-Lactamase (BES-1) in *Serratia marcescens* Isolated in Brazil. *Antimicrob Agents Chemother* 44: 3061-3068.

Bou G, Oliver A, Martinez-Beltran J (2000) OXA-24, a Novel Class D β-Lactamase with Carbapenemase Activity in an *Acinetobacter baumannii* Clinical Strain. *Antimicrob Agents Chemother* 44: 1556-1561.

Bradford P, Urban C, Mariano N, Projan S, Rahal J, Bush K (1997) Imipenem Resistance in *Klebsiella pneumoniae* is Associated with the Combination of ACT-1, a Plasmid-Mediated AmpC β-Lactamase, and the Loss of an Outer Membrane Protein. *Antimicrob Agents Chemother* 41: 563-569.

Carlos J, Beceiro A, Gutiérrez O, Alberti M, Perez J, Bou G, Oliver A (2008) Characterization of the New Metallo-β-Lactamase VIM-13 and Its Integron-Borne Gene from a *Pseudomonas aeruginosa* Clinical Isolate in Spain. *Antimicrob Agents Chemother* 52: 3589.

Castanheira C, Toleman M, Jones R, Schmidt F, Walsh T (2004) Molecular characterization of a β-Lactamase Gene, blaGIM-1, encoding a new subclass of Metallo-β-Lactamase. *Antimicrob Agents Chemother* 48: 4654-4661.

Chaves J, Landona M, Ladona G, Segura C, Coira A, Reig R, Ampurdanes C (2001) SHV-1 β-Lactamase is Mainly a Chromosomally Encoded Species-Specific Enzyme in *Klebsiella pneumoniae*. *Antimicrob Agents Chemother* 45: 2856-2861.

Corkill J, Cuevas L, Gurgel R, Greensill J, Anthony H (2001) SHV-27, A Novel Cefotaxime-Hydrolysing β-Lactamase, Identified in *Klebsiella pneumoniae* isolates from a Brazilian hospital. *Journal of Antimicrobial Chemotherapy* 47: 463-465.

Crowley B, Benedi V, Domenech-Sanchez A (2002) Expression of SHV-2 β-Lactamase and of Reduced Amounts of β OmpK36 Porin in *Klebsiella pneumoniae* Results in Increased Resistance to Cephalosporins and Carbapenems. *Antimicrob Agents Chemother* 46: 3679-3682.

Da Silva G, Correia M, Vital C, Ribeiro G, Sousa J, Leitaro R, Peixe L, Duarte A (2002) Molecular Characterization of blaIMP-5, a New Integron-Borne Metallo-β-lactamase Gene from an *Acinetobacter baumannii* Nosocomial Isolate in Portugal. FEMS Microbiology Letters 215: 33-39.

Dalla-Costa L, Coelho J, Souza A, Castro M, Stier C, Bragagnolo K, Rea-Neto A, Penteado-Filho S, Livermore D, Woodford N (2003) Outbreak of Carbapenem-Resistant *Acinetobacter baumannii* Producing the OXA-23 Enzyme in Curitiba, Brazil. *J Clin Micro* 41: 3403-3406.

Danel F, Hall L, Gur D, Livermore D (1997) OXA-15, an Extended-Spectrum Variant of OXA-2 β-Lactamase, Isolated from a *Pseudomonas aeruginosa* Strain. *Antimicrob Agents Chemother* 41: 785-790.

Fonseca F, Sarmento A, Henriques I, Samyn B, van Beeumen J, Domingues P, Domingues M, Saavedra M, Correia A (2007) Biochemical Characterization of SFC-1, a Class A Carbapenem-Hydrolyzing β-Lactamase. *Antimicrob Agents Chemother* 51: 4512.

Girlich D, Naas T, Nordmann P (2004a) Biochemical Characterization of the Naturally Occurring Oxacillinase OXA-50 of *Pseudomonas aeruginosa*. *Antimicrob Agents Chemother* 48: 2043-2048.

Girlich D, Naas T, Nordmann P (2004b) OXA-60, a Chromosomal, Inducible, and Imipenem-Hydrolyzing Class D β-Lactamase from *Ralstonia pickettii*. *Antimicrob Agents Chemother* 48: 4217-4225.

Gutmann L, Ferre B, Goldstein F, Rizk N, Pinto-Schuster E, Acar J, Collatz E (1989) SHV-5, a Novel SHV-Type r-Lactamase that Hydrolyzes Broad-Spectrum Cephalosporins and Monobactams. *Antimicrob Agents Chemother* 33: 951-956.

Gutmann L, Kitzis M, Billot-Klein D, Goldstein F, Tran Van Nhieu G, Lu T, Carle J, Collatz E, Williamson R (1988) Plasmid-Mediated Beta-Lactamase (TEM-7) Involved in Resistance to Ceftazidime and Aztreonam. *Rev Infect Dis* 10: 860-866.

Héritier C, Poirel P, Nordmann P (2004) Genetic and Biochemical Characterization of a Chromosome-Encoded Carbapenem-Hydrolyzing Ambler Class D β-Lactamase from *Shewanella algae*. *Antimicrob Agents Chemother* 48: 1670-1675.

Horii T, Arakawa Y, Ohta M, Sugiyama R, Wacharotayankun R, Ito H, Kato N (1994) Characterization of a Plasmid-Borne and Constitutively Expressed blaMOX-1 Gene Encoding AmpC-Type β-Lactamase. *Gene* 139: 93-98.

Jeong S, Bae I, Lee J, Sohn S, Kang G, Jeon G, Kim Y, Jeong B, Lee S (2004) Molecular Characterization of Extended-Spectrum Beta-Lactamases Produced by Clinical Isolates of *Klebsiella pneumoniae* and *Escherichia coli* from a Korean Nationwide Survey. *J Clinic Microb* 42: 2902-2906.

Koh T, Bahini G, Hall L (2001) Carbapenem-Resistant *Klebsiella pneumoniae* in Singapore Producing IMP-1 β-Lactamase and Lacking an Outer Membrane Protein. *Antimicrob Agents Chemother* 45: 1939-1940.

Lakshmi R, nusrin K, Sharon G, Sreelakshimi K (2014) Role of Beta Lactamases in Antibiotic Resistance: a Review. *Int Res J Pharm* 5: 37-40.

Lee K, Hwa Yum J, Yong D, Lee M, Kim H, Docquier J, Rossolini G, Chong Y (2005) Novel Acquired Metallo-β-Lactamase Gene, blaSIM-1, in a Class 1 Integron from *Acinetobacter baumannii* Clinical Isolates from Korea. *Antimicrob Agents Chemother* 49: 4485-4491.

Matsumoto Y, Inoue M (1999) Characterization of SFO-1, A Plasmid-Mediated Inducible Class A β-Lactamase from *Enterobacter cloacae*. *Antimicrob Agents Chemother* 43: 307-313.

Mazzariol A, Roelofsen E, Koncan R, Voss A, Cornaglia G (2007) Detection of a New SHV-Type Extended-Spectrum β-Lactamase, SHV-31, in a *Klebsiella pneumoniae* Strain Causing a Large Nosocomial Outbreak in the Netherlands. *Antimicrob Agents Chemother* 51: 1082-1084.

Miro E, Mirelis B, Navarro F, Matas L, Gimenez M, Rabaza C (2005) *Escherichia coli* Producing an ACC-1 Class C β-Lactamase Isolated in Barcelona, Spain. *Antimicrob Agents Chemother* 49: 866-867.

Mossakowska D, Ali N, Dale J (1989) Oxacillin-Hydrolysing β-Lactamases, A Comparative Analysis at Nucleotide and Amino Acid Sequence Levels. *Eur J Biochem* 180: 309-318.

Mugnier P, Dubrous P, Casin I, Arlet G, Collatz E (1996) A TEM-Derived Extended-Spectrum Beta-Lactamase in *Pseudomonas aeruginosa. Antimicrob Agents Chemother* 40: 2488-2493.

Mulvey M, Bryce E, Boyd D, Ofner-Agostini M, Christianson S, Simor A, Paton S (2004) Ambler Class A Extended-Spectrum Beta-Lactamase-Producing *Escherichia coli* and *Klebsiella* spp. in Canadian Hospitals. *Antimicrob Agents Chemother* 48: 1204-1214.

Naas T, Nordmann P (1999) Oxa-Type β-Lactamases. *Current Pharmaceutical Design* 5: 865-879.

Naas T, Oxacelay C, Nordmann P (2007) Identification of CTX-M-Type Extended-Spectrum-β-Lactamase Genes Using Real-Time PCR and Pyrosequencing. *Antimicrob Agents Chemother* 51: 223-230.

Naas T, Poirel L, Nordmann P (2008) Minor Extended-Spectrum β-Lactamases. *Clin Microbiol Infect* 14: 42-52.

Nakano R, Okamoto R, Nakano Y, Kaneko K, Okitsu N, Hosaka Y, Inoue M (2004) CFE-1, A Novel Plasmid-Encoded AmpC β-Lactamase with an ampR Gene Originating from *Citrobacter freundii. Antimicrob Agents Chemother* 48: 1151-1158.

Nordmann P, Naas T (1994) Sequence Analysis of PER-1 Extended-Spectrum Beta-Lactamase from *Pseudomonas aeruginosa* and Comparison with Class A β-Lactamases. *Antimicrob Agents Chemother* 38: 104-114.

Opazo A, domingues M, Bello H, Amyes S, Gonzalez-Rocha G (2012) OXA-Type Carbapenemases in *Acinetobacter baumannii* in South America. *J Infect Dev Ctries* 6: 311-316.

Papanicolaou G, Medeiros A, Jacoby G (1990) Novel Plasmid-Mediated 1-Lactamase (MIR-1) Conferring Resistance to Oxyimino- and ot-Methoxy 1-Lactams in Clinical Isolates of *Klebsiella pneumoniae. Antimicrob Agents Chemother* 34: 2200-2209.

Perilli M, Segatore B, Massis M, Franceschini N, Bianchi C, Rossolini G, Amicosante G (2002) Characterization of a New Extended-Spectrum β-Lactmase (TEM-87) Isolated in *Proteus mirabilis* during an Italian Survey. *Antimicrob Agents Chemother* 46: 925-928.

Philippon A, Arlet G, Jacoby G (2002) Plasmid-Determined AmpC-Type β-Lactamases. Minireiew. *Antimicrob Agents Chemother* 46: 1-11.

Philippon L, Naas T, AT B, V B, P N (1997) OXA-18, a Class D Clavulanic Acid-Inhibited Extended-Spectrum β-Lactamase from *Pseudomonas aeruginosa. Antimicrob Agents Chemother* 41: 2188-2195.

Poirel L, Brinas L, Verlinde A, Ide L, Nordmann P (2005a) BEL-1 A Novel Clavulanic Acid-Inhibited Extended-Spectrum β-lactamase, and the Cass 1 Integron In120 in *Pseudomonas aeruginosa. Antimicrob Agents Chemother:* 3743-3748.

Poirel L, He'ritier C, Tolun V, Nordmann P (2004a) Emergence of Oxacillinase-Mediated Resistance to Imipenem in *Klebsiella pneumoniae. Antimicrob Agents Chemother* 48: 15-22.

Poirel L, Le Thomas I, Naas T, Karim A, Nordmann P (2000) Biochemical Sequence Analyses of GES-1, A Novel class A Extended Spectrum β-Lactamase, and the Class 1 Integron In52 from *Klebsiella pneumoniae. Antimicrob Agents Chemother* 44: 622-632.

Poirel L, Marque S, Heritier C, Segonds G, Nordmann P (2005b) OXA-58, A Novel Class D β-Lactamase Involved in Resistance to Carbapenems in *Acinetobacter baumannii. Antimicrob Agents Chemother* 49: 202-208.

Poirel L, Naas T, Guibert M, Chaibi E, Labia R, Nordmann P (1999) Molecular and Biochemical Characterization of VEB-1, A Novel Class A Extended-Spectrum β-Lactamase Encoded by an *Escherichia coli* Integron Gene. *Antimicrob Agents Chemother* 43: 573-581.

Poirel P, Gerome P, De Champs C, Stephanazzi J, Naas T, Nordmann P (2002) Integron-Located oxa-32 Gene Cassette Encoding an Extended-Spectrum Variant of OXA-2 β-Lactamase from *Pseudomonas aeruginosa. Antimicrob Agents Chemother* 46: 566-569.

Poirel P, He'ritier C, Nordmann P (2004b) Chromosome-Encoded Ambler Class D β-Lactamase of *Shewanella oneidensis* as a Progenitor of Carbapenem-Hydrolyzing Oxacillinase. *Antimicrob Agents Chemother* 48: 348-351.

Pottumarthy S, Smith Moland E, Juretschko S, Swanzy S, Thomson K, Fritsche T (2003) NmcA Carbapenem Hydrolyzing Enzyme in *Enterobacter cloacae* in North America. *Emerging Infectious Diseases* 9: 999-1002.

Queenan A M, Torres-Viera C, Gold H, Carmeli Y, Eliopoulos G, Moellering Jr R, Quinn J, Hindler J, Medeiros A, Bush K (2000) SME-Type Carbapenem-Hydrolyzing Class Diverse *Serratia marcescens* Strains A β-Lactamases from Geographically diverse *Serratia marcescens* strains. *Antimicrob Agents Chemother* 44: 3035-3039.

Quinn J, Miyashiro B, Sahm D, Flamm R, Bush K (1989) Novel Plasmid-Mediated f-Lactamase (TEM-10) Conferring Selective Resistance to Ceftazidime and Aztreonam in Clinical Isolates of *Klebsiella pneumoniae. Antimicrob Agents Chemother* 33: 1451-1456.

Raghunath D (2010) New metallo β-lactamase NDM-1. *Indian J Med Res* 132: 478-481.

Rasmussen B, Bush K, Keeneym D, Yang Y, Hare R, O'Gara C, Medeiros A (1996) Characterization of IMI-1 β-Lactamase, a Class A Carbapenem-Hydrolyzing Enzyme from *Enterobacter cloacae. Antimicrob Agents Chemother* 40: 2080-2086.

Sacha P, Ostas A, Jaworowska J, Wieczorek P, Ojdam D, Ratajczak J, Tryniszewka E (2009) The KPC Type β-Lactamases: New Enzymes that Confer Resistance to Carbapenems in Gram-negative Bacilli. *Folia Histochemica Et Cytobiologica* 47: 537-543.

Schneider S, Queenan A M, Bauernfeind A (2006) Novel Carbapenem-Hydrolyzing Oxacillinase OXA-62 from *Pandoraea pnomenusa. Antimicrob Agents Chemother* 50: 1330-1335.

Silva J, Aguilar C, Ayala G (2000) TLA-1: A New Plasmid-mediated Extended-Spectrum β-Lactamase from *Escherichia coli. Antimicrob Agents Chemother* 44: 997-1003.

Taneja N, Singh G, Singh M, Madhu [S, Pahil S, Sharma M (2012) High Occurrence of blaCMY-1 AmpC Lactamase Producing *Escherichia coli* in Cases of Complicated Urinary Tract Infection (UTI) from a Tertiary Health Care Centre in North India. *Indian J Med Res* 136: 289-291.

Toleman M, Rolston K, Jones R, Timothy R (2004) Evolutionarily Distinct Metallo-β-Lactamase Gene in a *Pseudomonas aeruginosa* Isolate from the United States. *Antimicrob Agents Chemother* 48: 329.

Toleman M, Rolston K, Jones R, Walsh T (2003) Molecular and Biochemical Characterization of OXA-45, an Extended-Spectrum Class 2d-β-Lactamase in *Pseudomonas aeruginosa. Antimicrob Agents Chemother* 47: 2859-2863.

Toleman M, Simm A, Murphy T, Gales A, Biedenbach D (2002) Molecular characterization of SPM-1, A Novel Metallo-β-Lactamase Isolated in Latin America: Report from the SENTRY Antimicrobial Surveillance Programme. *Journal of Antimicrobial Chemotherapy* 50: 673-679.

Vahaboglu H, Budak F, Kasap M, Gacar G, Torol S, Karadenizli A, Kolayli F, Eroglu C (2006) High Prevalence of OXA-51-Yype class D β-Lactamases Among Ceftazidime-Resistant Clinical lisolates of *Acinetobacter* spp.: Co-Existence with OXA-58 in Multiple Centres. *J Antimicrob Chemother* 58: 537-542.

Walsh T, Toleman M, Poirel L, Nordmann P (2005) Metallo-β-Lactamases: the Quiet before the Storm? *Clin Microbiol Rev* 18: 306-325.

Yigit H, Queenan A, Anderson G, Domenech-Sanchez A, Biiddle J, Steward C, Alberti S, Bush K, Tenover F (2001) Novel Carbapenem-Hydrolyzing β-Lactamase, KPC-1, from a Carbapenem-Resistant Strain of *Klebsiella pneumoniae*. *Antimicrob Agents Chemother* 45: 151-1161.

Yong D, Toleman M, Giske C, Cho H, Sudman K, Lee K, Walsh T (2009) Characterization of a New Metallo-β-Lactamase Gene, blaNDM-1, and a Novel Erythromycin Esterase Gene Carried on a Unique Genetic Structure in *Klebsiella pneumoniae* Sequence Type 14 from India. *Antimicrob Agents Chemother* 53: 5046-5054.

EXAMPLES

Example 1: Specimen Handling

The MDRO test uses anal swabs collected using ESwabs™ from Copan or Becton Dickinson (BD). Collected ESwabs™ should be properly labeled, stored and transported to OpGen at room temperature (20-25 C) or 4 to 8 C. ESwabs™ should be tested within 48 hours of collection.

Example 2: PCR Primer and Probe Sequences

Exemplary primer and probe sequences useful in the methods of the invention include those listed below in Tables 2, 8 and 9. It is readily apparent to those skilled in the art that other primer and probe sequence may be utilized in practicing the claimed methods.

TABLE 2

| Reagent or Media | Sequence |
| --- | --- |
| Internal Amplification Control | GATTGCCACGCATTGAGCTAgcgagtcagcgataagcatgacgcgctttcaagc gtcgcgagtatgtgaaccaaggctccggacaggactatatacttgggtTTGATCTC GCCCCGACAAGAACGGGATTGACTGTTTGACActagctggtgttcggttcggtaa cggagaatctgtggggctatgtcactaatactttcgaaacgccccgtaccgatgcT GAACAAGTCGATGCAGGCTGGATGAGTGTGACGGAGTGTAactcgatgagttac ccgctaatcgaactgggcgagagatcccagcgctgatgcactcgatcccgaggcct gacccgacaTATCAGCTCAGACTAGAGCGGGCTGCGCATAAGCAAATGAC aattaaccactgtgtactcgttataacatctggcagttaaagtcgggagaatagga gccgcaatacacagtttaccgcatctagacctaacTGAGATACTGCCATAGACGAC T (SEQ ID NO: 1) |
| kpc-FO | GGAACCATTCGCTAAACTCGAAC (SEQ ID NO: 2) |
| kpc-RO | AATGAGCTGCACAGTGGGAA (SEQ ID NO: 3) |
| ndm-FO | CGGCCACACCAGTGACAATA (SEQ ID NO: 4) |
| ndm-RO | TGCTCAGTGTCGGCATCAC (SEQ ID NO: 5) |
| vim-FO | CCACGCATTCTCTAGAAGGAC (SEQ ID NO: 6) |
| vim-RO | GCTGACGGGACGTATACAAC (SEQ ID NO: 7) |
| vim-FOb | CCACGCACTCTCTAGAAGGAC (SEQ ID NO: 8) |
| vim-ROb | GCAGACGGGACGTACACAAC (SEQ ID NO: 9) |
| IAC-FO | GAACGGGATTGACTGTTTGACA (SEQ ID NO: 10) |
| IAC-RO | AGCCTGCATCGACTTGTTCA (SEQ ID NO: 11) |
| oxa(A)-FO | TGGTTGGGGATGGGATGTA (SEQ ID NO: 12) |
| oxa(A)-RO | TTTCGAACAGAGCTAGGTATTCC (SEQ ID NO: 13) |
| oxa(B)-FO | GCCGCGCAAATACAGAATAT (SEQ ID NO: 14) |
| oxa(B)-RO | ACCTTTTCTCGCCCTTCCAT (SEQ ID NO: 15) |
| oxa(C)-FO | AGCAAAGGAATGGCAAGAAAACA (SEQ ID NO: 16) |
| oxa(C)-RO | GCTTGGTTCGCCCGTTTAA (SEQ ID NO: 17) |
| imp-FOe | CC(Pu)GG(Pu)CACACTC(C/A)AGATAAC (SEQ ID NO: 18) |
| imp-ROd | GCCA(A/T)GCTTCTA(A/T)ATTTGCGTCA(Py) (SEQ ID NO: 19) |
| vanA-FO | AAATACGAGCCGTTATACATTGG (SEQ ID NO: 20) |
| vanA-RO | TTTATCCGGCGAGAGTACAG (SEQ ID NO: 21) |

TABLE 2-continued

| Reagent or Media | Sequence |
|---|---|
| ctx(A)-FO | GCTGTGTTAATCAATGCCACAC (SEQ ID NO: 22) |
| ctx(A)-RO | CGTCACGCTGTTGTTAGGAA (SEQ ID NO: 23) |
| ctx(B)-FO | GCGACCTGGTTAACTACAATCC (SEQ ID NO: 24) |
| ctx(B)-RO | GCAATCAGCTTATTCATGGCAGTA (SEQ ID NO: 25) |
| kpc-FI | AGGACTTTGGCGGCTCCAT (SEQ ID NO: 26) |
| kpc-RI | CTCAGCGCGGTAACTTACAGTTG (SEQ ID NO: 27) |
| ndm-FI | GATCGACGGCACCGACAT (SEQ ID NO: 28) |
| ndm-RI | CGAGATTGCCGAGCGACTT (SEQ ID NO: 29) |
| vim-FI | GTGCGCTTCGGTCCAG (SEQ ID NO: 30) |
| vim-RI | CAGATTGTCGGTCGAATGC (SEQ ID NO: 31) |
| vim-Rib | TAAGTTGTCGGTCGAATGC (SEQ ID NO: 32) |
| oxa(A)-FI | ACCCACAAGTAGGCTGGTTA (SEQ ID NO: 33) |
| oxa(A)-RI | TTTCTAAGTTAAGGGAGAACGCTAC (SEQ ID NO: 34) |
| oxa(B)-FI | GTGCCAGCCTCTACATTT (SEQ ID NO: 35) |
| oxa(B)-RI | TCATTAATATCCGTTTTCTGGTTC (SEQ ID NO: 36) |
| oxa(C)-FI | AGTTGGAATGCTCACTTTACTGA (SEQ ID NO: 37) |
| oxa(C)-RI | GGTAAATCCTTGCTGCTTATTCTC (SEQ ID NO: 38) |
| imp-FI | GTAGTGGTTTGG(Py)T(Pu)CCTGAA (SEQ ID NO: 39) |
| imp-RI | CCGTACGGTTTAA(Py)AAA(Pu)CAACCA (SEQ ID NO: 40) |
| vanA-FI | AATTACGAAATCTGGTGTATGGAAAATGTG (SEQ ID NO: 41) |
| vanA-RI | CTGAATAGCAATTGTCGTTTTCCCATT (SEQ ID NO: 42) |
| ctx(A)-FI | AGTCT(G/T)CCTCCCGACTG (SEQ ID NO: 43) |
| ctx(A)-RI | GCAAACGGCGGACGTA (SEQ ID NO: 44) |
| ctx(B)-FI | TTGCGGAGAAACACGTTA (SEQ ID NO: 45) |
| ctx(B)-RI | GCTATACTGCAGCGCC (SEQ ID NO: 46) |
| IAC-FI | GCTGGTGTTCGGTTCGGTAA (SEQ ID NO: 47) |
| IAC-RI | CATCGGTACGGGGCGTTT (SEQ ID NO: 48) |
| kpc-P | TATCCATCGCGTACAC (SEQ ID NO: 49) |
| ndm-P | TCAAGGACAGCAAG (SEQ ID NO: 50) |
| vim-Pd | CAGCACCAGGATAG (SEQ ID NO: 51) |
| vim-Pe | CAGCACCGGGATAG (SEQ ID NO: 52) |
| IAC-P | CCACAGATTCTCCG (SEQ ID NO: 53) |
| oxa(A)-P | TTGAGGCTGAACAA (SEQ ID NO: 54) |
| oxa(B)-P | CCCTGATCGGATTG (SEQ ID NO: 55) |
| oxa(C)-P | CTACGCCCTGTGATT (SEQ ID NO: 56) |
| imp-P | CCGAATAATATTTTCCTT (SEQ ID NO: 57) |
| imp-Pf | CCGAATAAAATTTTCTT (SEQ ID NO: 58) |
| vanA-Pc | CCGCGCAAGGTTTTTC (SEQ ID NO: 59) |

TABLE 2 -continued

| Reagent or Media | Sequence |
|---|---|
| ctx(A)-P | CGGCAAGTTTTTGC (SEQ ID NO: 60) |
| ctx(B)-P | CCAAGCTCAGCCA (SEQ ID NO: 61) |

Example 3: Quality Control

Controls for MDRO Assay are used at 3 different levels. First one represents a set of controls (NEC, PEC, NTC and the Internal Amplification Control (IAC) reaction) that are required to qualify a given assay run and are defined as "Assay Run controls". These controls are evaluated first for any given assay run and once accepted, the second level of controls (NEC, PEC, and NTC for each target) are assessed for each of the MDRO targets in the Assay run. This second level of controls qualifies a given target and is defined as "Target Controls". Once a given target is accepted, results for each sample are evaluated against a third level that represents an Internal Amplification Control (IAC) for each and every sample to evaluate inhibition of amplification and/or detection.

The positive extraction control (PEC) monitors for any reagent failure during RT-PCR. The negative extraction control (NEC) detects reagent or environment contamination by any target DNA through the sample acquisition, sample DNA, extraction, and through RT-PCR. The NTC detect reagents or environment contamination by any target DNA. The IAC controls for specimen inhibition.

Example 4: Sample Enrichment

Sample Enrichment Master Mix Preparation

Prepare three plate maps and calculate the working assay reagents for the number of specimens and controls being tested for each of the sample enrichment plates. Each plate must contain a minimum of one specimen, one positive extraction control (PEC), one negative extraction control (NEC), and one negative template control (NTC).

Sample Enrichment Plate Preparation

For sample enrichment plate containing assay reagent mix A: Load 9 µl of DNA template to each well according to plate map. Load 9 µl of PEC to the PEC well(s) and load 9 µl of NEC to the NEC well(s). Load 10 µl of molecular grade water to the no template control (NTC wells(s)). For sample enrichment plates containing master mix B and C: Load 10 µl of sample DNA template to each sample well according to plate map. Load 10 µl of molecular grade water to the no template control NTC wells(s).

Example 5: Amplification

Internal Amplification Control

Prepare an internal amplification control solution that contains 100 copies/µl of the internal amplification control sequence plus carrier calf thymus DNA in water.

To the sample enrichment plate containing assay reagent mix A, add 1 µl of internal amplification control (100 copies/µl) to all wells containing specimens, PEC, and NEC. The NTC does not receive IAC.

Verify and run cycling conditions according to Table 3 below.

TABLE 3

| Program Name | Temperature (° C.) | No. of Cycles | Time (min) |
|---|---|---|---|
| UDG | 50 | 1 | 2.00 |
| Pre-Incubation | 95 | 1 | 10.00 |
| Amplification | — | 25 | — |
| — | 95 | — | 00:15 |
| — | 61 | — | 01:00 |
| Cooling | 4 | — | ∞ |

Exonuclease I preparation

Calculate the working exonuclease I solution for the number of specimens and controls being pooled from the sample enrichment plates.

Prepare working exonuclease I solution according to the calculations.

Pooling Sample Enrichment Plates

Remove the three sample enrichment plates from the thermocylcers.

Transfer 5 µl from each well of the three plates to the 96-well plate containing exonuclease I working solution. Be sure to maintain well location during transfer. A1 from each of the sample enrichment plates gets pooled to A1 of the pooling/exonuclease I plate.

Exonuclease I Digestion

Load plate onto the thermocycler.

Verify and run cycling conditions according to Table 4 below.

TABLE 4

| Program Name | Temperature (° C.) | No. of Cycles | Time (min) |
|---|---|---|---|
| Digestion | 37 | 1 | 30:00 |
| Inactivation | 80 | 1 | 15:00 |
| Cooling | 4 | 1 | ∞ |

BioMark Sample Master Mix Preparation

Prepare plate map and calculate the working master mix for the number of specimens and controls being tested.

Prepare working BioMark Sample Master Mix for 210 samples according to Table 5 below.

TABLE 5

| Component | Starting Concentration | Amount Needed for 210 reactions | Final Concentration |
|---|---|---|---|
| PCR Master Mix | 2x | 630 | 1x |
| GE Sample Loading Reagent | 20x | 63 | 1x |
| Magnesium Chloride | 8.33x | 151.2 | 1x |

Aliquot 105 µl of BioMark sample master mix into each well of a single strip tube.

Using a multichannel pipette load 4.02 µl into the appropriate wells of two clean 96-well plates.

Example 6: Detection

Prepare plate map and calculate working assay solutions (Table 6).

TABLE 6

| Component |
| --- |
| KPC Assay |
| kpc-FI<br>kpc-RI<br>kpc-P<br>2x Assay Loading Reagent<br>Water |
| NDM Assay |
| ndm-FI<br>ndm-RI<br>ndm-P<br>2x Assay Loading Reagent<br>Water |
| VIM(A) Assay |
| vim-FI<br>vim-RI<br>vim-Pd<br>2x Assay Loading Reagent<br>Water |
| VIM(B) Assay |
| vim-FI<br>vim-Rib<br>vim-Pd<br>2x Assay Loading Reagent<br>Water |
| VIM(C) Assay |
| vim-FI<br>vim-RI<br>vim-Pe<br>2x Assay Loading Reagent<br>Water |
| IC Assay |
| IAC-FI<br>IAC-RI<br>IAC-P<br>2x Assay Loading Reagent<br>Water |
| OXA A Assay |
| oxa(A)-FI<br>oxa(A)-RI<br>oxa(A)-P<br>2x Assay Loading Reagent<br>Water |
| OXA B Assay |
| oxa(B)-FI<br>oxa(B)-RI<br>oxa(B)-P<br>2x Assay Loading Reagent<br>Water |
| OXA C Assay |
| oxa(C)-FI<br>oxa(C)-RI<br>oxa(C)-P<br>2x Assay Loading Reagent<br>Water |
| IMP(A) Assay |
| imp-FI<br>imp-RI<br>imp-P<br>2x Assay Loading Reagent<br>Water |

TABLE 6-continued

| Component |
| --- |
| IMP(B) Assay |
| imp-FI<br>imp-RI<br>imp-Pf<br>2x Assay Loading Reagent<br>Water |
| Van A Assay |
| vanA-FI<br>vanA-RI<br>vanA-P<br>2x Assay Loading Reagent<br>Water |
| CTX-M(A) Assay |
| ctx(A)-FI<br>ctx(A)-RI<br>ctx(A)-P<br>2x Assay Loading Reagent<br>Water |
| CTX-M(B) Assay |
| ctx(B)-FI<br>ctx(B)-RI<br>Ctx(B)-P<br>2x Assay Loading Reagent<br>Water |
| . L R |
| 2x Assay Loading Reagent<br>Water |

Sample Dilution

Post exonuclease I digestion remove plate from thermocycler.

Add 54 µl of 1× Tris EDTA to each well of the exdonuclease plate and mix.

BioMark Sample Plate Preparation

Retrieve the 96-well plate containing the previously made sample master mix and the 96-well plate containing the diluted sample.

Transfer using a multichannel pipette 1.98 µl of diluted sample to the corresponding well in the sample master mix plate (i.e. well A1 from the diluted sample plate is transferred to A1 in the sample master mix plate.

Mix each sample.

Loading the BioMark Chip

Prepare plate map for the BioMark Chip.

Remove BioMark chip from package

Inject control line fluid into the accumulator 2 on the chip. Be sure to use syringes labeled 192.24 with 150 µl of control line fluid.

Transfer 3 µl from each well of the sample master mix plate to the appropriate sample inlet on the 192.24 BioMark Chip.

Transfer 3 µl of the working assay solution for each assay to the appropriate assay inlet on the 192.24 BioMark Chip.

Pipette 150 µl of actuation fluid into the P1 well on the chip.

Pipette 150 µl of pressure fluid into the P2 and P3 wells on the chip.

Pipette 20 µl of pressure fluid into the P4 and P5 wells on the chip.

If necessary, blot the carrier surface with a dry, lint-free cloth.

Remove and discard the blue protective film from the bottom of the chip.

Open the tray on the IFC controller RX by selecting eject on the touchscreen.

Place the chip in the controller tray with the barcode facing out. Select close tray on the touch screen.

Using the IFC controller RX software, run the Load Mix (169×) script to load the samples and assays into the chip.

The IFC controller will display a run screen giving an estimated time of completion.

BioMark HD Loading and Operation

Remove loaded Biomark Chip from the IFC controller Rx.

Analyze the BioMark Chip using the following program with other appropriate instrument settings and methods of data analysis.

TABLE 7

| Program Name | Temperature (° C.) | No. of Cycles | Time (min) |
|---|---|---|---|
| Pre-Incubation | 95 | 1 | 10.00 |
| Amplification | — | 30 | — |
| — | 95 | — | 00:15 |
| — | 60 | — | 01:00 |

TABLE 8

Primer probe design

| Assay | FO Name | FO Sequence | RO Name | RO Sequence | Fi Name | Fi Sequence | Ri Name | Ri Sequence | Probe Name | Probe Sequence | Gene Subtypes Covered* | Amplicon |
|---|---|---|---|---|---|---|---|---|---|---|---|---|
| Kpc1a | kpc1a-FO | GGAAC CATTC GCTAA ACTCG AAC (SEQ ID NO: 2) | kpc1a-RO | AATGA GCTGC ACAGT GGGAA (SEQ ID NO: 3) | kpc1a-Fi | AGGAC TTTGG CGGCT CCAT (SEQ ID NO: 26) | kpc1a-Ri | CTCAG CGCGG TAACT TACAG TTG (SEQ ID NO: 27) | kpc1a-pb | TATCC ATCGC GTACA C (SEQ ID NO: 49) | KPC-1 thru KPC-16 | GGAACCAT TCGCTAAA CTCGAACA GGACTTTG GCCGGCTCC ATCGGTGT GTACGCGA TGGATACC GGCTCAGG CGCAACTG TTAAGTTA CCGGCGTG AGGAGCGC TTCCCACT GTGCAGCT CATT (SEQ ID NO: 68) |
| Ndm1c | ndm1c-FO | CGGCC ACACC AGTGA CAATA (SEQ ID NO: 4) | ndm1c-RO | TGCTC AGTGT CGGCA TCAC (SEQ ID NO: 5) | ndm1c-Fi | GATCG ACGGC ACCGA CAT (SEQ ID NO: 28) | ndm1c-Ri | CGAGA TTGCC GAGCG ACTT (SEQ ID NO: 29) | Ndm1c-pd | TCAAG GACAG CAAG (SEQ ID NO: 50) | NDM-1 thru 9 | CGGCCACA CCAGTGAC AATATCAC CGTTGGGA TCGACGGC ACCGACAT CGCTTTTG GTGGCTGC CTGATCAA GGACAGCA AGGGCCAA GTCGCTCG GCAATCTC GGTGATGC CGACACTG AGCA (SEQ ID NO: 69) |
| Vim2b (1st assay) | vim2b-FO | CCACG CATTC TCTAG AAGGA C (SEQ ID NO: 6) | vim2b-RO | GCTGA CGGGA CGTAT ACAAC (SEQ ID NO: 7) | vim2b-Fi | GTGCG CTTCG GTCCA G (SEQ ID NO: 30) | vim2b-Ri | CAGAT TGTCG GTCGA ATGC (SEQ ID NO: 31) | Vim2b-pd | CAGCA CCAGG ATAG (SEQ ID NO: 51) | VIM-1, 4, 12, 14, 19, 26, 27, 28, 29, 32, 33, 34, 35, 37 | CCACGCAT TCTCTAGA AGGACTCT CATGCAGC GGGGACGC AGTGCGCT TCGGTCCA |

TABLE 8 -continued

Primer probe design

| Assay | FO Name | FO Sequence RO Name | RO Sequence | Fi Name | Fi Sequence | Ri Name | Ri Sequence | Probe Name | Probe Sequence | Gene Subtypes Covered* | Amplicon |
|---|---|---|---|---|---|---|---|---|---|---|---|
| | | | | | | | | | | (one mismatch for 5, 2538) | GTAGAGCT CTTCTATC CTGGTGCT GCGGCATT CGACCGAC AATCTGGT TGTATACG TCCCGTCA GC (SEQ ID NO: 74) |
| Vim2b (2nd assay) | vim2b-FOb | CCACG CACTC TCTAG AAGGA C (SEQ ID NO: 8) | vim2b-ROb | GCAGA CGGGA CGTAC ACAAC (SEQ ID NO: 9) | vim2b-Fi | GTGCG CTTCG GTCCA G (SEQ ID NO: 30) | vim2b-Rib | TAAGT TGTCG GTCGA ATGC (SEQ ID NO: 32) | Vim2b-pd | CAGCA CCAGG ATAG (SEQ ID NO: 51) | VIM-2, 3, 6, 8, 9, 10, 11, 15, 16, 17, 18, 23, 24, 31, 36, 37, 38 | CCACGCAC TCTCTAGA AGGACTCT CATCGAGC GGGGACGC AGTGCGCT TCGGTCCA GTAGAGCT CTTCTATC CTGGTGCT GCGGCATT CGACCGAC AACTTAGT TGTGTACG TCCCGTCT GC (SEQ ID NO: 75) |
| Vim2b (3rd assay) | vim2b-FOb | CCACG CACTC TCTAG AAGGA C (SEQ ID NO: 8) | vim2b-RO | GCTGA CGGGA CGTAT ACAAC (SEQ ID NO:7) | vim2b-Fi | GTGCG CTTCG GTCCA G (SEQ ID NO: 30) | vim2b-Ri | CAGAT TGTCG GTCGA ATGC (SEQ ID NO: 31) | Vim2b-pe | CAGCA CCGGG ATAG (SEQ ID NO: 52) | VIM-5, 25, 38 | CCACGCAC TCTCTAGA AGGACTCT CATCGAGC GGGACGC AGTGCGCT TCGGTCCA GTAGAGCT CTTCTATC CCGGTGCT GCGGCATT CGACCGAC AATCTGGT TGTATACG TCCCGTCA GC |

TABLE 8 -continued

Primer probe design

| Assay | FO Name | FO Sequence | RO Name | RO Sequence | Fi Name | Fi Sequence | Ri Name | Ri Sequence | Probe Name | Probe Sequence | Gene Subtypes Covered* | Amplicon |
|---|---|---|---|---|---|---|---|---|---|---|---|---|
| Interal Amp Control | IAC60534-FO | GAACGGGATTGACTGTTTGA CA (SEQ ID NO: 10) | IAC60534-RO | AGCCTGCATCGACTTGTTCA (SEQ ID NO: 11) | IAC60534-Fi | GCTGGTGTTCGGTTCGGTAA (SEQ ID NO: 47) | IAC60534-Ri | CATCGGTACGGGGCGTTT (SEQ ID NO: 48) | IAC60534-p | CCACAGATTCTCCG (SEQ ID NO: 53) | | (SEQ ID NO: 76) GAACGGGATTGACTGTTTGACACTAGCTGGTGTTCGGTTCGGTAACGGAGAATCTGTGGGGCTATGTCACTAATACTTTCGAAACGCCCGTACCGATGCTGAACAAGTCGATGCAGGCT (SEQ ID NO: 65) |
| Oxa22c | OXA22c-FO | TGGTTGGGGATGGGATGTA (SEQ ID NO: 12) | OXA22c-RO | TTTCGAACAGAGCTAGGTATTCC (SEQ ID NO: 13) | OXA22c-Fi | ACCCACAAGTAGGCTGGTTA (SEQ ID NO: 33) | OXA22c-Ri | TTTCTAAGTTAAGGGAGAACGCTAC (SEQ ID NO: 34) | Oxa22c-p | TTGAGGCTGAACAA (SEQ ID NO: 54) | OXA-51, 64, 65, 66, 67, 68, 69, 70, 75(?), 76, 77, 78, 79(?), 8082, 83, 84, 86, 87, 88, 89, 90, 91, 92, 93, 94, 95, 98, 99, 100, 106, 107, 108, 109, 110 111, 1 | TGGTTGGGGATGGGATGTAGACCCACAAGTAGGCTGGTTAACTGGATGGGTTGTTCAGCCTCAAGGAAATATTGTAGCGTTCTCCCTTAACTTAGAAATGAAAAAAGAATACCTAGCTGTGTTCGAAA (SEQ ID NO: 72) |
| Oxa24a | OXA24a-FO | GCCGCGCAAATACAGAATAT (SEQ ID NO: | OXA24a-RO | ACCTTTTCTCGCCCTTCCAT | OXA24a-Fi | GTGCCAGCCTCTACATTT | OXA24a-Ri | TCATTAATATCCGTTTTCTG | Oxa24a-p | CCCTGATCGGATTG (SEQ ID | OXA-23, 49, 73, 146, 165, 167, 168, | GCCGCGCAAATACAGAATATGTGTCCAGCCTCT |

TABLE 8 -continued

Primer probe design

| Assay | FO Name | FO Sequence | RO Name | RO Sequence | Fi Name | Fi Sequence | Ri Name | Ri Sequence | Probe Name | Probe Sequence | Gene Subtypes Covered* | Amplicon |
|---|---|---|---|---|---|---|---|---|---|---|---|---|
| | | | | (SEQ ID NO: 14) | | (SEQ ID NO: 15) | | GTTC (SEQ ID NO: 36) | | NO: 55) | 169, 170, 171, 225, 239 (one mismatch for 27) | ACATTTAA AATGTTGA ATGCCCTG ATCGGATT GGAGAACC AGAAAAC GGATATTA ATGAAATA TTTAAATG GAAGGGC GAGAAAA GGT (SEQ ID NO: 70) |
| Oxa48(19) | Oxa48 (19)- FO | AGCAA AGGAA TGGCA AGAAA ACA (SEQ ID NO: 16) | Oxa48 (19)-RO | GCTTG GTTCG CCCGT TTAA (SEQ ID NO: 17) | Oxa48 (19)-Fi | AGTTG GAATG CTCAC TTTACT GA (SEQ ID NO: 37) | Oxa48 (19)-Ri | GGTAA ATCCT TGCTG CTTATT CTC (SEQ ID NO: 38) | Oxa48 (19)-pc | CTACG CCCTG TGATT (SEQ ID NO: 56) | OXA-48, 162, 163, 181, 199, 204, 232, 244, 245 and 247 | AGCAAAG GAATGGCA AGAAAAC AAAAGTTG GAATGCTC ACTTTACT GAACATAA GCGTAGTT GTGCTCTG GAAATGAG AATAAGCA GCAAGGAT TTACCAAT AATCTTAA ACGGGCGA ACCAAGC (SEQ ID NO: 71) |
| VANA-FJ866609 | VANA-FJ866609-FO | AAATA CGAGC CGTTA TACAT TGG (SEQ ID NO: 20) | VANA-FJ866609-RO | TTTATC CGGCG AGAGT ACAG (SEQ ID NO: 21) | VANA-FJ866609-Fi | AATTA CGAAA TCTGG TGTAT GGAAA ATGTG (SEQ ID NO: 41) | VANA-FJ866609-R | CTGAA TAGCA ATTGT CGTTTT CCCAT T (SEQ ID NO: 42) | VanAf-pc | CCGCG CAAGG TTTTTC (SEQ ID NO: 59) | | AAATACGA GCCGTTAT ACATTGGA ATTACGAA ATCTGGTG TATGGAAA ATGTGCGA AAAACCTT GCGCGAA TGGGAAAA ACGACAAT TGCTATTC |

TABLE 8 -continued

Primer probe design

| Assay | FO Name | FO Sequence | RO Name | RO Sequence | Fi Name | Fi Sequence | Ri Name | Ri Sequence | Probe Name | Probe Sequence | Gene Subtypes Covered* | Amplicon |
|---|---|---|---|---|---|---|---|---|---|---|---|---|
| | | | | | | | | | | | | AGCTGTAC TCTCGCCG GATAAA (SEQ ID NO: 73) |
| Imp2b (1st assay) | Imp2b-FOe | CC(Pu)G G(Pu)CA CACTC (C/A)AG ATAAC (SEQ ID NO: 18) | Imp2b-ROd | GCCA(A/ T)GCTT CTA(A/ T)ATTT GCGTC A(Py) (SEQ ID NO: 19) | Imp2b-Fic | GTAGT GGTTT GG(Py)T (Pu)CCT GAA (SEQ ID NO: 39) | Imp2b-Rie | CCGTA CGGTT TAA(Py) AAA(Pu) CAACC A (SEQ ID NO: 40) | Imp2b-p | CCGAA TAATA TTTTCC TT (SEQ ID NO: 57) | IMP-1, 3, 4, 6, 10, 25, 26, 30, 34, 38, 40, 42 | CCGGGACA CACTCCAG ATAACGTA GTGGTTTG GTTGCCTG AAAGGAA AATATTAT TCGGTGGT TGTTTTTA TTAAACCG TACGGTTT AGGCAATT TGGGTGAC GCAAATAT AGAAGCTT GGC (SEQ ID NO: 66) |
| Imp2b (2nd assay) | Imp2b-FOe | CC(Pu)G G(Pu)CA CACTC (C/A)AG ATAAC (SEQ ID NO: 18) | Imp2b-ROd | GCCA(A/ T)GCTT CTA(A/ T)ATTT GCGTC A(Py) (SEQ ID NO: 19) | Imp2b-Fic | GTAGT GGTTT GG(Py)T (Pu)CCT GAA (SEQ ID NO: 39) | Imp2b-Rie | CCGTA CGGTT TAA(Py) AAA(Pu) CAACC A (SEQ ID NO: 40) | Imp2b-pf | CCGAA TAAAA TTTTCT T (SEQ ID NO: 58) | IMP-2, 8, 13, 14, 16, 18, 19, 20, 24, 32, 33 | CCGGGGCA CACTCAAG ATAACGTA GTGGTTTG GTTACCTG AAAAGAA AATTTTAT TCGGTGGT TGTTTTTG GACGGTCT TGGTAATT TGGGTGAC GCAAATTT AGAAGCTT GGC (SEQ ID NO: 67) |
| Ctx-M-1c | ctx1c-FO | GCTGT GTTAA TCAAT | ctx1c-RO | CGTCA CGCTG TTGTT | ctx1c-Fi | (G/T) AGTCT(G/T)CC | ctx1c-Ri | GCAAA CGGCG GACGT | Ctx1c-p | CGGCA AGTTT TTGC | CTX-M-1, 3, 11, 12, 15, | GCTGTGTT AATCAATG CCACACCC |

TABLE 8 -continued

Primer probe design

| Assay | FO Name | FO Sequence | RO Name | RO Sequence | Fi Name | Fi Sequence | Ri Name | Ri Sequence | Probe Name | Probe Sequence | Gene Subtypes Covered* | Amplicon |
|---|---|---|---|---|---|---|---|---|---|---|---|---|
| | | GCCAC AC (SEQ ID NO: 22) | | AGGAA (SEQ ID NO: 23) | | TCCCG ACTG (SEQ ID NO: 43) | | A (SEQ ID NO: 44) | | (SEQ ID NO: 60) | 22, 23, 28, 32, 33, 36, 42, 52, 54, 55, 57, 58, 60, 61, 64, 69, 71, 72, 79, 82, 88, 96, 101, 103, 107, 108, 109, 114, 117, 123, 132, 133, | AGTCT(G/T) CCTCCCGA CTGCCGCT CTAATTCG GCAAGTTT TTGCTGTA CGTCCGCC GTTTTGCG CATACAGC GGCACACT TCCTAACA ACAGCGTG ACG (SEQ ID NO: 63) |
| Ctx-M-5a | Ctx5a-FO | GCGAC CTGGT TAACT ACAAT CC (SEQ ID NO: 24) | Ctx5a-RO | GCAAT CAGCT TATTC ATGGC AGTA (SEQ ID NO: 25) | Ctx5a-Fi | TTGCG GAGAA ACACG TTA (SEQ ID NO: 45) | Ctx5a-Ri | GCTAT ACTGC AGCGC C (SEQ ID NO: 46) | Ctx5a-p | CCAAG CTCAG CCA (SEQ ID NO: 61) | CTX-M-2, 5, 20, 31, 43, 44, 56, 59, 76, 77, 92, 95, 97, 131 | GCGACCTG GTTAACTA CAATCCCA TTGCGGAG AAACACGT TAACGGCA CGATGACG CTGGCTGA GCTTGGCG CAGCGCT GCAGTATA GCGACAAT ACTGCCAT GAATAAGC TGATTGC (SEQ ID NO: 64) |

TABLE 9

| | A | B |
|---|---|---|
| | gBlock Name | gBlock design |
| 1 | | |
| 2 | Kpc1a/ Oxa22c/ CtxM1c | GGAACCATTCGCTAAACTCGAACaggacttgtgcggctccatcggtgtgtacgcgatggataccggctcaggcgcaactgtaagttaccgcgtgaggacgc TTCCCACTGTGCAGCTCATTTGTTGGGGATGGATGTAGACCCACAGTAGGCTGTTAACTGGATGGGTTGT TCAGCCTGTAATCAATGCCACACccagtcgcctcccgatgcccgctcaattcggcaagtttgctgtactgccgttgcgcatacagcggcacacTTCC AGCTGTGTTAATCAATGCCACACccagtcgcctcccgatgcccgctcaattcggcaagtttgctgtactgccgttgcgcatacagcggcacacTTCC TAACAACAGCGTGACG (SEQ ID NO: 77) |
| 3 | Ndm1b(1)/ Oxa24a/ CtxM5a | GGATCAAGCAGGAGATCAACCtgcccggtcgcgctggcggtggtgactcacgcgcatcaggacaagatggcggtatggacgcgctgcatgcggcgggggattgc gacTTATGCCAATGCGTTGTCGACCGCCGCAAATACAGAATATgtgccgacccctacattaaaatgtgaatgccctgatcggatggagaaccca gaaaacggatattaatgaaatatttaaATGGAAGGGCGAAGAACCCAGGAGAAAAGGTGCGACTGGTTAACTACAATCcattgcggagaaaacgttaacg cacgatgacgcggctgagctggcgcagcggcgctgcagtatagcgacaaTACTGCCATGAATAAGCTGATTGC (SEQ ID NO: 78) |
| 4 | Ndm1c/ Oxa24a/ CtxM5a | CGGCCACCACCAGTGACAATAtcaccgttggatcgacggagaccacgacatcgchttggtcgctgcctgatcaaggacagcaaggccaagtcgctcggcaatctcgG TGATGCCGACACTGAGCAGCCGCCAAATACAGAATATgtgccgacccctacattaaaatgtgaatgccctgatcggatggagaaccagaaaa cggatattaatgaaatatttaaATGGAAGGGCGAAGAACCCAGAGAAAAGGTGCGACTGGTTAACTACAATCcattgcggagaaaacagttaacgcacgat gacgtggctgagctggcgcagcggcgctgcagtatagcgacaaTACTGCCATGAATAAGCTGATTGC (SEQ ID NO: 79) |
| 5 | Vim2b(1)/ Oxa48(19)/ Tem2c | CCACGCATTCTCTAGAAGGACTctcatcgagcgggacgcagtgcgcttcggtccagtccagtgccattcgacgcagacgacaatctgGTTG TATACGTCCCGTCAGCAGCAAGGAATGCCAAGAAAACAAaagagaatgtcacttactgaacataaatcacaggcgtagttgtgctctgga atgaataagcagcaaggattacccaatacttTAAACGGCCAAGCCACTGGGCCAGATGTAAgccctccccgctagttatctaca cgacggggagtcaggcaactatgatgaacgaatagaacagatcgctgagaTAGGTGCCTCACTGATTAAGCATT (SEQ ID NO: 80) |
| 6 | VanA-F/ Shv1a | AAATACGAGCCGTTATACATTGGaattacgaactctggtattgctatgagaaatgtgcgaaaaacgttgcgggcagtgcagtagtgctcgcgcagtgtcggagcacattaaagtagctctgcggcagtgcctgcggtgggcggccagtgcagtagtgcagattgatgcggtgacga acagctggagcgaaagtcccacTATCGCCAGCAGGATCTGG (SEQ ID NO: 81) |
| 7 | Imp2b(1)/ VanB1c(1) | CCCGGACACACTCCAGATAACGTAGTGTTGGTTGCTCGAAAGGAAAATATTATTCGTGTGTTTATTAA ACCTACGGTTAGGCATTTGGGTGACGCAATATAGAAGTTGGCTTACCTACCCTGTCTTGTGAAGCCG GCACGGTTCAGGTTCGTCCTTTGGCTTAACCAAAGTAACGGTTACGGAAGAACTTAACCTGCGATAGAAGCCG CAGGACAATATGATGGAAAAATCTTAATTGAGCAAGCGATTTCGG (SEQ ID NO: 82) |
| 8 | Ndm1b(2)/ Imp2b(2)/ VanB1c(2) | GGATCAAGCAGGAGATCAACCtgcccgtcgcgctggcggtgactcacgcgcatcaggacaagatgggcgTATGAACGCGCTGCATGCg gggattgcgacTTATGCCAATGCGTTGTCGACCGCCGCCCAATGCCGCACTCAAGATAACGTAGTGTTGGTTACCTGAAAG CCTTACCTACCCTGTCTTTGTGAAGCCGCCACGGTTCAGGTTCGTCCTTTGGCGTAACCAAAGTAAACAGTACGG AAGAACTAAACGCTGCGATAGAAGCAGCAATATGATGGAAAAATCTTAATTGAGCAAGCGATTTCGG (SEQ ID NO: 83) |
| 9 | Ndm1b(3)/ Imp2b(3) | GGATCAAGCAGGAGATCAACCtgcccgtcgcgctggcggtgactcacgcgcatcaggacaagatgggcgTATGGGCGCCGCTGCATGCg gcgggattgcgacTTATGCCAATGCGTTGTCGACCAGTGCACTCAAGATAACCTAGTGGTTTGGTTGCCTGAAAGT AAAATTTATTCGGTTGGTTGCTTATTAAACCTCACGGTCTTGGCCAATTTGAGCAAATTTAGAAGCTTGG C (SEQ ID NO: 84) |
| 10 | Vim2b(2)/ VanB1c(2) | CCACGCACTCTCTAGAAGGACTCTCATCGAGCGGGACGCAGTGCGCTTCGGTCCAGTAGAGCTCTTCTATCCT GGTGCTGCGCATTCGACCGACAACTTAGTGTGTACGTCCCGTCCTGCCTTACCTACCCTGTCTTTGTGAAGCCGG CACGGTCAGGTTCGTCCTTTGGCTAACCAAAGTAACCAGTACGGAAGAACTAAACGCTGCGATAGAAGCAGC AGGACAATATGATGGAAAAATCTTAATTGAGCAAGCGATTTCGG (SEQ ID NO: 85) |

TABLE 9 -continued

| | A | qBlock design B |
|---|---|---|
| 11 | Ndm1b(2)/ Imp2b(2) | GGATCAAGCAGGAGATCAACCTGCCGTCGCCTGGCGGTGACTCACGCCATCAGGACAGATGGGCGG TATGAACGGCTGCATGCGGCGGGATTGCGACTTATGCCAATGCGTTGTGACCGGGCACACTCAAGATAAC GTAGTGGTTTGGTTACCTGAAAAGAAAATTTATTCCGTGGTTGTTTTGTTAAACCGACGGTCTTGGTAATTTG GGTGACCGCAAATTTAGAAGCTTGGC (SEQ ID NO: 86) |
| 12 | Vim2b(3)/ IAC60529 | CCACGCACTCTCTAGAAGGACTTCATCGAGCGGGACGCAGTGCGCTTCGGTCGGTCCAGTAGAGCTCTTCTATCCC GGTGCTGCGCATTCGACCGACAATCTGGTTGTATACGTCCCGGATGAGTGTGACGGAGTGTAACTCGA TGAGTTACCCGCTAATCGAACTGGGCGAGAGATCTCCAGCGCTGACACTCGATCCCGAGGCCTGACCCGACAT ATCAGCTCAGACTAGAGCGG (SEQ ID NO: 87) |
| 13 | Oxa48_19_g | atgcAGCAAGGAATGGCAAGAAAACAaaagaggaatgctcacttactgaacataatcacagggctagttgtgctctggaatgagaataagcagcaaggat ttaccaataatcTTAAACGGGCGAACCAAGCatgc (SEQ ID NO: 88) |
| 14 | Kpc1a_1b_ 1c_g | CAACCTCGTCGCGGAACCATTGCTAAACTCGACAGGACTTTGGCGCTCCATGCGTGTACGCGATGGATA CCGGCTCAGGCGCAACTGTAAGTTACCCGCTCGAGGAGCGCCGCCGAGTGGCTCCGGCTTGGGACACCATCCGTTACGGCAAAA GCTCGCCCCTGTCGTGCTCCGCAGCGACCAGCCGGCTTGCTGGACAACAGGCATGGCGTGGCCGAGCTGTCCGCG AATGGCTGGTTCCGTGGTCACCCATCTCGGAAAAATATCTGACAACAGGCATGGCGTGGCCGAGCTGTCCGCG GCCCGCGTGCAATACAGTGATAACGCCGCCCAATTTGTTGCTGAAGGAGTTGGCGGCCCGGGCGAACCGGGCTGA CGGCCTTCATGCGCGATACCTTATCGGCGATACCACCGTTCCGTCTGGACCCGCGTCGGAGCTGGAGCTGAACTCCGCCATC CCAGGCGATGCGCCGCAGATACCTCATCCGCCCAGCGACCAGTTTGTTGATTGCTAAAGGGAAACACGACCGGCAACCCGATCCG CACTGGCTGCGCCCGCAGCTGGGCAGCTGGGCCAGTCGGAGACAAAACCGGAACCTGCGAGTGTATGGCACGGCAAGTA CTA (SEQ ID NO: 89) |
| 15 | Oxa-24a_g | ATAAAAAATTAATTTGTATGGAATGCTCTAAGCCCCGCGACAATACGAAATATGTGCCAGCCTCTACATTTAAA ATGTTGAATGCCCTGATCGGATTGGAGAACGCAAAACGGATATTAATGAAATATTTAAATGAAGGGGCGAGA AAAGGTCATTACCACTTGGGAAAAAGACATACACTAGGAGAAGCC (SEQ ID NO: 90) |
| 16 | Oxa-22c_g | CAATCCATGCTATTCATAGAAGCAAGAAATGGAAACAAAATATACGCAAAAAGTGGTTGGGATGGATGTAA ACCCACAGTAGCCTGGTTAACTGGCAAATGGGCTCGCGAATGGGGGGCAGATATTTTGTAGCGTTCTCCCCTTAACTTA GAAATGAAAAAGAATACCTAGCTCTGTTCGAAAAGAGAATTACTTATAAAAGCTTAGAACAATTAGCTATTTT ATAG (SEQ ID NO: 91) |
| 17 | VANA FJ866609_g | TAAAATCTGCAATAGAGATAGCCCGCTAACATTAATAAAGAAAATACCGCCTTATACATTGGAATTACGAA ATCTGGTATGAAAAATGCACGGATTTACTTGTCGCGAAATGGGAAAACGACAATTGCTATTCAGCTGCTACTCT CGCCGGATAAAAAATGCACGGATTTACTTGTTAAAAAGAACCATGAATATGAAAATCAACCATGTT (SEQ ID NO: 92) |
| 18 | VANB1c_g | GATAAAGGTGACAAGCCGGAGACGGGTGCGCTTACCTACCCTGTCTTTTGAAGCCGGCACCGTCAGGTTCGTC CTTTGGCTTAACCAAAGTTGAGCAAGCCGATTTCGGGCTGTGAGGTCGTGCGGTTATGGGGA (SEQ ID NO: 93) AAAATCTTAATTGAGCAAGCCGATTTCGGGCTGTGAGGTCGTGCGGTTATGGGGA |
| 19 | VANB1C-Rib-g | GAAAAAGGTGACAAGCCGGAGACGGAGACGCTTACCTACCCTGCTTTTTGTGAAGCCGGCACCGTCAGGTTCGT CCTTTGGCTAACCAAAGTAAACGTGCGAAGCCGATTTCGGGCTGTGAGGTCGTGCGGTCATGGGA (SEQ ID NO: 94) AAAAATCTTAATTGAGCAAGCCGATTTCGGGCTGTGAGGTCGTGCGGTCATGGGA |
| 20 | OXA22c | atgcTGTTGGGATGGATGTAraccacaagtaggctggttaactggatgggtgttcagctcaaggcctcaaggaatattgtaggcgttctccctaacttagaatgaaaaaa GGAATACCTAGCTCTGTTCGAAAatgc (SEQ ID NO: 95) |

TABLE 9 -continued

| | A | qBlock design |
|---|---|---|
| | | B |
| 21 | OXA24a | atgcGCCCGCAATACAGAATATgtgccagcctctacattaaaatgttgaatgcctgatcgcggattggagaaccagaaaacggattaatgaaatattaaATG GAAGGGCGAGAAAAGGTatgc (SEQ ID NO: 96) |
| 22 | VANA_FJ866609 | atgcAAATACGAGCCGTTATACATTGGaattacgaaatctggtgtatggaaaatgtcgaaaaaccttgcggaatgggaaacgacaattgctattcagCTG TACTCTCGCCGATAAAatgc (SEQ ID NO: 97) |
| 23 | VANB1c | atgcCTTACCTACCCTGTCTTTGTGAAgcggcacggtcaggttcgtccttggcgtaaccaaagtaaac ggtacggaagaacttaacgctgcgatagaagcggc aggacaatgatggaaaatctTAATTGAGCAAGCGATTTCGAatgc (SEQ ID NO: 98) |
| 24 | vim2b-a | atgcCTGCGCACTCTCTAAAAGCGCTCTCCTCTAGTGAGATGTGGTGCGCTTCGGTCCCGTAGAGGTTTCTATC CTGGTGCTGCGCATTCGGGCGACAATCTTGTGGTATACGTGCCGGCCGTatgc (SEQ ID NO: 99) |
| 25 | vim2b-b | atgcCCCACCACTCTCTAGAAGGACTTCATCGAGCGGGGACACGCGGTGCGCCTTCGCCTTCGGTCCAGTAGAACTCTTCTATC CTGGTGCTGCGCATTCGACCGACAACTTAGTTGTGTACGTCCCGTCTGCatgc (SEQ ID NO: 100) |
| 26 | ndm1b | atgcGGATCAAGCAGGAGATCAACCtgccggtcgcgtggcggtgactcacgcgcatcaggacaagatgggcggtatggacgcgctgcatgcggcggggg attgcgacTTATGCCAATGCGTTGTCGAatgc (SEQ ID NO: 101) |
| 27 | IAC | GATTGCCACGCATTGAGCTAgcgagtcagcgataagcatgacgcgctttcaagcgtcgcgagtatgtgaaccaaggctccggacagcgtcgacaggactatatacttggtTTG ATCTCGCCCGACAAGAACGGGATTGACTGTTTGACActagctggttcgttcgtcgtaacggaaatctgtggggctatgtcactaatactttcgaaa cgccccgtaccgatgcTGAACAAGTCGATGCAGCTGATGAGTGTACtgatgagttaccgctaatcgaactgggcgaga gatcccagcgctgatgcactccgatcccgaggcctgaccgacTATCAGCTCAGACTAGAGCGGCTGCGCATAAGCAACAattaacca ctgtgactcgttataacctggcagttaaagtcggagataggagccgcaatacacagttaccgcatctagacctaacTGAGATACTGCCATAGACGACT (SEQ ID NO: 1) |

Example 6: Testing Additional Genes—the "Resistome" Test

The methods of the present invention may include detecting MDRO-associated genes in combination with detecting a broad number of other genes that together make up the "resistome" of organisms, or the collection of antibiotic resistance in pathogenic and non-pathogenic bacteria, also referred to as The Resistome Test. See FIG. 5 and Table 1.

The Resistome Test can be used by a clinician to help determine which antibiotics should be used based on Resistome test result of the patient sample, either because of the presence of an individual resistance gene or a combination of resistance genes. This ability to stratify genotype is also very specific and reproducible. Organism Resistome profiles can also be matched with actual Antibiotic Susceptibility Test (AST) data. When patients with matching Resistome patterns are found their similarity or lack of similarity and antibiotic resistance can potentially be inferred from this information.

Exemplary primer and probe sequences useful in the methods of the invention for performing The Resistome Test include those listed below in Table 10. It is readily apparent to those skilled in the art that other primer and probe sequence may be utilized in practicing the claimed methods.

TABLE 10

| Assay Name | Forward Primer Sequence | Reverse Primer Sequence | Probe Sequence | Gene Subtypes Covered |
|---|---|---|---|---|
| ACC-1 | GATGAGCCAGTGCACGKSAATA (SEQ ID NO: 102) | GTCGCTGGAGGTGGTTTGAT (SEQ ID NO: 103) | TAAGTTCGTTACCCA (SEQ ID NO: 104) | ACC-1, 2, 4 |
| ACC-3 | TCGCTGATAAAGCATTAGCC (SEQ ID NO: 105) | TGCGTTCCGCATTCAG (SEQ ID NO: 106) | TTCCAGAACTGCGC (SEQ ID NO: 107) | ACC-3 |
| ACT-1 | CCATAACGACGCGGGTCT (SEQ ID NO: 108) | TGCGCCTCTTCCGYTTT (SEQ ID NO: 109) | TCCAGCTTGAGCGG (SEQ ID NO: 110) | ACT-1-4, 6, 10, 13 |
| ACT-5 | CGCTGGCGTCAAACTTC (SEQ ID NO: 111) | CTTAAGGACCCGCKTCGTCAT (SEQ ID NO: 112) | CTWTGAGCAGGCCA (SEQ ID NO: 113) | ACT-5, 7, 14-21, 23, 35 |
| BEL-1 | CCCATGTCCATGCACAGACT (SEQ ID NO: 114) | GCTGCCCCTTGGATTTATATGTCAAC (SEQ ID NO: 115) | TCTCCAAAAATCAGCT (SEQ ID NO: 116) | BEL-1, 2, 3 |
| BES-1 | GGTGAGGCTCTATCCTATCCAGAC (SEQ ID NO: 117) | GCGTCCAGGCGCTGAA (SEQ ID NO: 118) | TCTCCCAACCCCTG (SEQ ID NO: 119) | BES-1 |
| CFE-1 | GTTACTGGCGTATTGGCGATATGT (SEQ ID NO: 120) | GGCTTTCACCGGCCAGTT (SEQ ID NO: 121) | CCCAGCCCAGACCC (SEQ ID NO: 122) | CFE-1 |
| CFE-1 | GTTACTGGCGTATTGGCGATATGT (SEQ ID NO: 120) | GGCTTTCACCGGCCAGTT (SEQ ID NO: 121) | TCCCAGCCCAGACC (SEQ ID NO: 123) | CFE-1 |
| CFE-1 | GTTACTGGCGTATTGGCGATATGT (SEQ ID NO: 120) | GGCTTTCACCGGCCAGTT (SEQ ID NO: 121) | TCTCCCAGCCCAGA (SEQ ID NO: 124) | CFE-1 |
| CFE-1 | GTTACTGGCGTATTGGCGATATGT (SEQ ID NO: 120) | GGCTTTCACCGGCCAGTT (SEQ ID NO: 121) | TCTCCCAGCCCAGAC (SEQ ID NO: 125) | CFE-1 |
| CMY-1 | GAGGAGGTGGATTCATCCGAGAAG (SEQ ID NO: 126) | GATGGGAGCCCGGCGAATA (SEQ ID NO: 127) | CCTACTACCGGCCA (SEQ ID NO: 128) | CMY-1, 8, 9, 10, 11, 19 |
| CMY-1 | GAGGAGGTGGATTCATCCGAGAAG (SEQ ID NO: 126) | GATGGGAGCCCGGCGAATA (SEQ ID NO: 127) | CCTACTACCGCCAG (SEQ ID NO: 129) | CMY-1, 8, 9, 10, 11, 19 |
| CMY-1 | GAGGAGGTGGATTCATCCGAGAAG (SEQ ID NO: 126) | GATGGGAGCCCGGCGAATA (SEQ ID NO: 127) | CCTACTACCGCCAGT (SEQ ID NO: 130) | CMY-1, 8, 9, 10, 11, 19 |
| CMY-1 | GAGGAGGTGGATTCATCCGAGA | GATGGGAGCCCGGCGAATA | CCTACTACCGCCAGTG | CMY-1, 8, 9, 10, 11, 19 |

TABLE 10-continued

| Assay Name | Forward Primer Sequence | Reverse Primer Sequence | Probe Sequence | Gene Subtypes Covered |
|---|---|---|---|---|
| CMY-1 | AG (SEQ ID NO: 126) | (SEQ ID NO: 127) | (SEQ ID NO: 131) | |
| CMY-1 | GAGGAGTGGATTCATCCGAGA AG (SEQ ID NO: 126) | GATGGGAGCCCGGCGAATA (SEQ ID NO: 127) | CTACTACCGCCAGTG (SEQ ID NO: 132) | CMY-1, 8, 9, 10, 11, 19 |
| CMY-1 | GAGGAGTGGATTCATCCGAGA AG (SEQ ID NO: 126) | GATGGGAGCCCGGCGAATA (SEQ ID NO: 127) | TACTACCGCCAGTG (SEQ ID NO: 133) | CMY-1, 8, 9, 10, 11, 19 |
| CMY-2 | GATATGGCCCGCTGGRTWC (SEQ ID NO: 134) | CGCAATGCCCTGYTGGA (SEQ ID NO: 135) | CCRCGTTCAGGAG (SEQ ID NO: 136) | CMY-2, 4, 5, 6, 7, 12-18, 20-40, 42-46, 49, 53-64, 69, 71, 73, 77, 80, 94, 95, 99, 102, 108, 111 |
| CMY-2 | GATATGGCCCGCTGGRTWC (SEQ ID NO: 134) | CGCAATGCCCTGYTGGA (SEQ ID NO: 135) | CCRCGTTCAGGAGA (SEQ ID NO: 137) | CMY-2, 4, 5, 6, 7, 12-18, 20-40, 42-46, 49, 53-64, 69, 71, 73, 77, 80, 94, 95, 99, 102, 108, 111 |
| CMY-2 | GATATGGCCCGCTGGRTWC (SEQ ID NO: 134) | CGCAATGCCCTGYTGGA (SEQ ID NO: 135) | CCRCGTTCAGGAGAA (SEQ ID NO: 138) | CMY-2, 4, 5, 6, 7, 12-18, 20-40, 42-46, 49, 53-64, 69, 71, 73, 77, 80, 94, 95, 99, 102, 108, 111 |
| CMY-2 | GATATGGCCCGCTGGRTWC (SEQ ID NO: 134) | CGCAATGCCCTGYTGGA (SEQ ID NO: 135) | CCAGCCRCGTTCAG (SEQ ID NO: 139) | CMY-2, 4, 5, 6, 7, 12-18, 20-40, 42-46, 49, 53-64, 69, 71, 73, 77, 80, 94, 95, 99, 102, 108, 111 |
| CMY-2 | GATATGGCCCGCTGGRTWC (SEQ ID NO: 134) | CGCAATGCCCTGYTGGA (SEQ ID NO: 135) | TCCATGTTGGCCT (SEQ ID NO: 140) | CMY-2, 4, 5, 6, 7, 12-18, 20-40, 42-46, 49, 53-64, 69, 71, 73, 77, 80, 94, 95, 99, 102, 108, 111 |
| CMY-2 | GATATGGCCCGCTGGRTWC (SEQ ID NO: 134) | CGCAATGCCCTGYTGGA (SEQ ID NO: 135) | TTCAGGAGAAAAACGC (SEQ ID NO: 141) | CMY-2, 4, 5, 6, 7, 12-18, 20-40, 42-46, 49, 53-64, 69, 71, 73, 77, 80, 94, 95, 99, 102, 108, 111 |
| CMY-41 | CTGGGTCTGTTTAGTGCAAA (SEQ ID NO: 142) | GTCTGTTACCTGTACTTAATG ACTCC (SEQ ID NO: 143) | CCCCGCCATACGA (SEQ ID NO: 144) | CMY-41, 47, 48, 50, 51, 65-68, 72, 75, 76, 78, 79, 81, 84, 87, 90, 103, 110 |
| CMY-70 | GGGCTCCACTGCGGATT (SEQ ID NO: 145) | GCCAGCATCACGATGCCAAG (SEQ ID NO: 146) | CTACGTTGCTTTCGT (SEQ ID NO: 147) | CMY-70, 74, 83, 93, 100, 101 |
| CTX-M-1 | AGTCTKCCTCCCGACTG (SEQ ID NO: 148) | GCAAACGCGCGGACGTA (SEQ ID NO: 44) | CGGCAAGTTTTTGC (SEQ ID NO: 60) | CTX-M-1, 3, 11, 12, 15, 22, 23, 28, 32, 33, 36, 42, 52, 54, 55, 57, 58, 60, 61, |

TABLE 10-continued

| Assay Name | Forward Primer Sequence | Reverse Primer Sequence | Probe Sequence | Gene Subtypes Covered |
|---|---|---|---|---|
| CTX-M-2 | TTGCGGAGAAACACGTTA (SEQ ID NO: 45) | GCTATACTGCAGCGCC (SEQ ID NO: 46) | CCAAGCTCAGCCA (SEQ ID NO: 61) | 64, 69, 71, 72, 79, 82, 88, 96, 101, 103, 107, 108, 109, 114, 117, 123, 132, 133, 136 |
| CTX-M-8/25 | CGGYGCTGCCAGCATT (SEQ ID NO: 149) | CRCCGCTGCCGGTTTTAT (SEQ ID NO: 150) | CTACCCACATCGTG (SEQ ID NO: 151) | CTX-M-2, 5, 20, 31, 43, 44, 56, 59, 76, 77, 92, 95, 97, 131 |
| CTX-M-9 | TCATGCTGGGCGAAA (SEQ ID NO: 152) | GCTGCGCCGGTCGTAT (SEQ ID NO: 153) | CACCACTGCGCC (SEQ ID NO: 154) | CTX-8, 25, 26, 39, 40, 41, 63, 78, 89, 91, 94, 100 |
| | | | | CTX-9, 13, 14, 16, 17, 18, 19, 21, 24, 27, 38, 46, 47, 48, 49, 50, 51, 65, 67, 81, 82, 83, 84, 85, 86, 90, 93, 98, 99, 104, 106, 110, 111, 112, 113, 121, 122, 123, 125, 126, 129, 130, 134 & 147 |
| DHA-1 | TGGCCCGAGCAGAAAGATATG (SEQ ID NO: 155) | TGGTTGTCTGTTACCGGRTGC (SEQ ID NO: 156) | CCAACGAGGTCGCA (SEQ ID NO: 157) | DHA-1, 2, 3, 5, 6, 7 |
| FOX-1 | AGAGGATCGCCATCGTCAT (SEQ ID NO: 158) | GCTGAGCCGCCTTCA (SEQ ID NO: 159) | TCCCATCGAGGCCA (SEQ ID NO: 160) | FOX-1-10 |
| GES-1 | CCTATTGCTATGGCACGTACTG (SEQ ID NO: 161) | TGGTGTGGGTCGARGTG (SEQ ID NO: 162) | CCGCCATAGAGA (SEQ ID NO: 163) | GES-1-17 |
| GES-1 | CCTATTGCTATGGCACGTACTG (SEQ ID NO: 161) | TGGTGTGGGTCGARGTG (SEQ ID NO: 162) | CCGCCATAGAGGAC (SEQ ID NO: 164) | GES-1-17 |
| GES-1 | CCTATTGCTATGGCACGTACTG (SEQ ID NO: 161) | TGGTGTGGGTCGARGTG (SEQ ID NO: 162) | TCAGTGCGCCCC (SEQ ID NO: 165) | GES-1-17 |
| GES-1 | CCTATTGCTATGGCACGTACTG (SEQ ID NO: 161) | TGGTGTGGGTCGARGTG (SEQ ID NO: 162) | TCAGTGCGCGCCCA (SEQ ID NO: 166) | GES-1-17 |
| GES-1 | CCTATTGCTATGGCACGTACTG (SEQ ID NO: 161) | TGGTGTGGGTCGARGTG (SEQ ID NO: 162) | TCCTTCTATGGCGG (SEQ ID NO: 167) | GES-1-17 |
| GES-1 | CCTATTGCTATGGCACGTACTG (SEQ ID NO: 161) | TGGTGTGGGTCGARGTG (SEQ ID NO: 162) | TCCTTCTATGGCGGC (SEQ ID NO: 168) | GES-1-17 |
| GES-1 | CCTATTGCTATGGCACGTACTG (SEQ ID NO: 161) | TGGTGTGGGTCGARGTG (SEQ ID NO: 162) | TCCTCTATGGCGGCG (SEQ ID NO: 169) | GES-1-17 |
| GIM-1 | GAAGACACGAAGTTGTTATTATCCTG (SEQ ID NO: 170) | AGAATGAGTTGAGATGCTAGCC (SEQ ID NO: 171) | CCTGGTATCCCCTG (SEQ ID NO: 172) | GIM-1 |

TABLE 10-continued

| Assay Name | Forward Primer Sequence | Reverse Primer Sequence | Probe Sequence | Gene Subtypes Covered |
|---|---|---|---|---|
| IAC-R | GGGGACTAACATAGGCGTAAA (SEQ ID NO: 173) | GTTGAGATGAGTACGTTATTCAGG (SEQ ID NO: 174) | TCGCAGCTCGTGCG (SEQ ID NO: 175) | |
| IMI-1 | CAACTMAATCTTAATCAGATCGT GAA (SEQ ID NO: 176) | GCCATATCACCTAATGACATT CCA (SEQ ID NO: 177) | TTCACCCATCACAAC (SEQ ID NO: 178) | IMI-1, 2, 3, 4, 7 |
| IMI-1 | CAACTMAATCTTAATCAGATCGT GAA (SEQ ID NO: 176) | GCCATATCACCTAATGACATT CCA (SEQ ID NO: 177) | TTCACCCATCACAACT (SEQ ID NO: 179) | IMI-1, 2, 3, 4, 7 |
| IMI-1 | CAACTMAATCTTAATCAGATCGT GAA (SEQ ID NO: 176) | GCCATATCACCTAATGACATT CCA (SEQ ID NO: 177) | TTCCATTCACCCATC (SEQ ID NO: 180) | IMI-1, 2, 3, 4, 7 |
| IMI-1 | CAACTMAATCTTAATCAGATCGT GAA (SEQ ID NO: 176) | GCCATATCACCTAATGACATT CCA (SEQ ID NO: 177) | TTTAGTTGTGATGGGT G (SEQ ID NO: 181) | IMI-1, 2, 3, 4, 7 |
| IMP-1 | GTAGTGGTTTGGYTRCCTGAA (SEQ ID NO: 182) | CCGTACGGTTTAAYAAARCAA CCA (SEQ ID NO: 183) | CCGAATAATATTTTCC TT (SEQ ID NO: 57) | IMP-1, 3, 4, 6, 10, 25, 26, 30, 34, 38, 40, 42 |
| IMP-2 | GTAGTGGTTTGGYTRCCTGAA (SEQ ID NO: 182) | CCGTACGGTTTAAYAAARCAA CCA (SEQ ID NO: 183) | CCGAATAAAATTTTCT T (SEQ ID NO: 58) | IMP-2, 8, 14, 16, 18, 19, 20, 24, 32, 33 |
| IMP-5 | ACACGGCTTGGTGGTTCTT (SEQ ID NO: 184) | TCAGTATCTTTAGCCGTAAAT GGAGT (SEQ ID NO: 185) | CTGAGGCCTATCTGA (SEQ ID NO: 186) | IMP-5 |
| KPC-1 | AGGACTTTGGCGGCTCCAT (SEQ ID NO: 26) | CTCAGCGCGGTAACTTACAGT TG (SEQ ID NO: 27) | TATCCATCGCGTACAC (SEQ ID NO: 49) | KPC-1 thru KPC-16 |
| MR-1 | ATGAACGCGCAGGCCATT (SEQ ID NO: 187) | CGAAGGTAAAGTAGTGTGGCT GAC (SEQ ID NO: 188) | CCGGCACCGCCAT (SEQ ID NO: 189) | MIR-1-6 |
| MOX-1 | CTGACCGCGACCCTRGGR (SEQ ID NO: 190) | GCTCGCCTTGTCATCCAGYT (SEQ ID NO: 191) | CTCCCTTGACCACC (SEQ ID NO: 192) | MOX-1-4, 8 |
| MOX-5 | GTCACTCCCGSCATGCT (SEQ ID NO: 193) | CAGATCCGCCGARCTGGT (SEQ ID NO: 194) | CYTACGGCATCAAGA (SEQ ID NO: 195) | MOX-5, 6, 7 |
| NDM-1 | GATCGACGGCACCGACAT (SEQ ID NO: 28) | CGAGATTGCCGAGCGACTT (SEQ ID NO: 29) | TCAAGGACAGCAAG (SEQ ID NO: 50) | NDM-1 thru 9 |
| NMC-A | ATTTTAGACTCGATCGTTGGGAG T (SEQ ID NO: 196) | TGCTGCAGGTGTAGATGTGT (SEQ ID NO: 197) | TTTCCAGGCGATGAGC (SEQ ID NO: 198) | NMC-A |

TABLE 10-continued

| Assay Name | Forward Primer Sequence | Reverse Primer Sequence | Probe Sequence | Gene Subtypes Covered |
|---|---|---|---|---|
| OXA-10 | ATCCTGGTGTCGCATGG (SEQ ID NO: 199) | TTCGTTGTCTATATCCATGTTA AAGG (SEQ ID NO: 200) | CCTCTGTCTCCTTCT (SEQ ID NO: 201) | OXA-10, 14, 16, 17 |
| OXA-10 | ATCCTGGTGTCGCATGG (SEQ ID NO: 199) | TTCGTTGTCTATATCCATGTTA AAGG (SEQ ID NO: 200) | CTCAACCCACCCAA (SEQ ID NO: 202) | OXA-10, 14, 16, 17 |
| OXA-10 | ATCCTGGTGTCGCATGG (SEQ ID NO: 199) | TTCGTTGTCTATATCCATGTTA AAGG (SEQ ID NO: 200) | CTCAACCCACCCAAC (SEQ ID NO: 203) | OXA-10, 14, 16, 17 |
| OXA-10 | ATCCTGGTGTCGCATGG (SEQ ID NO: 199) | TTCGTTGTCTATATCCATGTTA AAGG (SEQ ID NO: 200) | TCTCCTTCTCAACCC (SEQ ID NO: 204) | OXA-10, 14, 16, 17 |
| OXA-18 | GCCGACCGATCCGACCAT (SEQ ID NO: 205) | GCGTCAGCTCCTGCGAATAC (SEQ ID NO: 206) | CTGAAGGATTCCATCG (SEQ ID NO: 207) | OXA-18 |
| OXA-2 | GGCACGATAGTTGTGGCAGAC (SEQ ID NO: 208) | CGTTTCTTCGATCGCACAGGA T (SEQ ID NO: 209) | TCCGCTTGGCTTC (SEQ ID NO: 210) | OXA-2, 15, 32 |
| OXA-23 | GTGCCAGCCCTCTACATTT (SEQ ID NO: 35) | TCATTAATATCCGTTTTCTGGT TC (SEQ ID NO: 36) | CCCTGATCGGATTG (SEQ ID NO: 55) | OXA-23, 49, 73, 146, 165, 167, 168, 169, 170, 171, 225, 239 |
| OXA-24 | TTAGGTGAGGCAATGGCA (SEQ ID NO: 211) | TCTAGGGCCAGTCCGTCT (SEQ ID NO: 212) | TCAGCAGTTCCAG (SEQ ID NO: 213) | OXA-24, 25, 26, 40, 72, 139, 160, 207 |
| OXA-45 | GCAAGGTGCCTGTGACAA (SEQ ID NO: 214) | CCAGCATCGTAGCCCATGAC (SEQ ID NO: 215) | CCTTCGCGCCAATG (SEQ ID NO: 216) | OXA-45 |
| OXA-48 | AGTTGGAATGCTCACTTTACTGA (SEQ ID NO: 37) | GGTAAATCCTTGCTGCTTATTC TC (SEQ ID NO: 38) | CTACGCCCTGTGATT (SEQ ID NO: 56) | OXA-48, 162, 163, 181, 199, 204, 232, 244, 245 and 247 |
| OXA-50 | GCGGAAACCCGCTTCGTT (SEQ ID NO: 217) | CCCCTGTGATAAGCCGATCA (SEQ ID NO: 218) | CCCGCTTCCACCTA (SEQ ID NO: 219) | OXA-50 |
| OXA-51 | ACCCACAAGTAGGCTGTTA (SEQ ID NO: 33) | TTTCTAAGTTAAGGGAGAACG CTAC (SEQ ID NO: 34) | TTGAGGCTGAACAA (SEQ ID NO: 54) | OXA-51, 64, 65, 66, 67, 68, 69, 70, 76, 77, 78, 80, 82, 83, 84, 86, 87, 88, 89, 90, 91, 92, 93, 94, 95, 98, 99, 100, 106, 107, 108, 109, 110, 111, 113, 115, 120, 128, 130, 132, 138, 144, 148, 149, 150, 174, 175, 176, 177, 178, 179, 180, 194, 195, 196, 197, |

TABLE 10-continued

| Assay Name | Forward Primer Sequence | Reverse Primer Sequence | Probe Sequence | Gene Subtypes Covered |
|---|---|---|---|---|
| OXA-54 | AGAATTGAGCCTCAGATCGGTTG (SEQ ID NO: 220) | TCATCGCGAAGAACCACACAT (SEQ ID NO: 221) | TCGAGTTCAACCCAA (SEQ ID NO: 222) | 201, 202, 206, 208, 216, 217, 219, 223, 242, 248, 249, 254 |
| OXA-55 | CAGCATTTCAACAAGTGGATTTTCTAAGG (SEQ ID NO: 223) | GCTGCGCTCGGACACA (SEQ ID NO: 224) | CTTGTTGTCATGCAGT (SEQ ID NO: 225) | OXA-54 |
| OXA-58 | GGCTTTGTAGAGTGCCTCA (SEQ ID NO: 226) | CTTGGCGTTATTGCTAAAGCT (SEQ ID NO: 227) | CATGACTCAAATCGC (SEQ ID NO: 228) | OXA-55 |
| OXA-60 | GAACAGCCTGATCGCCTTCG (SEQ ID NO: 229) | CCGTAGGGCAGCACTTCCT (SEQ ID NO: 230) | TCGCGCACGGCCC (SEQ ID NO: 231) | OXA-58 & 97 |
| OXA-62 | ATCGGGCGCCCGGTACGCGCAG (SEQ ID NO: 232) | CGCCGCCAATGGTGCGGTTGCCATA (SEQ ID NO: 233) | CCCGACCTCGTTCA (SEQ ID NO: 234) | OXA-60 |
| OXA-62 | ATCGGGCGCCCGGTACGCGCAG (SEQ ID NO: 232) | CGCCGCCAATGGTGCGGTTGCCATA (SEQ ID NO: 233) | CCTCGTTCAGCTTCG (SEQ ID NO: 235) | OXA-62 |
| OXA-62 | ATCGGGCGCCCGGTACGCGCAG (SEQ ID NO: 232) | CGCCGCCAATGGTGCGGTTGCCATA (SEQ ID NO: 233) | CTCGTTCAGCTTCGC (SEQ ID NO: 236) | OXA-62 |
| PER-1 | GGTTGATCAGGGAAAGTTGGA (SEQ ID NO: 237) | TTATCGGAGCCCAGGTATTCTGGCT (SEQ ID NO: 238) | CCGTTATCGTAAACAGGGCT (SEQ ID NO: 239) | OXA-62 |
| SFC-1 | TGCAAACTGGGTGGTTGGA (SEQ ID NO: 240) | AGGCCAGATCACTGCATAATCG (SEQ ID NO: 241) | CCACAAGTACCCGTT (SEQ ID NO: 242) | PER-1, 3, 4, 5, 7, 8 |
| SHV-G2385/E240 | CCGGCGGGCTGCTGTTTAT (SEQ ID NO: 243) | CTGCTTTGTTATTCGGGCCAA (SEQ ID NO: 244) | TCGCTAGCTCCGG (SEQ ID NO: 245) | SFC-1 |
| SHV-G156 (WT) | GGCCCCGCCAGGATTGA (SEQ ID NO: 246) | GGTCAAGGCGGGTGAC (SEQ ID NO: 247) | CCAGATCGGCGACA (SEQ ID NO: 248) | SHV-2, 2A, 3, 20, 21, 30, 34, 39, 106, 141, 152, 153, 162, 163 |
| | | | | SHV-1, 6, 8, 11, 14, 16, 17, 19, 24-28, 32, 33, 35-39, 40-44, 47-54, 56-63, 65, 67-85, 87-89, 92-96, 98-101, 103-104, 107-114, 116-119, 121, 122, 125, 127, 130-133, 135-140, 142-151, 155-159, 161, 164, 166-182, 184-188, 190 |

TABLE 10-continued

| Assay Name | Forward Primer Sequence | Reverse Primer Sequence | Probe Sequence | Gene Subtypes Covered |
|---|---|---|---|---|
| SHV-G156 (WT) | GGCCCCGCAGGATTGA (SEQ ID NO: 246) | GGTCAAGGCGGGTGAC (SEQ ID NO: 247) | TCGCCGATCTGGCG (SEQ ID NO: 249) | SHV-1, 6, 8, 11, 14, 16, 17, 19, 24-28, 32, 33, 35-39, 40-44, 47-54, 56-63, 65, 67-85, 87-89, 92-96, 98-101, 103-104, 107-114, 116-119, 121, 122, 125, 127, 130-133, 135-140, 142-151, 155-159, 161, 164, 166-182, 184-188, 190 |
| SHV-G156 (WT) | GGCCCCGCAGGATTGA (SEQ ID NO: 246) | GGTCAAGGCGGGTGAC (SEQ ID NO: 247) | TCGCCGATCTGGCGC (SEQ ID NO: 250) | SHV-1, 6, 8, 11, 14, 16, 17, 19, 24-28, 32, 33, 35-39, 40-44, 47-54, 56-63, 65, 67-85, 87-89, 92-96, 98-101, 103-104, 107-114, 116-119, 121, 122, 125, 127, 130-133, 135-140, 142-151, 155-159, 161, 164, 166-182, 184-188, 190 |
| SHV-G156 (WT) | GGCCCCGCAGGATTGA (SEQ ID NO: 246) | GGTCAAGGCGGGTGAC (SEQ ID NO: 247) | TTGTCGCCGATCTGG (SEQ ID NO: 251) | SHV-1, 6, 8, 11, 14, 16, 17, 19, 24-28, 32, 33, 35-39, 40-44, 47-54, 56-63, 65, 67-85, 87-89, 92-96, 98-101, 103-104, 107-114, 116-119, 121, 122, 125, 127, 130-133, 135-140, 142-151, 155-159, 161, 164, 166-182, 184-188, 190 |
| SHV-G156D | GGCCCCGCAGGATTGA (SEQ ID NO: 246) | GGTCAAGGCGGGTGAC (SEQ ID NO: 247) | CCAGATCGACGACA (SEQ ID NO: 252) | SHV-27, -32, -45, -93, -105, -110, and -177 |
| SHV-G156D | GGCCCCGCAGGATTGA (SEQ ID NO: 246) | GGTCAAGGCGGGTGAC (SEQ ID NO: 247) | TCGTCGATCTGGCG (SEQ ID NO: 253) | SHV-27, -32, -45, -93, -105, -110, and -177 |
| SHV-G156D | GGCCCCGCAGGATTGA (SEQ ID NO: 246) | GGTCAAGGCGGGTGAC (SEQ ID NO: 247) | TCGTCGATCTGGCG (SEQ ID NO: 253) | SHV-27, -32, -45, -93, -105, -110, and -177 |
| SHV-G156D | GGCCCCGCAGGATTGA (SEQ ID NO: 246) | GGTCAAGGCGGGTGAC (SEQ ID NO: 247) | TTGTCGTCGATCTGG (SEQ ID NO: 254) | SHV-27, -32, -45, -93, -105, -110, and -177 |
| SHV-G238/E240 (WT) | CCGGCGGGCTGGTTTAT G (SEQ ID NO: 243) | CTGCTTTGTTATTCGGGCCAA (SEQ ID NO: 244) | TCGCCAGCTCCGG (SEQ ID NO: 255) | SHV-1, 6, 8, 11, 14, 16, 17, 19, 24-28, 32, 33, 35-39, 40-44, 47-54, 56-63, 65, 67-85, 87-89, 92-96, 98-101, 103-104, 107-114, 116-119, 121, 122, 125, 127, 130-133, 135-140, 142-151, 155-159, 161, 164, 166-182, 184-188, 190 |

TABLE 10-continued

| Assay Name | Forward Primer Sequence | Reverse Primer Sequence | Probe Sequence | Gene Subtypes Covered |
|---|---|---|---|---|
| SHV-G238/E240K | CCGGCGGGCTGGTTTAT (SEQ ID NO: 243) | CTGCTTTGTTATTCGGGCCAA G (SEQ ID NO: 244) | TTGCCAGCTCCGG (SEQ ID NO: 256) | SHV-31, 91, 97, 115, 120, 126 |
| SHV-G238S/ E240K | CCGGCGGGCTGGTTTAT (SEQ ID NO: 243) | CTGCTTTGTTATTCGGGCCAA G (SEQ ID NO: 244) | TTGCTAGCTCCGG (SEQ ID NO: 257) | SHV-4, 5, 7, 9, 10, 12, 15, 22, 23, 445, 46, 55, 64, 66, 90, 105, 123, 124, 128, 129, 134, 154, 160, 165, 183 |
| SIM-1 | GGCCTTGGCAATCTAAGTGA (SEQ ID NO: 258) | TGCGTCTCCGATTTCACTG (SEQ ID NO: 259) | CCTGGCCAAGCTTC (SEQ ID NO: 260) | SIM-1 |
| SME-1 | CGATTTCTTGGCGGTCCT (SEQ ID NO: 261) | CCTAAACTCATTATCTCCAAT AGAACG (SEQ ID NO: 262) | TTTAGTCATCCCCTCA (SEQ ID NO: 263) | SME-1-5 |
| SPM-1 | CATCCTGTTCCAGCGGATAATG (SEQ ID NO: 264) | ACCTCAACCAGCTCATTAGAA AAC (SEQ ID NO: 265) | CCTTGCCTTGTTTCA (SEQ ID NO: 266) | SPM-1 |
| TEM-E104 (WT) | TGCCATCCGTAAGATGCTT (SEQ ID NO: 267) | CCGGGCAAGAGCAACT (SEQ ID NO: 268) | CTTGGTTGAGTACTCA C (SEQ ID NO: 269) | TEM-1, 2, 5, 7, 10, 11, 12, 19, 20, 25, 27-42, 44, 45, 47-49, 51, 53-55, 57-59, 61, 62, 65, 67, 68-86, 90, 91, 93, 95-105, 108, 110, 112, 114-120, 122, 125-128, 132, 135-137, 140, 141, 143-148, 150-152, 154-160, 162-166, 168-176, 178-183, 185-195, 198, 200-204, 206-210, 212-222 |
| TEM-E104K | TGCCATCCGTAAGATGCTT (SEQ ID NO: 267) | CCGGGCAAGAGCAACT (SEQ ID NO: 268) | CTTGGTTAAGTACTCA C (SEQ ID NO: 270) | TEM-3, 4, 6, 8, 9, 15-18, 21, 22, 24, 26, 43, 46, 50, 52, 56, 60, 63, 66, 87-89, 92, 94, 106, 107, 109, 111, 113, 121, 123, 124, 129-131, 133, 134, 138, 139, 142, 149, 153, 161, 167, 177, 184, 197, 199, 205, 211 |
| TEM-G238/E240 (WT) | CCATCTGGCCCCAGT (SEQ ID NO: 271) | CGGCTGGCTGGTTTATT (SEQ ID NO: 272) | CTCACCGGCTCCAGA (SEQ ID NO: 273) | TEM-1, 2, 6, 7, 9, 11-13, 16-18, 26, 29-41, 43-45, 51, 53-60, 62-65, 67, 69, 70, 73-84, 87, 90, 95-100, 102-106, 108-110, 115-119, 122, 124-131, 133, |

TABLE 10-continued

| Assay Name | Forward Primer Sequence | Reverse Primer Sequence | Probe Sequence | Gene Subtypes Covered |
|---|---|---|---|---|
| TEM-G238/E240K | CCATCTGGCCCCAGT (SEQ ID NO: 271) | CGGCTGGCTGGTTTATT (SEQ ID NO: 272) | CTTACCGGCTCCAGA (SEQ ID NO: 274) | 140, 141, 143, 145-148, 150, 151, 153, 154, 156-166, 168-176, 179-187, 190, 192-196, 198, 200-206, 208-210, 212-222 |
| TEM-G238/E240 | CCATCTGGCCCCAGT (SEQ ID NO: 271) | CGGCTGGCTGGTTTATT (SEQ ID NO: 272) | CTCACTGGCTCCAGA (SEQ ID NO: 275) | TEM-3, 4, 8, 15, 19-22, 25, 50, 52, 66, 88, 89, 92, 94, 61, 85, 86, 91, 114, 121, 107, 112, 113, 120, 123, 132, 136, 144, 152, 155, 134, 138, 139, 167, 197, 177, 189, 191, 199, 211 |
| TEM-G238S/E240K | CCATCTGGCCCCAGT (SEQ ID NO: 271) | CGGCTGGCTGGTTTATT (SEQ ID NO: 272) | CTTACTGGCTCCAGA (SEQ ID NO: 276) | TEM-42, 47-49, 68, 71, 72, 93, 101, 188 |
| TEM-R164 (WT) | TTCTGACAACGATCGGAGGAC (SEQ ID NO: 277) | TCGTGGTGTCACGCTCGTC (SEQ ID NO: 278) | TCCCAACGATCAAGGC (SEQ ID NO: 279) | TEM-1-4, 13, 15, 18-22, 25, 30-42, 44, 45, 47-52, 54-59, 62, 65-74, 76-84, 88-90, 92-101, 103-106, 108, 110-113, 116, 117, 119, 120, 122-124, 126-128, 135, 138-140, 145, 146, 148, 150, 153, 156, 157, 159, 160, 162-164, 166-176, 178-183, 185, 186, 188-192, 194, 196-204, 206-222 |
| TEM-R164C | TTCTGACAACGATCGGAGGAC (SEQ ID NO: 277) | TCGTGGTGTCACGCTCGTC (SEQ ID NO: 278) | TCCCAACAATSAAGGC (SEQ ID NO: 280) | TEM-87, 92, 143, 144, 193, 195 |
| TEM-R164H | TTCTGACAACGATCGGAGGAC (SEQ ID NO: 277) | TCGTGGTGTCACGCTCGTC (SEQ ID NO: 278) | TCCCAATGATCAAGGC (SEQ ID NO: 281) | TEM-6, 11, 16, 27-29, 43, 61, 75, 107, 109, 115, 118, 132, 134, 147, 151, 152, 161, 187 |

TABLE 10-continued

| Assay Name | Forward Primer Sequence | Reverse Primer Sequence | Probe Sequence | Gene Subtypes Covered |
|---|---|---|---|---|
| TEM-R1645 | TTCTGACAACGATCGGAGGAC (SEQ ID NO: 277) | TCGTGGTGTCACGCTCGTC (SEQ ID NO: 278) | TCCCAACTATCAAGGC (SEQ ID NO: 282) | TEM-5, 7-10, 12, 24, 26, 46, 53, 60, 63, 85, 86, 102, 114, 121, 125, 129-131, 133, 136, 137, 149, 154, 155, 158, 165, 177, 184, 205 |
| TLA-1 | CTGTTGTTGCTCATAAAACCGAAG (SEQ ID NO: 283) | CCGATATCATTGTGGCAGCAGTA (SEQ ID NO: 284) | CTCCGATACTAACGAT (SEQ ID NO: 285) | TLA-1 |
| VEB-1 | GCAATGAGAAGGATACTTTKAAGATTA (SEQ ID NO: 286) | CGGAAATTTCATAACGCTTTGC (SEQ ID NO: 287) | CTTCCATTTCCCGAT (SEQ ID NO: 288) | VEB-1-9 |
| VIM-1 | GTGCGCTTCGGTCCAG (SEQ ID NO: 30) | CAGATTGTCGGTCGAATGC (SEQ ID NO: 31) | CAGCACCAGGATAG (SEQ ID NO: 51) | VIM-1, 4, 12, 14, 19, 26, 27, 28, 29, 32, 33, 34, 35, 37, 39 |
| VIM-13 | TCGCAACGCATACGTTTGATG (SEQ ID NO: 289) | ATCAAAAGCAACTCATCGCCATC (SEQ ID NO: 290) | CCCGTCCAATGGTC (SEQ ID NO: 291) | VIM-13 |
| VIM-2 | GTGCGCTTCGGTCCAG (SEQ ID NO: 30) | TAAGTTGTCGGTCGAATGC (SEQ ID NO: 32) | CAGCACCAGGATAG (SEQ ID NO: 51) | VIM-2, 3, 6, 8, 9, 10, 11, 15, 16, 17, 18, 23, 24, 31, 36 |
| VIM-5 | GTGCGCTTCGGTCCAG (SEQ ID NO: 30) | CAGATTGTCGGTCGAATGC (SEQ ID NO: 31) | CAGCACCGGGATAG (SEQ ID NO: 52) | VIM-5, 25, 38 |

Y = C, T
R = G, A
S = C, G
W = A, T
K = G, T
M = A, C

We claim:

1. A method of detecting a multi-drug resistant bacterial colonization or infection in a patient and taking a contact precaution with regard to the patient, comprising:

a. isolating a nucleic acid sample from a biological sample obtained from the patient;

b. simultaneously amplifying at least one antibiotic resistant gene subtype from each of the KPC, NDM, OXA, VIM, IMP, CTX-M and VanA antibiotic resistant gene families by contacting the nucleic acid sample with one or more amplification primers that specifically hybridize to a substantially identical region common to at least two antibiotic resistant gene subtypes in each antibiotic resistant gene family to provide an enriched nucleic acid sample, wherein the nucleic acid sample is contacted by an internal amplification control nucleic acid prior to amplification;

c. simultaneously detecting the presence of the at least one antibiotic resistant gene subtype by contacting the enriched nucleic acid sample with one or more detection primers that specifically hybridize to the substantially identical region or to another substantially identical region common to at least two antibiotic resistant gene subtypes in each antibiotic resistant gene family, wherein said contacting results in amplification of the substantially identical region or amplification of another substantially identical region common to at least two antibiotic resistant gene subtypes in each antibiotic resistant gene family;

d. detecting the presence of a multi-drug resistant bacterial colonization or infection in the patient by detecting the presence of at least one antibiotic resistant gene subtype from each of the antibiotic resistant gene families in the enriched nucleic acid sample based on the detection results obtained in step c; and e. taking a contact precaution with regard to the patient in whom the presence of a multi-drug resistant bacterial colonization or infection is detected in step d, wherein the contact precaution is isolating the patient to a quarantine area or ward or donning personal protective apparel upon entering the patient's room;

wherein the detection primers are:
(i) a forward primer of SEQ ID NO:26 and a reverse primer of SEQ ID NO:27 for the KPC antibiotic resistant gene family;
(ii) a forward primer of SEQ ID NO:28 and a reverse primer of SEQ ID NO:29 for the NDM antibiotic resistant gene family;
(iii) a forward primer of SEQ ID NO:37 and a reverse primer of SEQ ID NO:38 for the OXA antibiotic resistant gene family;
(iv) a forward primer of SEQ ID NO:30 and a reverse primer of SEQ ID NO:31 and/or a forward primer of SEQ ID NO:30 and a reverse primer of SEQ ID NO:32 for the VIM antibiotic resistant gene family;
(v) a forward primer of SEQ ID NO:39 and a reverse primer of SEQ ID NO:40 for the IMP antibiotic resistant gene family;
(vi) a forward primer of SEQ ID NO:43 and a reverse primer of SEQ ID NO:44 and/or a forward primer of SEQ ID NO:45 and a reverse primer of SEQ ID NO:46 for the CTX-M antibiotic resistant gene family; and
(vii) a forward primer of SEQ ID NO:41 and a reverse primer of SEQ ID NO:42 for the VanA antibiotic resistant gene family.

2. The method of claim 1, further comprising:
amplifying at least one antibiotic gene subtype from one or more of the IMI, SME, GIM, SPM, NMC, SFC, SHV, TEM, BEL, VEB, GES, PER, SFO, BES, TLA, ACC, CMY, MIR, ACT, DHA, MOX, FOX, and CFE antibiotic resistant gene families by contacting the nucleic acid sample with one or more amplification primers that specifically hybridizes to a substantially homologous region common to at least two antibiotic gene subtypes in the one or more antibiotic resistant gene family to provide a further enriched nucleic acid sample; and detecting the presence of the at least one antibiotic gene subtype by contacting the further enriched nucleic acid sample with one or more detection primer that specifically hybridizes to the substantially homologous region or to another substantially homologous region common to at least two antibiotic gene subtypes in the one or more antibiotic resistant gene family.

3. The method of claim 1, further comprising providing a private room for the patient, limiting the patient's mobility, limiting or restricting access of non-colonized or non-infected patients or medical personnel to the patient, or providing dedicated patient care equipment to the patient.

4. The method of claim 1, wherein the biological sample is an anal swab, a rectal swab, a skin swab, nasal swab, wound swab, stool, blood, plasma, serum, urine, sputum, respiratory lavage, cerebrospinal fluid, bacteria culture, bacteria isolate, fungal culture, fungal isolate, virus culture or virus isolate.

5. The method of claim 1, wherein said patient is at high risk for having a multi-drug resistant bacteria colonization or infection.

6. The method of claim 1, further comprising:
f. treating the patient in whom at least one antibiotic resistant gene subtype from each of the KPC, NDM, OXA, VIM, and IMP antibiotic resistant gene families is detected in step d with an antibiotic other than a carbapenem antibiotic;
treating the patient in whom at least one antibiotic resistant gene subtype from the CTX-M antibiotic resistant gene family is detected in step d with an antibiotic other than a cephalosporin antibiotic; or
treating the patient in whom at least one antibiotic resistant gene subtype from the VanA antibiotic resistant gene family is detected in step d an antibiotic other than vancomycin.

7. The method of claim 2, further comprising:
a. treating the patient with an antibiotic other than a carbapenem antibiotic when at least one antibiotic resistant gene subtype from one of the SME, SFC, IMI, NMC, or CcrA antibiotic resistant gene families is detected;
b. treating the patient with an antibiotic other than a cephalosporin antibiotic when at least one antibiotic resistant gene subtype from one of the PER, VEB, GES, BES, SFO, TLA, TEM with amino acid substitutions E104K, R164H, R164S, R164C, G238S or E240K, SHV with amino acid substitutions G156D, G238S or E240K antibiotic resistant gene families is detected; or
c. treating the patient with an antibiotic other than a beta-lactamase inhibitor-beta-lactam combination when at least one antibiotic resistant gene subtype from one of the ACC, MOX, CMY, CFE, ACT, DHA or FOX is detected.

8. The method of claim 1, further comprising testing the biological sample to identify the phenotype of the multi-drug resistant organism.

9. The method of claim 1 further comprising culturing the biological sample and confirming drug resistance.

10. A method of detecting and treating a bacterial infection in a patient known to be or suspected of being colonized with or having a bacterial infection, comprising:
a. isolating a nucleic acid sample from a biological sample obtained from the patient;
b. simultaneously amplifying at least one antibiotic resistant gene subtype from each of the KPC, NDM, OXA, VIM, IMP, CTX-M and VanA antibiotic resistant gene families by contacting the nucleic acid sample with one or more amplification primers that specifically hybridize to a substantially identical region common to at least two antibiotic resistant gene subtypes in each antibiotic resistant gene family to provide an enriched nucleic acid sample, wherein the nucleic acid sample is contacted by an internal amplification control nucleic acid prior to amplification;

c. simultaneously detecting the presence of the at least one antibiotic resistant gene subtype by contacting the enriched nucleic acid sample with one or more detection primers that specifically hybridize to the substantially identical region or to another substantially identical region common to at least two antibiotic resistant gene subtypes in each antibiotic resistant gene family, wherein said contacting results in amplification of the substantially identical region or amplification of another substantially identical region common to at least two antibiotic resistant gene subtypes in each antibiotic resistant gene family;

d. detecting the presence of at least one antibiotic resistant gene subtype in the enriched nucleic acid sample based on the detection results obtained in step c; and e. treating the patient in whom at least one antibiotic resistant gene subtype from each of the KPC, NDM, OXA, VIM, and IMP antibiotic resistant gene families is detected in step d with an antibiotic other than a carbapenem antibiotic;

treating the patient in whom at least one antibiotic resistant gene subtype from the CTX-M antibiotic resistant gene family is detected in step d with an antibiotic other than a cephalosporin antibiotic; or treating the patient in whom at least one antibiotic resistant gene subtype from the VanA antibiotic resistant gene family is detected in step d with an antibiotic other than vancomycin;

wherein the detection primers are:
(i) a forward primer of SEQ ID NO:26 and a reverse primer of SEQ ID NO:27 for the KPC antibiotic resistant gene family;
(ii) a forward primer of SEQ ID NO:28 and a reverse primer of SEQ ID NO:29 for the NDM antibiotic resistant gene family;
(iii) a forward primer of SEQ ID NO:37 and a reverse primer of SEQ ID NO:38 for the OXA antibiotic resistant gene family;
(iv) a forward primer of SEQ ID NO:30 and a reverse primer of SEQ ID NO:31 and/or a forward primer of SEQ ID NO:30 and a reverse primer of SEQ ID NO:32 for the VIM antibiotic resistant gene family;
(v) a forward primer of SEQ ID NO:39 and a reverse primer of SEQ ID NO:40 for the IMP antibiotic resistant gene family;
(vi) a forward primer of SEQ ID NO:43 and a reverse primer of SEQ ID NO:44 and/or a forward primer of SEQ ID NO:45 and a reverse primer of SEQ ID NO:46 for the CTX-M antibiotic resistant gene family; and
(vii) a forward primer of SEQ ID NO:41 and a reverse primer of SEQ ID NO:42 for the VanA antibiotic resistant gene family.

11. The method of claim 10, further comprising amplifying and detecting at least one antibiotic resistant gene subtype from one or more of the IMI, SME, GIM, SPM, NMC, SFC, SHV, TEM, BEL, VEB, GES, PER, SFO, BES, TLA, ACC, CMY, MIR, ACT, DHA, MOX, FOX, and CFE antibiotic resistant gene families, and treating the patient with an antibiotic other than a carbapenem antibiotic when at least one antibiotic resistant gene subtype from the SME, SFC, IMI, NMC, or CcrA antibiotic resistant gene families is detected treating the patient with an antibiotic other than a cephalosporin antibiotic when at least one antibiotic resistant gene subtype from the PER, VEB, GES, BES, SFO, or TLA antibiotic resistant gene family is detected, a TEM antibiotic gene subtype with amino acid substitution E104K, R164H, R164S, R164C, G238S, or E240K is detected, or an SHV antibiotic gene subtype with amino acid substitution G156D, G238S or E240K antibiotic resistant gene families is detected; or treating the patient with an antibiotic other than a beta-lactamase inhibitor-beta-lactam combination when at least one antibiotic gene subtype from the ACC, MOX, CMY, CFE, ACT, DHA, or FOX antibiotic resistant gene families is detected.

12. A method of detecting and treating a bacterial infection in an asymptomatic patient known to be or suspected of being colonized with or having a bacterial infection, comprising:

a. isolating a nucleic acid sample from a biological sample obtained from the patient;

b. simultaneously amplifying at least one antibiotic resistant gene subtype from each of the KPC, NDM, OXA, VIM, IMP, CTX-M and VanA antibiotic resistant gene families by contacting the nucleic acid sample with one or more amplification primers that specifically hybridize to a substantially identical region common to at least two antibiotic resistant gene subtypes in each antibiotic resistant gene family to provide an enriched nucleic acid sample, wherein the nucleic acid sample is contacted by an internal amplification control nucleic acid prior to amplification;

c. simultaneously detecting the presence of the at least one antibiotic resistant gene subtype by contacting the enriched nucleic acid sample with one or more detection primers that specifically hybridize to the substantially identical region or to another substantially identical region common to at least two antibiotic resistant gene subtypes in each antibiotic resistant gene family, wherein said contacting results in amplification of the substantially identical region or amplification of another substantially identical region common to at least two antibiotic resistant gene subtypes in each antibiotic resistant gene family;

d. detecting the presence of at least one antibiotic resistant gene subtype in the enriched nucleic acid sample based on the detection results obtained in step c; and e. treating the patient in whom at least one antibiotic resistant gene subtype from each of the KPC, NDM, OXA, VIM, and IMP antibiotic resistant gene families is detected in step d with an antibiotic other than a carbapenem antibiotic;

treating the patient in whom at least one antibiotic resistant gene subtype from the CTX-M antibiotic resistant gene family is detected in step d with an antibiotic other than a beta-lactam antibiotic; or treating the patient in whom at least one antibiotic resistant gene subtype from the VanA antibiotic resistant gene family is detected in step d with an antibiotic other than vancomycin;

wherein the detection primers are:
(i) a forward primer of SEQ ID NO:26 and a reverse primer of SEQ ID NO:27 for the KPC antibiotic resistant gene family;

(ii) a forward primer of SEQ ID NO:28 and a reverse primer of SEQ ID NO:29 for the NDM antibiotic resistant gene family;
(iii) a forward primer of SEQ ID NO:37 and a reverse primer of SEQ ID NO:38 for the OXA antibiotic resistant gene family;
(iv) a forward primer of SEQ ID NO:30 and a reverse primer of SEQ ID NO:31 and/or a forward primer of SEQ ID NO:30 and a reverse primer of SEQ ID NO:32 for the VIM antibiotic resistant gene family;
(v) a forward primer of SEQ ID NO:39 and a reverse primer of SEQ ID NO:40 for the IMP antibiotic resistant gene family;
(vi) a forward primer of SEQ ID NO:43 and a reverse primer of SEQ ID NO:44 and/or a forward primer of SEQ ID NO:45 and a reverse primer of SEQ ID NO:46 for the CTX-M antibiotic resistant gene family; and
(vii) a forward primer of SEQ ID NO:41 and a reverse primer of SEQ ID NO:42 for the VanA antibiotic resistant gene family.

13. The method of claim 12, further comprising amplifying and detecting at least one antibiotic gene subtype from one or more of the IMI, SME, GIM, SPM, NMC, SFC, SHV, TEM, BEL, VEB, GES, PER, SFO, BES, TLA, ACC, CMY, MIR, ACT, DHA, MOX, FOX, and CFE antibiotic resistant gene families; and
treating the patient with an antibiotic other than a carbapenem antibiotic when at least one antibiotic resistant gene subtype from the SME, SFC, IMI, NMC, or CcrA antibiotic resistant gene families is detected
treating the patient with an antibiotic other than a cephalosporin antibiotic when at least one antibiotic resistant gene subtype from the PER, VEB, GES, BES, SFO, or TLA antibiotic resistant gene family is detected, a TEM antibiotic gene subtype with amino acid substitution E104K, R164H, R164S, R164C, G238S, or E240K is detected, or an SHV antibiotic gene subtype with amino acid substitution G156D, G238S or E240K antibiotic resistant gene families is detected; or
treating the patient with an antibiotic other than a beta-lactamase inhibitor-beta-lactam combination when at least one antibiotic gene subtype from the ACC, MOX, CMY, CFE, ACT, DHA, or FOX antibiotic resistant gene families is detected.

14. The method of claim 12, wherein the biological sample is an anal swab, a rectal swab, a skin swab, nasal swab, wound swab, stool, blood, plasma, serum, urine, sputum, respiratory lavage, cerebrospinal fluid, bacteria culture, bacteria isolate, fungal culture, fungal isolate, virus culture or virus isolate.

15. The method of claim 1, further comprising determining the species of the multi-drug resistant bacterium in the patient by identifying and quantifying the level of the subtype of at least one antibiotic resistant gene subtype from each of the antibiotic resistant gene families in the enriched nucleic acid sample.

16. The method of claim 1, wherein the biological sample comprises less than 210 colony-forming units (CFU) of a multi-drug resistant bacterium.

17. The method of claim 1, wherein the biological sample comprises less than 15 colony-forming units (CFU) of a multi-drug resistant bacterium.

18. The method of claim 10, wherein the biological sample is an anal swab, a rectal swab, a skin swab, a nasal swab, a wound swab, stool, blood, plasma, serum, urine, sputum, respiratory lavage, cerebrospinal fluid, a bacterial culture, a bacterial isolate, a fungal culture, a fungal isolate, a virus culture, or a virus isolate.

19. The method of claim 10, further comprising determining the species of the multi-drug resistant bacterium in the patient by identifying and quantifying the level of the subtype of at least one antibiotic resistant gene subtype from each of the antibiotic resistant gene families in the enriched nucleic acid sample.

20. The method of claim 10, wherein the biological sample comprises less than 210 colony-forming units (CFU) of a multi-drug resistant bacterium.

21. The method of claim 10, wherein the biological sample comprises less than 15 colony-forming units (CFU) of a multi-drug resistant bacterium.

22. The method of claim 12, further comprising determining the species of the multi-drug resistant bacterium in the patient by identifying and quantifying the level of the subtype of at least one antibiotic resistant gene subtype from each of the antibiotic resistant gene families in the enriched nucleic acid sample.

23. The method of claim 12, wherein the biological sample comprises less than 210 colony-forming units (CFU) of a multi-drug resistant bacterium.

24. The method of claim 12, wherein the biological sample comprises less than 15 colony-forming units (CFU) of a multi-drug resistant bacterium.

* * * * *